United States Patent
Kanno et al.

(10) Patent No.: US 6,339,045 B1
(45) Date of Patent: Jan. 15, 2002

(54) N-(UNSUBSTITUTED OR SUBSTITUTED)-4-SUBSTITUTED-6-(UNSUBSTITUTED OR SUBSTITUTED)PHENOXY-2-PYRIDINECARBOXAMIDES OR THIOCARBOXAMIDES, PROCESSES FOR PRODUCING THE SAME, AND HERBICIDES

(75) Inventors: Hisashi Kanno, Fukushima; Yoshikazu Kubota, Chiba; Tsutomu Sato; Koki Sato, both of Fukushima, all of (JP)

(73) Assignee: Kureha Kagaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/091,794

(22) PCT Filed: Dec. 26, 1996

(86) PCT No.: PCT/JP96/03807

§ 371 Date: Aug. 12, 1998

§ 102(e) Date: Aug. 12, 1998

(87) PCT Pub. No.: WO97/24330

PCT Pub. Date: Jul. 10, 1997

(30) Foreign Application Priority Data

Dec. 28, 1995 (JP) .............................. 7-353264
May 10, 1996 (JP) .............................. 8-140720

(51) Int. Cl.$^7$ ...................... A01N 43/40; C07D 213/64; C07D 213/70; C07D 213/81

(52) U.S. Cl. ...................... 504/244; 546/292; 546/296; 546/313; 546/323

(58) Field of Search ................. 546/292, 296, 546/313, 323; 504/244

(56) References Cited

FOREIGN PATENT DOCUMENTS

| DE | 2508932 | 9/1976 |
|---|---|---|
| EP | 0853066 A1 | 7/1998 |
| EP | 0919522 A1 | 6/1999 |
| JP | 57-118568 | 7/1982 |
| JP | 4-217959 | 8/1992 |
| JP | 4-290805 | 10/1992 |
| WO | WO 96/6096 | 2/1996 |

*Primary Examiner*—Alan L. Rotman
(74) *Attorney, Agent, or Firm*—Nixon & Vanderhye

(57) ABSTRACT

N-(substituted or unsubstituted)-4-substituted-6-(substituted or unsubstituted) phenoxy-2-pyridine carboxamide or thiocarboxamide represented by the general formula (I) and a process for producing the compound.

A herbicide containing as an effective ingredient N-(substituted or unsubstituted)-4-substituted-6-(substituted or unsubstituted) phenoxy-2-pyridine carboxamide or thiocarboxamide represented by the general formula (I).

9 Claims, No Drawings

N-(UNSUBSTITUTED OR SUBSTITUTED)-4-SUBSTITUTED-6-(UNSUBSTITUTED OR SUBSTITUTED)PHENOXY-2-PYRIDINECARBOXAMIDES OR THIOCARBOXAMIDES, PROCESSES FOR PRODUCING THE SAME, AND HERBICIDES

TECHNICAL FIELD

The present invention relates to N-(substituted or unsubstituted)-4-substituted-6-(substituted or unsubstituted) phenoxy-2-pyridine carboxamide or thiocarboxamide, a process for producing the above-mentioned compound and a herbicide containing the above-mentioned compound.

BACKGROUND ART

Certain kinds of N-(substituted or unsubstituted)-6-(substituted or unsubstituted) phenoxy-2-pyridine carboxamides or thiocarboxamides are disclosed in Japanese Patent Applications Laid-open (KOKAI) Nos. 4-290805(1992) and 4-217959(1992). Hitherto, various herbicides including such compounds have been proposed. However, there has been still a strong demand for providing herbicides having an excellent herbicidal effect, such as a herbicide capable of surely exhibiting a herbicidal effect even when used in a small amount, such that its amount existing in environment can be advantageously reduced; a herbicide capable of exhibiting a good selectivity between crop and weed irrespective of change in environmental conditions; a herbicide causing no phytotoxicity even after crop rotation or double-cropping; or the like.

The present invention has been achieved in view of the above-mentioned problems. It is an object of the present invention to provide a compound having an excellent herbicidal effect, i.e., those capable of surely exhibiting a herbicidal effect even when used in a small amount, showing a good selectivity between crop and weed, and causing no phytotoxicity even after crop rotation or double-cropping, a process for the production of such a compound, and a herbicide using such a compound.

As a result of the present inventors' earnest studies concerning chemical structures and physiological activities to plants for discovering novel industrially useful pyridine derivatives, it has been surprisingly found that by introducing a substituent group such as alkoxy group, alkylthio group, alkylamino group or dialkylamino group into the 4-position of pyridine ring, the obtained compound can exhibit an extremely high herbicidal effect as compared to those having a pyridine ring whose 4-position is unsubstituted, which have been described as suitable compounds in Japanese Patent Application Laid-open (KOKAI) No. 4-290805(1992). The present invention has been attained on the basis of the finding.

More specifically, it has been found that by introducing the above-mentioned substituent group into the 4-position of pyridine ring, there can be produced an N-(substituted or unsubstituted)-4-substituted-6-(substituted or unsubstituted) phenoxy-2-pyridine carboxamide or thiocarboxamide compound having a higher herbicidal activity than that of conventional ones.

DISCLOSURE OF THE INVENTION

That is, in a first aspect of the present invention, there is provided N-(substituted or unsubstituted)-4-substituted-6-(substituted or unsubstituted) phenoxy-2-pyridine carboxamide or thiocarboxamide represented by the general formula (I):

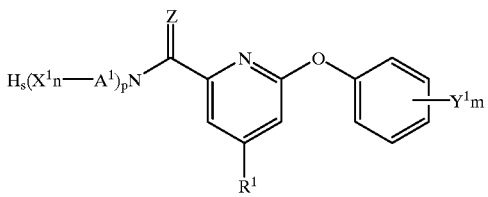

wherein $R^1$ is a $C_1$ to $C_4$ alkoxy group, a $C_1$ to $C_4$ alkylthio group, a $C_1$ to $C_4$ alkylamino group, a di($C_1$ to $C_4$ alkyl) amino group or a ($C_1$ to $C_4$ alkyl)($C_7$ to $C_8$ aralkyl)amino group;

$A^1$ may be substituted with $X^1$, and is a $C_1$ to $C_{10}$ alkyl group, a $C_2$ to $C_6$ alkenyl group, a $C_3$ to $C_6$ alkynyl group, a $C_3$ to $C_6$ cycloalkyl group, a $C_1$ to $C_{10}$ alkoxy group, a $C_3$ to $C_6$ alkenyloxy group, a $C_3$ to $C_6$ alkynyloxy group, a $C_1$ to $C_{10}$ alkylamino group, a di($C_1$ to $C_6$ alkyl)amino group, a phenyl group, a phenylamino group, an arylalkyl group (whose alkyl moiety has 1 to 3 carbon atoms), an arylalkyloxy group (whose alkyl moiety has 1 to 3 carbon atoms), an arylalkylamino group (whose alkyl moiety has 1 to 3 carbon atoms), an amino group or a hydroxyl group {wherein the chain-like hydrocarbon moiety of $A^1$ is constituted by a longest carbon chain as a main chain exclusive of a $C_1$ to $C_4$ alkyl group bonded as side chain to the main chain, and the $C_1$ to $C_4$ alkyl group as side chain is regarded as $X^1$};

$X^1$ is a halogen atom, a $C_1$ to $C_4$ alkoxy group, a $C_1$ to $C_4$ alkylthio group, a $C_1$ to $C_4$ alkyl group {which is not bonded to a terminal position of $A^1$ when $A^1$ is a $C_1$ to $C_{10}$ alkyl group, a $C_1$ to $C_{10}$ alkoxy group, a $C_1$ to $C_{10}$ alkylamino group or a di($C_1$ to $C_6$ alkyl)amino group}, a $C_3$ to $C_6$ cycloalkyl group, a $C_1$ to $C_4$ alkylcarbonyl group, a $C_1$ to $C_4$ alkylamino group, a di($C_1$ to $C_4$ alkyl)amino group, a $C_1$ to $C_4$ alkylsulfonyl group, a $C_1$ to $C_4$ alkylsulfinyl group, a hydroxyl group, an amino group, a cyano group or a thiol group, wherein the alkyl moiety of $X^1$ may be substituted with halogen atom(s);

n is 0 or an integer selected from numbers of hydrogen atoms of $A^1$ which can be substituted with $X^1$, and when n is an integer of not less than 2, $X^1$s may be the same or different;

p and s are an integer of 0 to 2 with the proviso that the sum of p and s (p+s) is 2;

when p is 2, $A^1$ may be the same or different;

when p is 2 and two $A^1$s are alkyl chains, the $A^1$s may be directly bonded together to form a ring, or the $A^1$s may be bonded to each other through an oxygen atom of the hydroxyl group or a nitrogen atom of the amino group or the $C_1$ to $C_4$ alkylamino group which groups are bonded to one of the $A^1$s, to form a ring;

$Y^1$ is a $C_1$ to $C_4$ haloalkyl group, a $C_1$ to $C_4$ alkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom;

m is an integer of 0 to 5, and when m is not less than 2, $Y^1$s may be the same or different; and Z is an oxygen atom or a sulfur atom.

In a second aspect of the present invention, there is provided a process for producing N-substituted-4-substituted-6-(substituted or unsubstituted) phenoxy-2- pyridine carboxamide or thiocarboxamide represented by the general formula (I-a), which process comprises carrying out an addition reaction between 2-(metal-substituted)-4-substituted-6-(substituted or unsubstituted) phenoxy pyridine represented by the general formula (II) and substituted isocyanate (or isothiocyanate) represented by the general formula (III); and substituting the metal with a proton.

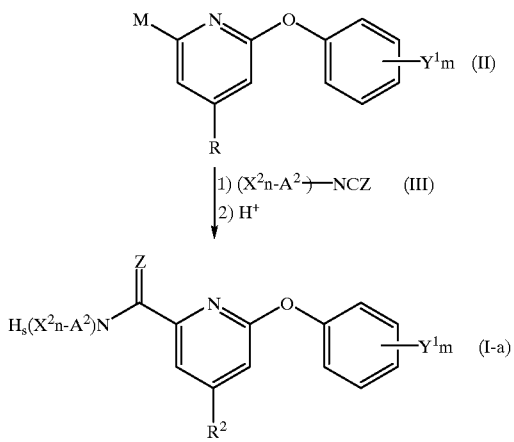

wherein $R^2$ is a $C_1$ to $C_4$ alkoxy group, a $C_1$ to $C_4$ alkylthio group, a di($C_1$ to $C_4$ alkyl)amino group or a ($C_1$ to $C_4$ alkyl)($C_7$ to $C_8$ aralkyl)amino group;

- $A^2$ may be substituted with $X^2$, and is a $C_1$ to $C_{10}$ alkyl group, a $C_2$ to $C_6$ alkenyl group, a $C_3$ to $C_6$ alkynyl group, a $C_3$ to $C_6$ cycloalkyl group, a phenyl group or an arylalkyl group (whose alkyl moiety has 1 to 3 carbon atoms) {wherein the chain-like hydrocarbon moiety of $A^2$ is constituted by a longest carbon chain as a main chain exclusive of a $C_1$ to $C_4$ alkyl group bonded as side chain to the main chain, and the $C_1$ to $C_4$ alkyl group as side chain is regarded as $X^2$};
- $X^2$ is a halogen atom, a $C_1$ to $C_4$ alkoxy group, a $C_1$ to $C_4$ alkylthio group, a $C_1$ to $C_4$ alkyl group {which is not bonded to a terminal position of $A^2$ when $A^2$ is a $C_1$ to $C_{10}$ alkyl group}, a $C_3$ to $C_6$ cycloalkyl group or a di($C_1$ to $C_4$ alkyl)amino group, wherein the alkyl moiety of $X^2$ may be further substituted with halogen atom(s);
- n is 0 or an integer selected from numbers of hydrogen atoms of $A^2$ which can be substituted with $X^2$, and when n is an integer of not less than 2, $X^2$s may be the same or different;
- $Y^1$ is a $C_1$ to $C_4$ haloalkyl group, a $C_1$ to $C_4$ alkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom;
- m is an integer of 0 to 5, and when m is an integer of not less than 2, $Y^1$s may be the same or different;
- Z is an oxygen atom or a sulfur atom; and
- M is alkali metal, alkali earth metal-Q wherein Q is a halogen atom, or ½(Cu-alkali metal).

In a third aspect of the present invention, there is provided a process for producing N-(substituted or unsubstituted)-4-substituted-6-(substituted or unsubstituted) phenoxy-2-pyridine carboxamide or thiocarboxamide represented by the general formula (I-b), which process comprises reacting a compound represented by the general formula (IV) with (substituted or unsubstituted) amine, (substituted or unsubstituted) hydroxyl amine or (substituted or unsubstituted) hydrazine represented by the general formula (V).

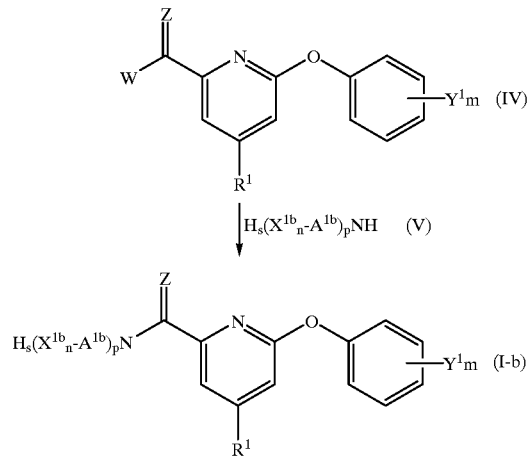

wherein $R^1$ is a $C_1$ to $C_4$ alkoxy group, a $C_1$ to $C_4$ alkylthio group, a $C_1$ to $C_4$ alkylamino group, a di($C_1$ to $C_4$ alkyl) amino group or a ($C_1$ to $C_4$ alkyl)($C_7$ to $C_8$ aralkyl)amino group;

$A^{1b}$ may be substituted with $X^{1b}$, and is a $C_1$ to $C_{10}$ alkyl group, a $C_2$ to $C_6$ alkenyl group, a $C_3$ to $C_6$ alkynyl group, a $C_3$ to $C_6$ cycloalkyl group, a $C_1$ to $C_{10}$ alkoxy group, a $C_3$ to $C_6$ alkenyloxy group, a $C_3$ to $C_6$ alkynyloxy group, a $C_1$ to $C_{10}$ alkylamino group, a di($C_1$ to $C_6$ alkyl)amino group, a phenyl group, a phenylamino group, an arylalkyl group (whose alkyl moiety has 1 to 3 carbon atoms), an arylalkyloxy group (whose alkyl moiety has 1 to 3 carbon atoms), an arylalkylamino group (whose alkyl moiety has 1 to 3 carbon atoms), an amino group or a hydroxyl group {wherein the chain-like hydrocarbon moiety of $A^{1b}$ is constituted by a longest carbon chain as a main chain exclusive of a $C_1$ to $C_4$ alkyl group bonded as side chain to the main chain, and the $C_1$ to $C_4$ alkyl group as side chain is regarded as $X^{1b}$};

$X^{1b}$ is a halogen atom, a $C_1$ to $C_4$ alkoxy group, a $C_1$ to $C_4$ alkylthio group, a $C_1$ to $C_4$ alkyl group {which is not bonded to a terminal position of $A^{1b}$ when $A^{1b}$ is a $C_1$ to $C_{10}$ alkyl group, a $C_1$ to $C_{10}$ alkoxy group, a $C_1$ to $C_{10}$ alkylamino group or a di($C_1$ to $C_6$ alkyl)amino group}, a $C_3$ to $C_6$ cycloalkyl group, a $C_1$ to $C_4$ alkylcarbonyl group, a $C_1$ to $C_4$ alkylamino group, a di($C_1$ to $C_4$ alkyl)amino group, a $C_1$ to $C_4$ alkylsulfonyl group, a $C_1$ to $C_4$ alkylsulfinyl group, a hydroxyl group, an amino group, a cyano group or a thiol group, wherein the alkyl moiety of $X^{1b}$ may be substituted with halogen atom(s);

n is 0 or an integer selected from numbers of hydrogen atoms of $A^{1b}$ which can be substituted with $X^{1b}$, and when n is an integer of not less than 2, $X^{1b}$s may be the same or different;

p and s are an integer of 0 to 2 with the proviso that the sum of p and s (p+s) is 2;

when p is 2, $A^{1b}$s may be the same or different;

when p is 2 and the $A^{1b}$s are alkyl chains, the $A^{1b}$s may be directly bonded together to from a ring, or the $A^{1b}$s may be bonded to each other through an oxygen atom of the hydroxyl group or a nitrogen atom of the amino group or the $C_1$ to $C_4$ alkylamino group which groups are bonded to one of the $A^{1b}$s, to form a ring;

$Y^1$ is a $C_1$ to $C_4$ haloalkyl group, a $C_1$ to $C_4$ alkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom;

m is an integer of 0 to 5, and when m is not less than 2, $Y^1$s may be the same or different;

Z is an oxygen atom or a sulfur atom; and

W is a leaving group.

In a fourth aspect of the present invention, there is provided a process for producing N-substituted-4-substituted-6-(substituted or unsubstituted) phenoxy-2-pyridine carboxamide or thiocarboxamide represented by the general formula (I-c), which process comprises reacting N-(substituted or unsubstituted)-4-substituted-6-(substituted or unsubstituted) phenoxy-2-pyridine carboxamide represented by the general formula (VI) with a compound represented by the general formula (VII-a),

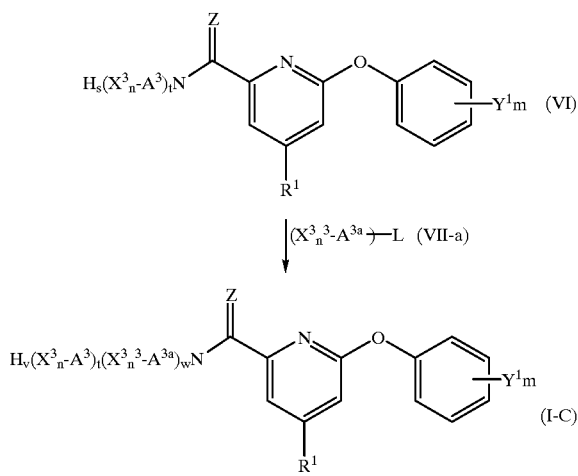

wherein $R^1$ is a $C_1$ to $C_4$ alkoxy group, a $C_1$ to $C_4$ alkylthio group, a $C_1$ to $C_4$ alkylamino group, a di($C_1$ to $C_4$ alkyl) amino group or a ($C_1$ to $C_4$ alkyl)($C_7$ to $C_8$ aralkyl)amino group;

$A^3$ may be substituted with $X^3$, and is a $C_1$ to $C_{10}$ alkyl group, a $C_3$ to $C_6$ alkenyl group, a $C_3$ to $C_6$ alkynyl group, a $C_3$ to $C_6$ cycloalkyl group, a $C_1$ to $C_{10}$ alkoxy group, a $C_3$ to $C_6$ alkenyloxy group, a $C_3$ to $C_6$ alkynyloxy group, a di($C_1$ to $C_6$ alkyl)amino group, a phenyl group, an arylalkyl group (whose alkyl moiety has 1 to 3 carbon atoms) or an arylalkyloxy group (whose alkyl moiety has 1 to 3 carbon atoms) {wherein the chain-like hydrocarbon moiety of $A^3$ is constituted by a longest carbon chain as a main chain exclusive of a $C_1$ to $C_4$ alkyl group bonded as side chain to the main chain, and the $C_1$ to $C_4$ alkyl group as side chain is regarded as $X^3$};

$A^{3a}$ may be substituted with $X^3$, and is a $C_1$ to $C_{10}$ alkyl group, a $C_3$ to $C_6$ alkenyl group, a $C_3$ to $C_6$ alkynyl group, a $C_3$ to $C_6$ cycloalkyl group or an arylalkyl group (whose alkyl moiety has 1 to 3 carbon atoms) {wherein the chain-like hydrocarbon moiety of $A^{3a}$ is constituted by a longest carbon chain as a main chain exclusive of side chain bonded to the main chain, and the side chain is regarded as $X^3$};

$X^3$ is a halogen atom, a $C_1$ to $C_4$ alkoxy group, a $C_1$ to $C_4$ alkylthio group, a $C_1$ to $C_4$ alkyl group {which is not bonded to terminal positions of $A^3$ and $A^{3a}$, when $A^3$ and $A^{3a}$ are a $C_1$ to $C_{10}$ alkyl group, a $C_1$ to $C_{10}$ alkoxy group or a di($C_1$ to $C_6$ alkyl)amino group}, a $C_3$ to $C_6$ cycloalkyl group, a $C_1$ to $C_4$ alkylamino group, a di($C_1$ to $C_4$ alkyl)amino group, a $C_1$ to $C_4$ alkylsulfonyl group, a $C_1$ to $C_4$ alkylsulfinyl group or a cyano group, wherein the alkyl moiety of $X^3$ may be substituted with halogen atom(s);

n and $n^3$ are 0 or an integer selected from numbers of hydrogen atoms of $A^3$ and $A^{3a}$, respectively, which can be substituted with $X^3$, and when n and $n^3$ are an integer of not less than 2, $X^3$s may be the same or different;

v is 0 or 1, t is 0 or 1, and w is 1 or 2 with the proviso that the sum of t and v (t+v) is 0 or 1 and the sum of t, v and w (t+v+w) is 2;

when w is 2, $A^{3a}$s may be the same or different;

$Y^1$ is a $C_1$ to $C_4$ haloalkyl group, a $C_1$ to $C_4$ alkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom;

m is an integer of 0 to 5, and when m is not less than 2, $Y^1$s may be the same or different;

Z is an oxygen atom or a sulfur atom; and

L is a leaving group.

In a fifth aspect of the present invention, there is provided a process for producing N-substituted-4-substituted-6-(substituted or unsubstituted) phenoxy-2-pyridine carboxamide or thiocarboxamide represented by the general formula (I-d), which process comprises reacting N-substituted-4-substituted-6-(substituted or unsubstituted) phenoxy-2-pyridine carboxamide represented by the general formula (VIII), having a hydroxyl group, an amino group, a (substituted or unsubstituted) alkylamino group or the like which is bonded to the N atom, with a compound represented by the general formula (VII-b).

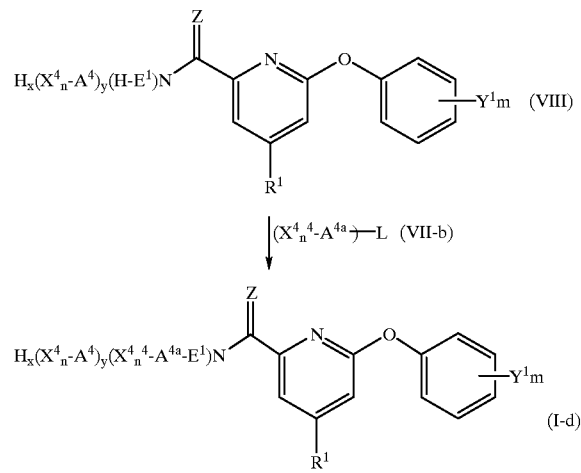

wherein $R^1$ is a $C_1$ to $C_4$ alkoxy group, a $C_1$ to $C_4$ alkylthio group, a $C_1$ to $C_4$ alkylamino group, a di($C_1$ to $C_4$ alkyl) amino group or a ($C_1$ to $C_4$ alkyl)($C_7$ to $C_8$ aralkyl)amino group;

$A^4$ may be substituted with $X^4$, and is a $C_1$ to $C_{10}$ alkyl group, a $C_3$ to $C_6$ alkenyl group, a $C_3$ to $C_6$ alkynyl group, a $C_3$ to $C_6$ cycloalkyl group, a phenyl group or an arylalkyl group (whose alkyl moiety has 1 to 3 carbon atoms) {wherein the chain-like hydrocarbon moiety of $A^4$ is constituted by a longest carbon chain as a main chain exclusive of a $C_1$ to $C_4$ alkyl group bonded as side chain to the main chain, and the $C_1$ to $C_4$ alkyl group as side chain is regarded as $X^4$};

$A^{4a}$ may be substituted with $X^4$, and is a $C_1$ to $C_{10}$ alkyl group, a $C_3$ to $C_6$ alkenyl group, a $C_3$ to $C_6$ alkynyl group, a $C_3$ to $C_6$ cycloalkyl group or an arylalkyl group (whose alkyl moiety has 1 to 3 carbon atoms) {wherein the chain-like hydrocarbon moiety of $A^{4a}$ is constituted by a longest carbon chain as a main chain exclusive of a side chain bonded to the main chain, and the side chain is regarded as $X^4$};

$E^1H$ is a hydroxyl group, an amino group or a $C_1$ to $C_{10}$ alkylamino group which may be substituted with $X^4$ {wherein the chain-like hydrocarbon moiety of $E^1$ is constituted by a longest carbon chain as a main chain exclusive of a $C_1$ to $C_4$ alkyl group bonded as side chain to the main chain, and the $C_1$ to $C_4$ alkyl group as side chain is regarded as $X^4$};

$X^4$ is a halogen atom, a $C_1$ to $C_4$ alkoxy group, a $C_1$ to $C_4$ alkylthio group, a $C_1$ to $C_4$ alkyl group (which is not bonded to terminal positions of $A^4$ and $A^{4a}$, when $A^4$ and $A^{4a}$ are a $C_1$ to $C_{10}$ alkyl group), a $C_3$ to $C_6$ cycloalkyl group, a $C_1$ to $C_4$ alkylamino group, a di($C_1$ to $C_4$ alkyl)amino group, a $C_1$ to $C_4$ alkylsulfonyl group, a $C_1$ to $C_4$ alkylsulfinyl group, a hydroxyl group, an amino group, a cyano group or a thiol group, wherein the alkyl moiety of $X^4$ may be substituted with halogen atom(s);

n and $n^4$ are 0 or an integer selected from numbers of hydrogen atoms of $A^4$ and $A^{4a}$, respectively, which may be substituted with $X^4$, and when n and $n^4$ are an integer of not less than 2, $X^4$s may be the same or different;

x is 0 or 1 and y is 0 or 1 with the proviso that the sum of x and y (x+y) is 1;

$Y^1$ is a $C_1$ to $C_4$ haloalkyl group, a $C_1$ to $C_4$ alkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom;

m is an integer of 0 to 5, and when m is not less than 2, $Y^1$s may be the same or different;

Z is an oxygen atom or a sulfur atom; and

L is a leaving group.

In a sixth aspect of the present invention, there is provided a process for producing N-substituted-4-substituted-6-(substituted or unsubstituted) phenoxy-2-pyridine carboxamide or thiocarboxamide represented by the general formula (I-e), which process comprises reacting N-substituted-4-substituted-6-(substituted or unsubstituted) phenoxy-2-pyridine carboxamide represented by the general formula (IX) and having a hydroxyl group, an amino group, a halogen-(substituted or unsubstituted) alkylamino group or a thiol group in substituents bonded to the N atom, with a compound represented by the general formula (VII-c).

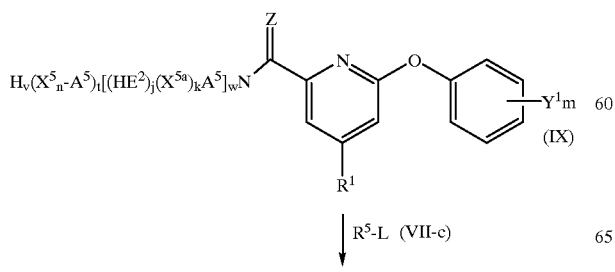

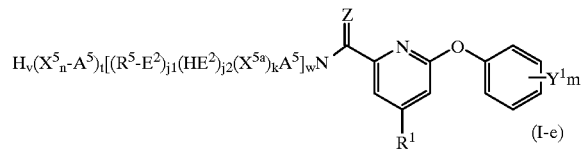

wherein $R^1$ is a $C_1$ to $C_4$ alkoxy group, a $C_1$ to $C_4$ alkylthio group, a $C_1$ to $C_4$ alkylamino group, a di($C_1$ to $C_4$ alkyl) amino group or a ($C_1$ to $C_4$ alkyl)($C_7$ to $C_8$ aralkyl)amino group;

$A^5$ may be substituted with $X^5$, and is a $C_1$ to $C_{10}$ alkyl group, a $C_2$ to $C_6$ alkenyl group, a $C_3$ to $C_6$ alkynyl group, a $C_3$ to $C_6$ cycloalkyl group, a $C_1$ to $C_{10}$ alkoxy group, a $C_3$ to $C_6$ alkenyloxy group, a $C_3$ to $C_6$ alkynyloxy group, a $C_1$ to $C_{10}$ alkylamino group, a di($C_1$ to $C_6$ alkyl)amino group, a phenyl group, a phenylamino group, an arylalkyl group (whose alkyl moiety has 1 to 3 carbon atoms), an arylalkyloxy group (whose alkyl moiety has 1 to 3 carbon atoms) or an arylalkylamino group (whose alkyl moiety has 1 to 3 carbon atoms) {wherein the chain-like hydrocarbon moiety of $A^5$ is constituted by a longest carbon chain as a main chain exclusive of a $C_1$ to $C_4$ alkyl group bonded as side chain to the main chain, and the $C_1$ to $C_4$ alkyl group as side chain is regarded as $X^5$};

$X^5$ is a halogen atom, a $C_1$ to $C_4$ alkoxy group, a $C_1$ to $C_4$ alkylthio group, a $C_1$ to $C_4$ alkyl group {which is not bonded to a terminal position of $A^5$, when $A^5$ is a $C_1$ to $C_{10}$ alkyl group, a $C_1$ to $C_{10}$ alkoxy group, a $C_1$ to $C_{10}$ alkylamino group or a di($C_1$ to $C_6$ alkyl)amino group}, a $C_3$ to $C_6$ cycloalkyl group, a $C_1$ to $C_4$ alkylamino group, a di($C_1$ to $C_4$ alkyl)amino group, a $C_1$ to $C_4$ alkylsulfonyl group, a $C_1$ to $C_4$ alkylsulfinyl group, a hydroxyl group, an amino group, a cyano group or a thiol group, wherein the alkyl moiety of $X^5$ may be further substituted with halogen atom(s);

$X^{5a}$ is a halogen atom, a $C_1$ to $C_4$ alkoxy group, a $C_1$ to $C_4$ alkylthio group, a $C_1$ to $C_4$ alkyl group {which is not bonded to a terminal position of $A^5$, when $A^5$ is a $C_1$ to $C_{10}$ alkyl group, a $C_1$ to $C_{10}$ alkoxy group, a $C_1$ to $C_{10}$ alkylamino group or a di($C_1$ to $C_6$ alkyl)amino group}, a $C_3$ to $C_6$ cycloalkyl group, a di($C_1$ to $C_4$ alkyl)amino group, a $C_1$ to $C_4$ alkylsulfonyl group, a $C_1$ to $C_4$ alkylsulfinyl group or a cyano group, wherein the alkyl moiety of $X^{5a}$ may be further substituted with halogen atom(s);

n is 0 or an integer selected from numbers of hydrogen atoms of $A^5$ which can be substituted with $X^5$;

when n is an integer of not less than 2, $X^5$s may be the same or different;

t is 0 or 1, v is 0 or 1 and w is 1 or 2 with the proviso that the sum of t and v (t+v) is 0 or 1 and the sum of t, v and w (t+v+w) is 2;

when w is 2 and t and w are 1, $A^5$s may be the same or different;

when w is 2 and $A^5$s are alkyl chains, the $A^5$s may be directly bonded together to form a ring, or the $A^5$s may be bonded to each other through an oxygen atom of the hydroxyl group or a nitrogen atom of the amino group or the $C_1$ to $C_4$ alkylamino group which groups are bonded to one of the $A^5$s, to form a ring;

$E^2H$ is a hydroxyl group, an amino group, a thiol group or a $C_1$ to $C_4$ alkylamino group which may be substituted with halogen atom(s);

$R^5$ a $C_1$ to $C_4$ alkyl group which may be substituted with a halogen atom;

j is an integer of not less than 1 and k is an integer of not less than 0 with the proviso that the sum of j and k (j+k) is 1 or an integer selected from numbers of hydrogen atoms of $A^5$ which can be substituted with $X^5$;

when j is not less than 2, $E^2Hs$ may be the same or different;

when k is not less than 2, $X^{5a}s$ may be the same or different;

$j^1$ is an integer of not less than 1 and $j^2$ is an integer of not less than 0 with the proviso that the sum of $j^1$ and $j^2$ ($j^1+j^2$) is j;

$Y^1$ is a $C_1$ to $C_4$ haloalkyl group, a $C_1$ to $C_4$ alkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom;

m is an integer of 0 to 5, and when m is not less than 2, $Y^1s$ may be the same or different;

Z is an oxygen atom or a sulfur atom; and

L is a leaving group.

In a seventh aspect of the present invention, there is provided a process for producing N-(substituted or unsubstituted)-4-substituted-6-(substituted or unsubstituted) phenoxy-2-pyridine carboxamide or thiocarboxamide represented by the general formula (I-f), which process comprises reacting N-(substituted or unsubstituted)-4-substituted-6-halogeno-2-pyridine carboxamide or thiocarboxamide represented by the general formula (X) with (substituted or unsubstituted) phenol represented by the general formula (XI) under basic condition.

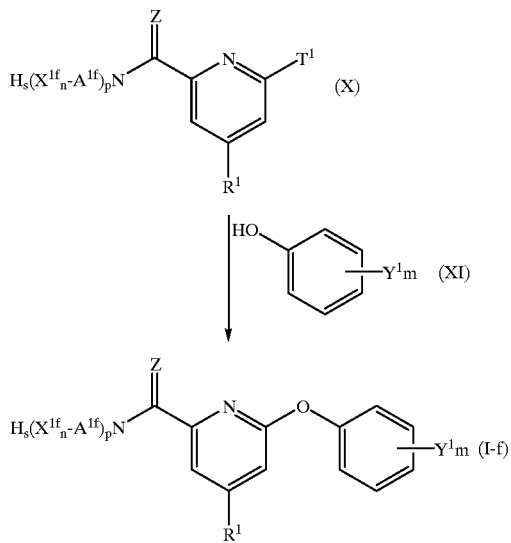

wherein $R^1$ is a $C_1$ to $C_4$ alkoxy group, a $C_1$ to $C_4$ alkylthio group, a $C_1$ to $C_4$ alkylamino group, a di($C_1$ to $C_4$ alkyl) amino group or a ($C_1$ to $C_4$ alkyl)($C_7$ to $C_8$ aralkyl)amino group;

$A^{1f}$ may be substituted with $X^{1f}$, and is a $C_1$ to $C_{10}$ alkyl group, a $C_2$ to $C_6$ alkenyl group, a $C_3$ to $C_6$ alkynyl group, a $C_3$ to $C_6$ cycloalkyl group, a $C_1$ to $C_{10}$ alkoxy group, a $C_3$ to $C_6$ alkenyloxy group, a $C_3$ to $C_6$ alkynyloxy group, a $C_1$ to $C_{10}$ alkylamino group, a di($C_1$ to $C_6$ alkyl)amino group, a phenyl group, a phenylamino group, an arylalkyl group (whose alkyl moiety has 1 to 3 carbon atoms), an arylalkyloxy group (whose alkyl moiety has 1 to 3 carbon atoms), an arylalkylamino group (whose alkyl moiety has 1 to 3 carbon atoms) or a hydroxyl group {wherein the chain-like hydrocarbon moiety of Alf is constituted by a longest carbon chain as a main chain exclusive of a $C_1$ to $C_4$ alkyl group bonded as side chain to the main chain, and the $C_1$ to $C_4$ alkyl group as side chain is regarded as $X^{1f}$};

$X^{1f}$ is a halogen atom, a $C_1$ to $C_4$ alkoxy group, a $C_1$ to $C_4$ alkylthio group, a $C_1$ to $C_4$ alkyl group {which is not bonded to a terminal position of $A^{1f}$, when $A^{1f}$ is a $C_1$ to $C_{10}$ alkyl group, a $C_1$ to $C_{10}$ alkoxy group, a $C_1$ to $C_{10}$ alkylamino group or a di($C_1$ to $C_6$ alkyl)amino group}, a $C_3$ to $C_6$ cycloalkyl group, a $C_1$ to $C_4$ alkylcarbonyl group, a $C_1$ to $C_4$ alkylamino group, a di($C_1$ to $C_4$ alkyl)amino group, a $C_1$ to $C_4$ alkylsulfonyl group, a $C_1$ to $C_4$ alkylsulfinyl group, a hydroxyl group, an amino group, a cyano group or a thiol group, wherein the alkyl moiety of $X^{1f}$ may be further substituted with halogen atom(s);

n is 0 or an integer selected from numbers of hydrogen atoms of $A^{1f}$ which may be substituted with $X^{1f}$, and when n is an integer of not less than 2, $X^{1f}s$ may be the same or different;

p and s are an integer of 0 to 2 with the proviso that the sum of p and s (p+s) is 2;

when p is 2, $A^{1f}s$ may be the same or different;

when p is 2 and $A^{1f}s$ are alkyl chains, the $A^{1f}s$ may be directly bonded together to form a ring, or the $A^{1f}s$ may be bonded to each other through an oxygen atom of the hydroxyl group or a nitrogen atom of the amino group or the $C_1$ to $C_4$ alkylamino group which groups are bonded to one of the $A^{1f}s$, to form a ring;

$Y^1$ is a $C_1$ to $C_4$ haloalkyl group, a $C_1$ to $C_4$ alkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom;

m is an integer of 0 to 5, and when m is not less than 2, $Y^1s$ may be the same or different;

Z is an oxygen atom or a sulfur atom; and $T^1$ is a halogen atom.

In an eighth aspect of the present invention, there is provided a herbicide containing as an effective ingredient N-(substituted or unsubstituted)-4-substituted-6-(substituted or unsubstituted) phenoxy-2-pyridine carboxamide or thiocarboxamide represented by the above-mentioned general formula (I).

The present invention will be described in detail below.

First, N-(substituted or unsubstituted)-4-substituted-6-(substituted or unsubstituted) phenoxy-2-pyridine carboxamide or thiocarboxamide represented by the above-mentioned general formula (I) (hereinafter referred to merely as "the present compound (I)"), is explained.

The definitions and the detailed contents of respective symbols ($R^1, A^1, X^1, Y^1, Z, s, p$ and m) used for the present compound (I) are described below.

Examples of the $C_1$ to $C_4$ alkoxy groups as $R^1$ may include methoxy, ethoxy, (1-methyl)ethoxy (identical to isopropoxy) or the like. Examples of the $C_1$ to $C_4$ alkylthio groups as $R^1$ may include methylthio, ethylthio or the like. Examples of the $C_1$ to $C_4$ alkylamino groups as $R^1$ may include methylamino, ethylamino or the like. Examples of the di($C_1$ to $C_4$ alkyl) amino groups as $R^1$ may include dimethylamino, ethylmethylamino or the like. Examples of the ($C_1$ to $C_4$ alkyl)($C_7$ to $C_8$ aralkyl)amino groups as $R^1$ (wherein the $C_7$ to $C_8$ aralkyl may include branched groups such as 1-phenylethyl) may include methyl(phenylmethyl) amino, ethyl(phenylmethyl)amino or the like.

Among the above-defined examples, preferred groups as $R^1$ are methoxy, ethoxy, methylthio, ethylthio, methylamino, ethylamino, dimethylamino, diethylamino and methyl (phenylmethyl)amino.

Among them, more preferred groups as $R^1$ are methoxy, methylthio, methylamino and dimethylamino.

The above-specified contents with respect to $R^1$ are common to specific contents of $R^2$ and $R^3$ within the scope of definitions thereof.

Next, $A^1$ is explained below.

The chain-like hydrocarbon moiety of $A^1$ is constituted by a longest carbon chain as a main chain exclusive of a $C_1$ to $C_4$ alkyl group bonded as a side chain to the main chain, and the $C_1$ to $C_4$ alkyl group as a side chain is regarded as substituents $X^1$.

That is, with respect to $C_1$ to $C^{10}$ alkyl group, the longest carbon chain thereof is regarded as $A^1$, and the groups bonded thereto are regarded as substituents. Accordingly, in the case of isopropyl group, an ethyl group is regarded as $A^1$ and a methyl group is regarded as a substituent bonded to the 1-position of the ethyl group. Similarly, in the case of t-butyl group, an ethyl group is regarded as $A^1$, and two methyl groups are regarded as substituents bonded to the 1-position thereof.

With respect to the $C_2$ to $C_6$ alkenyl group, the carbon chain extending from the carbon atom bonded to a nitrogen atom of 2-CZN of pyridine up to the double bond located at the furthest position therefrom, is regarded as $A^1$. The $C_1$ to $C_4$ alkyl group bonded as side chain to $A^1$ is regarded as $X^1$.

With respect to the $C_3$ to $C_6$ alkynyl group, the carbon chain extending from the carbon atom bonded to a nitrogen atom of 2-CZN of pyridine up to the triple bond located at the furthest position therefrom, is regarded as $A^1$. The $C_1$ to $C_4$ alkyl group bonded as side chain to $A^1$ is regarded as $X^1$.

In the case where both the double and triple bonds are contained in $A^1$, the carbon chain extending from the 1-position up to the multiple bond located at the furthest position therefrom, is regarded as $A^1$. The $C_1$ to $C_4$ alkyl group bonded as a side chain to $A^1$ is regarded as $X^1$.

The $C_1$ to $C_4$ alkyl group bonded as a side chain to $A^1$ may be substituted with halogen atom(s) similarly to those bonded to the other positions.

In association with the above definition of $A^1$, in the case where $A^1$ is a $C_1$ to $C_{10}$ alkyl group, a $C_1$ to $C_{10}$ alkoxy group, a $C_1$ to $C_{10}$ alkylamino group or a di($C_1$ to $C_6$ alkyl)amino group, the substituent groups $X^1$ are not bonded to the terminal position of $A^1$.

The above-mentioned regularities between $A^1$ and $X^1$ are commonly used within the scopes of respective definitions of $A^2$ and $X^2$; $A^{1b}$ and $X^{1b}$; $A^3$ and $X^3$; $A^{3a}$ and $X^3$; $A^4$ and $X^4$; $A^{4a}$ and $X^4$; $E^1$, $A^{4a}$ and $X^4$; $A^5$ and $X^5$, $A^5$ and $X^{5a}$; $A^5$ and $E^2$; $A^5$, $E^2$ and $R^5$; and $A^{1f}$ and $X^{1f}$.

Specific examples of $A^1$ may include the following substituents.

As the $C_1$ to $C_{10}$ alkyl groups, a $C_1$ to $C_6$ alkyl group is preferred, and there may be usually exemplified methyl group, ethyl group, propyl group, butyl group, pentyl group, hexyl group or the like. Further, as the $C_2$ to $C_6$ alkenyl groups, there may be usually exemplified vinyl group, 2-propenyl group or the like. As the $C_3$ to $C_6$ alkynyl groups, there may be exemplified 2-propynyl group or the like. As the $C_3$ to $C_6$ cycloalkyl groups, there may be exemplified cyclopropyl group, cyclobutyl group, cyclopentyl group, cyclohexyl group or the like. As the $C_1$ to $C_{10}$ alkoxy groups, a $C_1$ to $C_6$ alkoxy group is preferred, and there may be usually exemplified methoxy group, ethoxy group, propoxy group, butoxy group or the like. Further, as the $C_3$ to $C_6$ alkenyloxy groups, there may be exemplified 2-propenyloxy group or the like. As the $C_3$ to $C_6$ alkynyloxy groups, there may be exemplified 2-propynyloxy group or the like. As the $C_1$ to $C_{10}$ alkylamino groups, $C_1$ to $C_6$ alkylamino groups are preferred, and there may be usually exemplified methylamino group, ethylamino group, propylamino group, butylamino group or the like. In addition, as the di($C_1$ to $C_6$ alkyl)amino groups, there may be exemplified dimethylamino, diethylamino or the like. As the arylalkyl groups (whose alkyl moiety has 1 to 3 carbon atoms), there may be exemplified phenylmethyl group or the like. As the arylalkyloxy groups (whose alkyl moiety has 1 to 3 carbon atoms), there may be exemplified phenylmethyloxy group or the like. As the arylalkylamino groups (whose alkyl moiety has 1 to 3 carbon atoms), there may be exemplified phenylmethylamino group or the like.

As the $A^1$, there may also be exemplified a hydroxyl group, an amino group, a phenyl group or a phenylamino group.

The specified contents with respect to the $A^1$ are common to specific contents of $A^2$, $A^{1b}$, $A^3$, $A^{3a}$, $A^4$, $A^{4a}$, $E^1H$, $E^1A^{4a}$, $A^5$ and $A^{1f}$ within the scopes of respective definitions thereof.

Specific examples of $X^1$ may include the following substituents.

As the halogen atoms, there may be exemplified fluorine atom, chlorine atom, bromine atom or the like. As the $C_1$ to $C_4$ alkyl groups, there may be exemplified methyl group, ethyl group, (1-methyl)ethyl group or the like. As the $C_3$ to $C_6$ cycloalkyl groups, there may be exemplified cyclopropyl group, cyclobutyl group, cyclopentyl group, cyclohexyl group or the like. As the $C_1$ to $C_4$ alkoxy groups, there may be exemplified methoxy group, ethoxy group, (1-methyl)ethoxy group or the like. As the $C_1$ to $C_4$ alkylthio groups, there may be exemplified methylthio group, ethylthio group, (1-methyl)ethylthio group or the like. As the $C_1$ to $C_4$ alkylsulfonyl groups, there may be exemplified methylsulfonyl group, ethylsulfonyl group or the like. As the $C_1$ to $C_4$ alkylsulfinyl groups, there may be exemplified methylsulfinyl group, ethylsulfinyl group or the like. As the $C_1$ to $C_4$ alkylcarbonyl groups, there may be exemplified methylcarbonyl group, ethylcarbonyl group or the like. Furthermore, examples of $X^1$ may also include a hydroxyl group, an amino group, a cyano group, a thiol group or the like.

As the halogen atoms which can be further substituted for these alkyl moieties including cycloalkyl groups, there may be exemplified fluorine atom, chlorine atom, bromine atom or the like. The number of these halogen atoms bonded to the alkyl moieties is usually 1 to 7, preferably 1 to 5. Examples of the halogen-substituted substituents $X^1$ may include trifluoromethyl group, 2-fluoroethyl group, 2,2,2-trifluoroethyl group, 2,2,3,3,3-pentafluoropropyl group, 2-chloroethyl group, 2-bromoethyl group, 3-chloropropyl group, 2-fluoroethoxy group, 2,2,2-trifluoroethoxy group, 2-chloroethoxy group, 2-bromoethoxy group, 3-chloropropoxy group, 2-fluoroethylthio group, 2,2,2-trifluoroethylthio group, 2-chloroethylthio group, 2-bromoethylthio group, 3-chloropropylthio group, 2-fluoroethylsulfonyl group, 2,2,2-trifluoroethylsulfonyl group, trifluoromethylsulfonyl group, 2-chloroethylsulfonyl group, 2-bromoethylsulfonyl group, 3-chloropropylsulfonyl group, 2-fluoroethylsulfinyl group, 2,2,2-trifluoroethylsulfinyl group, trifluoromethylsulfinyl group, 2-chloroethylsulfinyl group, 2-bromoethylsulfinyl group, 3-chloropropylsulfinyl group, trifluoroacetyl group, 2,2-dichlorocyclopropyl group or the like.

The specified contents described with respect to $X^1$ are common to specific contents of $X^2$, $X^{1b}$, $X^3$, $X^4$, $X^5$, $X^{5a}$, $R^5E^2$ and $X^{1f}$ within the scopes of respective definitions thereof.

The integer n is usually in the range of 0 (indicating that no $X^1$ is substituted) to 15, preferably 0 to 10, more preferably 0 to 7. The above-specified range of n is explained in more detail with respect to the combination of $A^1$ and $X^1$.

In the combination of $A^1$ {$C_1$ to $C_{10}$ alkyl group, $C_2$ to $C_6$ alkenyl group, $C_3$ to $C_6$ alkynyl group, $C_1$ to $C_{10}$ alkoxy group, $C_3$ to $C_6$ alkenyloxy group, $C_3$ to $C_6$ alkynyloxy group, $C_1$ to $C_{10}$ alkylamino group or di($C_1$ to $C_6$ alkyl) amino group} and $X^1$, the range of n is varied depending upon kind of $X^1$ as follows.

In the case where $X^1$ is a fluorine atom, n is usually 1 to 15, preferably 1 to 10, more preferably 1 to 7.

In the case where $X^1$ is a halogen atom other than fluorine atom, n is usually 1 to 5, preferably 1 to 3, more preferably 1 to 2.

In the case where $X^1$ is an alkyl group, n is usually 1 to 7, preferably 1 to 5, more preferably 1 to 3.

In the case where $X^1$ is a substituent other than halogen atom or alkyl group, n is usually 1 to 3, preferably 1 to 2.

In the case where $A^1$ is a $C_3$ to $C_6$ cycloalkyl group, a phenyl group, a phenylamino group, an arylalkyl group (whose alkyl moiety has 1 to 3 carbon atoms), an arylalkyloxy group (whose alkyl moiety has 1 to 3 carbon atoms) or an arylalkylamino group (whose alkyl moiety has 1 to 3 carbon atoms), the integer n is usually 1 to 5, preferably 1 to 3 irrespective of kind of $X^1$.

The above-specified contents with respect to the integer n are common to specific contents of $n^3$, $n^4$, j, k, $j^1$, $j^2$ and $j^3$ within the scopes of respective definitions thereof.

The specific examples of $A^1$—$X^1_n$ may include the following combinations.

In the case where n is 0, there may be exemplified:
- $C_1$ to $C_{10}$ alkyl groups such as methyl, ethyl, propyl, butyl, pentyl, hexyl, heptyl, octyl, nonyl, decyl or the like;
- $C_2$ to $C_6$ alkenyl groups such as vinyl, allyl, 1,3-butadienyl or the like;
- $C_3$ to $C_6$ alkynyl groups such as 2-propynyl, 2-pentene-4-ynyl or the like;
- $C_3$ to $C_6$ cycloalkyl groups such as cyclopropyl, cyclobutyl, cyclopentyl, cyclohexyl or the like;
- $C_1$ to $C_{10}$ alkoxy groups such as methoxy, ethoxy, propoxy, butoxy, pentyloxy, hexyloxy, heptyloxy, octyloxy, nonyloxy or the like;
- $C_3$ to $C_6$ alkenyloxy groups such as allyloxy, 1,3-butadienyloxy or the like;
- $C_3$ to $C_6$ alkynyloxy groups such as 2-propynyloxy, 2-pentene-4-ynyloxy or the like;
- $C_1$ to $C_{10}$ alkylamino groups such as methylamino, ethylamino, propylamino, butylamino, pentylamino, hexylamino, heptylamino, octylamino or the like;
- di($C_1$ to $C_6$ alkyl)amino groups such as dimethylamino, diethylamino, dipropylamino, dibutylamino, methyl(ethyl)amino, methyl(propyl)amino, ethyl(propyl)amino or the like;
- phenyl group;
- phenylamino group;
- phenyl($C_1$ to $C_3$ alkyl) groups {indicating such arylalkyl groups whose alkyl moiety has 1 to 3 carbon atoms and whose aryl group is phenyl} such as phenylmethyl, phenylethyl, phenylpropyl or the like;
- phenyl($C_1$ to $C_3$ alkyl)oxy groups {indicating such arylalkyloxy groups whose alkyl moiety has 1 to 3 carbon atoms and whose aryl group is phenyl} such as phenylmethyloxy, phenylethyloxy, phenylpropyloxy or the like;
- phenyl($C_1$ to $C_3$ alkyl)amino groups {indicating such arylalkylamino groups whose alkyl moiety has 1 to 3 carbon atoms and whose aryl group is phenyl} such as phenylamino, phenylmethylamino, phenylethylamino, phenylpropylamino or the like;
- amino group;
- hydroxyl group; or the like.

In the case where $X^1$ is alkyl and n is 1 to 2:
- $C_3$ to $C_{12}$ alkyl groups such as 1-methylethyl, 1-methylpropyl, 1-methylbutyl, 2-methylpropyl, 2-methylbutyl, 1-ethylpropyl, 1,1-dimethylethyl, 1,1-dimethylpropyl or the like;
- $C_3$ to $C_9$ alkenyl groups such as 1-methylethenyl, 1-methyl-2-propenyl, 2-methyl-1-2-propenyl, 3,3-dimethylpropenyl, 2,3-dimethylpropenyl or the like;
- $C_4$ to $C_9$ alkynyl groups such as 3-methylpropynyl, 3-ethylpropynyl, 1-methylpropynyl, 1,3-dimethylpropynyl or the like;
- $C_4$ to $C_9$ cycloalkyl groups such as 2-imethylcyclopropyl, 2,2-dimethylcyclopropyl, 2-methylcyclobutyl, 2-methylcyclopentyl or the like;
- $C_3$ to $C_{12}$ alkoxy groups such as 1-methylethoxy, 1-methylpropoxy, 1-methylbutoxy, 2-methylpropoxy, 2-ethylpropoxy, 1-ethylpropoxy, 1,1-dimethylpropoxy or the like;
- $C_4$ to $C_9$ alkenyloxy groups such as 1-methyl-2-propenyloxy, 2-methyl-2-propenyloxy, 3,3-dimethylpropenyloxy, 2,3-dimethylpropenyloxy or the like;
- $C_4$ to $C_9$ alkynyloxy groups such as 3-methylpropynyloxy, 3-ethylpropynyloxy, 1-methylpropynyloxy, 1,3-dimethylpropynyloxy or the like;
- $C_3$ to $C_{14}$ alkylamino groups such as 1,1-dimethylehtylamino, 2-methylpropylamino, 2-methylbutylamino, 1,1-dimethylbutylamino, 2-ethylbutylamino or the like;
- ($C_1$ to $C_4$ alkyl)($C_3$ to $C_6$ alkyl)amino groups such as methyl(2-methylethyl)amino, ethyl(2-methylethyl)amino, propyl(2-methylethyl)amino, di(2-methylethyl)amino or the like;
- $C_1$ to $C_4$ alkylphenyl groups such as 2-methylphenyl, 3-methylphenyl, 4-methylphenyl, 2-ethylphenyl, 3-ethylphenyl, 4-ethylphenyl, 3,4-dimethylphenyl, 2,4-dimethylphenyl or the like;
- $C_1$ to $C_4$ alkylphenylamino groups such as 2-methylphenylamino, 3-methylphenylamino, 4-methylphenylamino, 2-ethylphenylamino, 3-ethylphenylamino, 4-ethylphenylamino, 3,4-dimethylphenylamino, 2,4-dimethylphenylamino or the like;
- ($C_1$ to $C_4$ alkylphenyl) $C_1$ to $C_3$ alkyl groups such as (2-methylphenyl)methyl, (3-methylphenyl)methyl, (4-methylphenyl)methyl, 1-methyl-1-(4-methylphenyl)methyl {identical to 2-(4-methylphenyl)ethyl}, 2-methyl-2-(4-methylphenyl)ethyl, (2-ehtylphenyl)methyl, (3-ehtylphenyl)methyl, (4-ehtylphenyl)methyl, (3,4-dimethylphenyl)methyl, (2,4-dimethylphenyl)methyl or the like;

($C_1$ to $C_4$ alkylphenyl) $C_1$ to $C_3$ alkyloxy groups such as (2-methylphenyl)methyloxy, (3-methylphenyl)methyloxy, (4-methylphenyl)methyloxy, 1-methyl-1-(4-methylphenyl)methyloxy {identical to 2-(4-methylphenyl)ethyloxy}, 2-methyl-2-(4-methylphenyl)ethyloxy, (2-ehtylphenyl)methyloxy, (3-ehtylphenyl)methyloxy, (4-ehtylphenyl)methyloxy, (3,4-dimethylphenyl)methyloxy, (2,4-dimethylphenyl)methyloxy or the like;

($C_1$ to $C_4$ alkylphenyl) $C_1$ to $C_3$ alkylamino groups such as (2-methylphenyl)methylamino, (3-methylphenyl)methylamino, (4-methylphenyl)methylamino, 1-methyl-1-(4-methylphenyl)methylamino {identical to 2-(4-methylphenyl)ethylamino}, 2-methyl-2-(4-methylphenyl)ethylamino, (2-ehtylphenyl)methylamino, (3-ehtylphenyl)methylamino, (4-ehtylphenyl)methylamino, (3,4-dimethylphenyl)methylamino, (2,4-dimethylphenyl)methylamino or the like.

In the case where $X^1$ is a halogen atom and n is 1 to 7:

halogen-substituted $C_1$ to $C_{10}$ alkyl groups such as trifluoromethyl, difluoromethyl, 2-fluoroethyl, 4-fluorobutyl, 2-bromo-2,2-difluoroethyl, 2,2,2-trifluroethyl, 3,3,3-trifluoropropyl, 2,2,3,3,3-pentafluoropropyl, 2,2,3,3,4,4,4-heptafluorobutyl, trichloromethyl, chloromethyl, 2-chloroethyl, 3-chloropropyl, 2,2,2-trichloroethyl, 3,3,3-trichloropropyl, tribromomethyl, bromomethyl, 2-bromoethyl, 3-bromopropyl, 2-iodoethyl, 3-iodopropyl or the like;

halogen-substituted $C_2$ to $C_6$ alkenyl groups such as 2,2-dichloroethenyl, 2-chloro-2-propenyl, 3,3-dichloro-2-propenyl, 3-chloro-2-propenyl, 2,3-dichloro-2-propenyl, 2,2-difluoroethenyl, 2-fluoro-2-propenyl, 3,3-difluoro-2-propenyl, 3-fluoro-2-propenyl, 2,3-difluoro-2-propenyl, 2,2-dibromoethenyl, 2-bromo-2-propenyl, 3,3-dibromo-2-propenyl, 3-bromo-2-propenyl, 2,3-dibromo-2-propenyl or the like;

halogen-substituted $C_3$ to $C_6$ alkynyl groups such as 3-chloropropynyl, 3-fluoropropynyl, 1-bromopropynyl or the like;

halogen-substituted $C_1$ to $C_6$ cycloalkyl groups such as 2-chlorocyclopropyl, 2,2-dichloropropyl, 2,2,3,3-tetrachloropropyl, 2-fluorocyclopropyl, 2,2-difluorocyclopropyl, 2,2,3,3-tetrafluoropropyl or the like;

halogen-substituted $C_1$ to $C_{10}$ alkoxy groups such as trifluoromethoxy, difluoromethoxy, 2-fluoroethoxy, 4-fluorobutoxy, 2-bromo-2,2-difluoroethoxy, 2,2,2-trifluoroethoxy, 3,3,3-trifluoropropoxy, 2,2,3,3,3-pentafluoropropoxy, 2,2,3,3,4,4,4-heptafluorobutoxy, 2-chloroethoxy, 3-chloropropoxy, 2,2,2-trichloroethoxy, 3,3,3-trichloropropoxy, 2-bromoethoxy, 3-bromopropoxy, 2-iodoethoxy, 3-iodopropoxy or the like;

halogen-substituted $C_3$ to $C_6$ alkenyloxy groups such as 2-chloro-2-propenyloxy, 3,3-dichloro-2-propenyloxy, 2,3-dichloro-2-propenyloxy, 2,2-dichloro-2-propenyloxy, 2-fluoro-2-propenyloxy, 3,3-difluoro-2-propenyloxy, 3-fluoro-2-propenyloxy, 2,3-difluoro-2-propenyloxy, 2-bromo-2-propenyloxy, 3,3-dibromo-2-propenyloxy, 3-bromo-2-propenyloxy, 2,3-dibromo-2-propenyloxy or the like;

halogen-substituted $C_3$ to $C_6$ alkynyloxy groups such as 3-chloropropynyloxy, 3-fluoropropynyloxy, 1-bromopropynyloxy or the like;

halogen-substituted $C_1$ to $C_{10}$ alkylamino groups such as trifluoromethylamino, difluoromethylamino, 2-fluoroethylamino, 4-fluorobutylamino, 2-bromo-2,2-difluoroethylamino, 2,2,2-trifluoroethylamino, 3,3,3-trifluoropropylamino, 2,2,3,3,3-pentafluoropropylamino, 2,2,3,3,4,4,4-heptafluorobutylamino, trichloromethylamino, 2-chloroethylamino, 3-chloropropylamino, 2,2,2-trichloroethylamino, 3,3,3-trichloropropylamino, 2-bromoethylamino, 3-bromopropylamino, 2-iodoethylamino, 3-iodopropylamino or the like;

{halogen-substituted di($C_1$ to $C_4$ alkyl)}amino groups such as trifluoromethyl(methyl)amino, difluoromethyl(methyl)amino, (2-fluoroethyl)(methyl)amino, (4-fluorobutyl)(methyl)amino, (2-bromo-2,2-difluoroethyl)(methyl)amino, (2,2,2-trifluoroethyl)(methyl)amino, (3,3,3-trifluoropropyl)(methyl)amino, ( 2,2,3,3,3-pentafluoropropyl)(methyl)amino, (2,2,3,3,4,4,4-heptafluorobutyl)(methyl)amino, (2-chloroethyl)(methyl)amino, (3-chloropropyl)(methyl)amino, (2,2,2-trichloroethyl)(methyl)amino, (3,3,3-trichloropropyl)(methyl)amino, (2-bromoethyl)(methyl)amino, (3-bromopropyl)(methyl)amino, (2-iodoethyl)(methyl)amino, (3-iodopropyl)(methyl)amino, trifluoromethyl(ethyl)amino, difluoromethyl(ethyl)amino, (2-fluoroethyl)(ethyl)amino, di(2-fluoroethyl)amino, di(2-chloroethyl)amino, (4-fluorobutyl)(ethyl)amino, (2-bromo-2,2-difluoroethyl)(ethyl)amino, (2,2,2-trifluoroethyl)(ethyl)amino, (3,3,3-trifluoropropyl)(ethyl)amino, (2,2,3,3,3-pentafluoropropyl)(ethyl)amino, (2,2,3,3,4,4,4-heptafluorobutyl)(ethyl)amino, (2,2,2-trichloroethyl)(ethyl)amino, chloromethyl(ethyl)amino, (2-chloroethyl)(ethyl)amino, 3-chloropropyl(ethyl)amino, (2,2,2-trichloroethyl)(ethyl)amino, (3,3,3-trichloropropyl)(ethyl)amino, (2-bromoethyl)(ethyl)amino, (3-bromopropyl)(ethyl)amino, (2-iodoethyl)(ethyl)amino, (3-iodopropyl)(ethyl)amino or the like;

halogen-substituted phenyl groups such as 2-chlorophenyl, 3-chlorophenyl, 4-chlorophenyl, 3,4-dichlorophenyl, 2,4-dichlorophenyl, 2-fluorophenyl, 3-fluorophenyl, 4-fluorophenyl, 3,4-difluorophenyl, 2,4-difluorophenyl, 2-bromophenyl, 3-bromophenyl, 4-bromophenyl, 3,4-dibromophenyl, 2,4-dibromophenyl, 2-iodophenyl, 3-iodophenyl or the like;

halogen-substituted phenylamino groups such as 2-chlorophenylamino, 3-chlorophenylamino, 4-chlorophenylamino, 3,4-dichlorophenylamino, 2,4-dichlorophenylamino, 2-fluorophenylamino, 3-fluorophenylamino, 4-fluorophenylamino, 3,4-difluorophenylamino, 2,4-difluorophenylamino, 2-bromophenylamino, 3-bromophenylamino, 4-bromophenylamino, 3,4-dibromophenylamino, 2,4-dibromophenylamino, 2-iodophenylamino, 3-iodophenylamino or the like;

(halogen-substituted phenyl) $C_1$ to $C_3$ alkyl groups such as (2-chlorophenyl)methyl, (3-chlorophenyl)methyl, (4-chlorophenyl)methyl, 2-(3-chlorophenyl)ethyl, 2-(4-chlorophenyl)ethyl, (2,4-dichlorophenyl)methyl, 2-(3-fluorophenyl)ethyl, 2-(4-fluorophenyl)ethyl, 1-(4-fluorophenyl)ethyl or the like;

(halogen-substituted phenyl) $C_1$ to $C_3$ alkyloxy groups such as (2-chlorophenyl)methyloxy, (3-chlorophenyl)methyloxy, (4-chlorophenyl)ethyloxy, 2-(3-chlorophenyl)ethyloxy, 2-(4-chlorophenyl)ethyloxy, (2,4-dichlorophenyl)methyloxy, 2-(3-fluorophenyl)ethyloxy, 2-(4-fluorophenyl)ethyloxy, 1-(4-fluorophenyl)ethyloxy or the like; and (halogen-substituted phenyl) $C_1$ to $C_3$ alkylamino groups such as (2-chlorophenyl)methylamino, (3-chlorophenyl)methylamino, (4-chlorophenyl)methylamino, 2-(3-chlorophenyl)ethylamino, 2-(4-chlorophenyl)ethylamino, (2,4-dichlorophenyl)methylamino, 2-(3-fluorophenyl)ethylamino, 2-(4-fluorophenyl)ethylamino, 1-(4-fluorophenyl)ethylamino or the like.

In the case where $X^1$ is an alkoxy group and n is 1 to 2:

$C_1$ to $C_4$ alkoxy-substituted $C_1$ to $C_{10}$ alkyl groups such as methoxymethyl, ethoxymethyl, propoxymethyl, 2-(methoxy)ethyl, 1-(methoxy)ethyl, 1-(methoxy)propyl, 2-(ethoxy)ethyl, 3-(methoxy)propyl, 4-(methoxy)butyl, 2-(methoxy)propyl, 2-(ethoxy)propyl, 1-(ethoxy)propyl, 2,3-di(methoxy)propyl or the like;

$C_1$ to $C_4$ alkoxy-substituted $C_1$ to $C_{10}$ alkoxy groups such as methoxymethoxy, ethoxymethoxy, propoxymethoxy, 2-(methoxy)ethoxy, 2-(ethoxy)ethoxy, 3-(methoxy)propoxy, 4-(methoxy)butoxy, 2-(methoxy)propoxy, 2-(ethoxy)propoxy, 1-(methoxy)propoxy, 1-(ethoxy)propoxy, 2,3-di(methoxy)propoxy or the like;

$C_1$ to $C_4$ alkoxy-substituted $C_1$ to $C_{10}$ alkylamino groups such as 2-(methoxy)ethylamino, 3-(methoxy)propylamino, 2-(ethoxy)ethylamino, 2-(propoxy)ethylamino, 1-(ethoxy)ethylamino, 1-(methoxy)propylamino, 4-(methoxy)butylamino, 2-(methoxy)propylamino, 2-(ethoxy)propylamino, 1-(ethoxy)propylamino or the like;

{$C_1$ to $C_4$ alkoxy-substituted di($C_1$ to $C_6$ alkyl)}amino groups such as methyl(methoxymethyl)amino, ethyl(2-methoxyethyl)amino, methyl(2-ethoxypropyl)amino, di(2-ethoxyethyl)amino, di(ethoxymethyl)amino or the like;

$C_1$ to $C_4$ alkoxy-substituted phenyl groups such as 2-methoxyphenyl, 3-methoxyphenyl, 4-methoxyphenyl, 2-ethoxyphenyl, 3-ethoxyphenyl, 4-ethoxyphenyl, 3,4-dimethoxyphenyl, 2,4-dimethoxyphenyl or the like;

($C_1$ to $C_4$ alkoxy-substituted phenyl)amino groups such as 2-methoxyphenylamino, 3-methoxyphenylamino, 4-methoxyphenylamino, 2-ethoxyphenylamino, 3-ethoxyphenylamino, 4-ethoxyphenylamino, 3,4-dimethoxyphenylamino, 2,4-dimethoxyphenylamino or the like;

($C_1$ to $C_4$ alkoxy-substituted phenyl) $C_1$ to $C_3$ alkyl groups such as 2-(2-methoxyphenyl)ethyl, 2-(3-methoxyphenyl)ethyl, 2-(4-methoxyphenyl)ethyl, 1-(4-methoxyphenyl)ethyl, 2-(4-methoxyphenyl)propyl, (4-ethoxyphenyl)methyl, (3,4-dimethoxyphenyl)methyl, (2,4-dimethoxyphenyl)methyl or the like;

($C_1$ to $C_4$ alkoxy-substituted phenyl) $C_1$ to $C_3$ alkyloxy groups such as 2-(2-methoxyphenyl)ethyloxy, 2-(3-methoxyphenyl)ethyloxy, 2-(4-methoxyphenyl)ethyloxy, 1-(4-methoxyphenyl)ethyloxy, 2-(4-methoxyphenyl)propyloxy, (4-ethoxyphenyl)methyloxy, (3,4-dimethoxyphenyl)methyloxy, (2,4-dimethoxyphenyl)methyloxy or the like; and ($C_1$ to $C_4$ alkoxy-substituted phenyl) $C_1$ to $C_3$ alkylamino groups such as 2-(2-methoxyphenyl)ethylamino, 2-(3-methoxyphenyl)ethylamino, 2-(4-methoxyphenyl)ethylamino, 1-(4-methoxyphenyl)ethylamino, 2-(4-methoxyphenyl)propylamino, (4-ethoxyphenyl)methylamino, (3,4-dimethoxyphenyl)methylamino, (2,4-dimethoxyphenyl)methylamino or the like;

In the case where $X^1$ is an alkylthio group and n is 1 to 2:

$C_1$ to $C_4$ alkylthio-substituted $C_1$ to $C_{10}$ alkyl groups such as (methylthio)methyl, (ethylthio)methyl, (propylthio)methyl, 2-(methylthio)ethyl, 2-(ethylthio)ethyl, 3-(methylthio)propyl, 4-(methylthio)butyl, 2-(methylthio)propyl, 2-(ethylthio)propyl, 1-(ethylthio)propyl, 2,3-di(methylthio)propyl or the like;

$C_1$ to $C_4$ alkylthio-substituted $C_1$ to $C_{10}$ alkoxy groups such as (methylthio)methoxy, (ethylthio)methoxy, (propylthio)methoxy, 2-(methylthio)ethoxy, 2-(ethylthio)ethoxy, 3-(methylthio)propoxy, 4-(methylthio)butoxy, 2-(methylthio)propoxy, 2-(ethylthio)propoxy, 1-(ethylthio)propoxy, 2,3-di(methylthio)propoxy or the like;

$C_1$ to $C_4$ alkylthio-substituted $C_1$ to $C_{10}$ alkylamino groups such as (methylthio)methylamino, (ethylthio)methylamino, (propylthio)methylamino, 2-(methylthio)ethylamino, 2-(ethylthio)ethylamino, 3-(methylthio)propylamino, 4-(methylthio)butylamino, 2-(methylthio)propylamino, 2-(ethylthio)propylamino, 1-(ethylthio)propylamino, 2,3-di(methylthio)propylamino or the like;

{$C_1$ to $C_4$ alkylthio-substituted di($C_1$ to $C_6$ alkyl)}amino groups such as methyl(2-methylthiomethyl)amino, ethyl(2-methylthio)ethylamino, methyl{(2-ethylthio)propyl}amino, di{(2-ethylthio)ethyl}amino, di{(2-ethylthio)methyl}amino or the like;

$C_1$ to $C_4$ alkylthio-substituted phenyl groups such as 2-(methylthio)phenyl, 3-(methylthio)phenyl, 4-(methylthio)phenyl or the like;

$C_1$ to $C_4$ alkylthio-substituted phenylamino groups such as 2-(methylthio)phenylamino, 3-(methylthio)phenylamino, 4-(methylthio)phenylamino or the like;

($C_1$ to $C_4$ alkylthio-substituted phenyl) $C_1$ to $C_3$ alkyl groups such as {2-(methylthio)phenyl}methyl, {3-(methylthio)phenyl}methyl, {4-(methylthio)phenyl}methyl or the like;

($C_1$ to $C_4$ alkylthio-substituted phenyl) $C_1$ to $C_3$ alkyloxy groups such as {2-(methylthio)phenyl}methyloxy, {3-(methylthio)phenyl}methyloxy, {4-(methylthio)phenyl}methyloxy or the like; and ($C_1$ to $C_4$ alkylthio-substituted phenyl) $C_1$ to $C_3$ alkylamino groups such as {2-(methylthio)phenyl}methylamino, {3-(methylthio)phenyl}methylamino, {4-(methylthio)phenyl}methylamino or the like.

In the case where $X^1$ is an alkylamino group and n is 1:

$C_1$ to $C_4$ alkylamino-substituted $C_1$ to $C_{10}$ alkyl groups such as 2-(methylamino)ethyl, 2-(ethylamino)ethyl, 2-(propylamino)ethyl, 3-(methylamino)propyl or the like;

$C_1$ to $C_4$ alkylamino-substituted $C_1$ to $C_{10}$ alkoxy groups such as 2-(methylamino)ethoxy, 2-(ethylamino)ethoxy, 2-(propylamino)propoxy, 3-(methylamino)propoxy or the like;

$C_1$ to $C_4$ alkylamino-substituted phenyl groups such as 3-(methylamino)phenyl, 4-(methylamino)phenyl, 4-(ethylamino)phenyl or the like;

{($C_1$ to $C_4$ alkylamino)-substituted phenyl) $C_1$ to $C_3$ alkyl groups such as {3-(methylamino)phenyl}methyl, {4-

(methylamino)phenyl}methyl, {4-(ethylamino)
phenyl}methyl or the like;

{($C_1$ to $C_4$ alkylamino)-substituted phenyl} $C_1$ to $C_3$
alkyloxy groups such as {3-(methylamino)
phenyl}methyloxy, {4-(methylamino)
phenyl}methyloxy, {4-(ethylamino)phenyl}methyloxy
or the like; and {($C_1$ to $C_4$ alkylamino)-substituted phenyl} $C_1$ to $C_3$
alkylamino groups such as {3-(methylamino)
phenyl}methylamino, {4-(methylamino)
phenyl}methylamino, {4-(ethylamino)
phenyl}methylamino or the like.

In the case where $X^1$ is a dialkylamino group and n is 1:

{di($C_1$ to $C_4$ alkyl)amino}-substituted $C_1$ to $C_{10}$ alkyl
groups such as 2-(dimethylamino)ethyl,
3-(dimethylamino)propyl, 2-(diethylamino)ethyl,
2-(dipropylamino)ethyl or the like;

{di($C_1$ to $C_4$ alkyl)amino}-substituted $C_1$ to $C_{10}$ alkoxy
groups such as 2-(dimethylamino)ethoxy,
3-(dimethylamino)propoxy, 2-(diethylamino)ethoxy,
2-(dipropylamino)ethoxy or the like;

{di($C_1$ to $C_4$ alkyl)amino}-substituted phenyl groups such
as 3-(dimethylamino)phenyl, 4-(dimethylamino)
phenyl, 4-{methyl(ethyl)amino}phenyl,
4-(diethylamino)phenyl or the like;

{di($C_1$ to $C_4$ alkyl)amino}-substituted phenylamino
groups such as 3-(dimethylamino)phenylamino,
4-(dimethylamino)phenylamino, 4-{methyl(ethyl)
amino)phenylamino, 4-(diethylamino)phenylamino or
the like;

{di($C_1$ to $C_4$ alkyl)amino}-substituted phenyl $C_1$ to $C_3$
alkyl groups such as {3-(dimethylamino)
phenyl}methyl, {4-(dimethylamino)phenyl}methyl,
{4-(diethylamino)phenyl}methyl or the like;

{di($C_1$ to $C_4$ alkyl)amino}-substituted phenyl $C_1$ to $C_3$
alkyloxy groups such as {3-(dimethylamino)
phenyl}methyloxy, {4-(dimethylamino)
phenyl}methyloxy, {4-(diethylamino)
phenyl}methyloxy or the like; and {di($C_1$ to $C_4$ alkyl)amino}-substituted phenyl $C_1$ to $C_3$
alkylamino groups such as {3-(dimethylamino)
phenyl}methylamino, {4-(dimethylamino)
phenyl}methylamino, {4-(diethylamino)
phenyl}methylamino or the like.

In the case where $X^1$ is an alkylsulfinyl group and n is 1 to 2:

$C_1$ to $C_4$ alkylsulfinyl-substituted $C_1$ to $C_{10}$ alkyl groups
such as (methylsulfinyl)methyl, (ethylsulfinyl)methyl,
(propylsulfinyl)methyl, 2-(methylsulfinyl)ethyl,
2-(ethylsulfinyl)ethyl, 3-(methylsulfinyl)propyl,
4-(methylsulfinyl)butyl, 2-(methylsulfinyl)propyl,
2-(ethylsulfinyl)propyl, 1-(ethylsulfinyl)propyl, 2,3-di
(methylsulfinyl)propyl or the like;

$C_1$ to $C_4$ alkylsulfinyl-substituted $C_1$ to $C_{10}$ alkoxy groups
such as (methylsulfinyl)methoxy, (ethylsulfinyl)
methoxy, (propylsulfinyl)methoxy, 2-(methylsulfinyl)
ethoxy, 2-(ethylsulfinyl)ethoxy, 3-(methylsulfinyl)
propoxy, 4-(methylsulfinyl)butoxy, 2-(methylsulfinyl)
propoxy, 2-(ethylsulfinyl)propoxy, 1-(ethylsulfinyl)
propoxy, 2,3-di(methylsulfinyl)propoxy or the like;

$C_1$ to $C_4$ alkylsulfinyl-substituted $C_1$ to $C_{10}$ alkylamino
groups such as (methylsulfinyl)methylamino,
(ethylsulfinyl)methylamino, (propylsulfinyl)
methylamino, 2-(methylsulfinyl)ethylamino,
2-(ethylsulfinyl)ethylamino, 3-(methylsulfinyl)
propylamino, 4-(methylsulfinyl)butylamino,
2-(methylsulfinyl)propylamino, 2-(ethylsulfinyl)
propylamino, 1-(ethylsulfinyl)propylamino, 2,3-di
(methylsulfinyl)propylamino or the like;

{$C_1$ to $C_4$ alkylsulfinyl-substituted di($C_1$ to $C_6$ alkyl)
}amino groups such as methyl(2-
methylsulfinylmethyl)amino, ethyl(2-methylsulfinyl)
ethylamino, methyl{(2-ethylsulfinyl)propyl}amino, di{
(2-ethylsulfinyl)ethyl}amino, di{(2-ethylsulfinyl)
methyl}amino or the like;

$C_1$ to $C_4$ alkylsulfinyl-substituted phenyl groups such as
2-(methylsulfinyl)phenyl, 3-(methylsulfinyl)phenyl,
4-(methylsulfinyl)phenyl or the like;

$C_1$ to $C_4$ alkylsulfinyl-substituted phenylamino groups
such as 2-(methylsulfinyl)phenylamino,
3-(methylsulfinyl)phenylamino, 4-(methylsulfinyl)
phenylamino or the like;

($C_1$ to $C_4$ alkylsulfinyl-substituted phenyl) $C_1$ to $C_3$ alkyl
groups such as {2-(methylsulfinyl)phenyl}methyl, {3-
(methylsulfinyl)phenyl}methyl, {4-(methylsulfinyl)
phenyl}methyl or the like;

($C_1$ to $C_4$ alkylsulfinyl-substituted phenyl) $C_1$ to $C_3$
alkyloxy groups such as {2-(methylsulfinyl)
phenyl}methyloxy, {3-(methylsulfinyl)
phenyl}methyloxy, {4-(methylsulfinyl)
phenyl}methyloxy or the like; and ($C_1$ to $C_4$ alkylsulfinyl-substituted phenyl) $C_1$ to $C_3$
alkylamino groups such as {2-(methylsulfinyl)
phenyl}methylamino, {3-(methylsulfinyl)
phenyl}methylamino, {4-(methylsulfinyl)
phenyl}methylamino or the like.

In the case where $X^1$ is an alkylsulfonyl group and n is 1 to 2:

$C_1$ to $C_4$ alkylsulfonyl-substituted $C_1$ to $C_{10}$ alkyl groups
such as (methylsulfonyl)methyl, (ethylsulfonyl)methyl,
(propylsulfonyl)methyl, 2-(methylsulfonyl)ethyl,
2-(ethylsulfonyl)ethyl, 3-(methylsulfonyl)propyl,
4-(methylsulfonyl)butyl, 2-(methylsulfonyl)propyl,
2-(ethylsulfonyl)propyl, 1-(ethylsulfonyl)propyl, 2,3-
di(methylsulfonyl)propyl or the like;

$C_1$ to $C_4$ alkylsulfonyl-substituted $C_1$ to $C_{10}$ alkoxy
groups such as (methylsulfonyl)methoxy,
(ethylsulfonyl)methoxy, (propylsulfonyl)methoxy,
2-(methylsulfonyl)ethoxy, 2-(ethylsulfonyl)ethoxy,
3-(methylsulfonyl)propoxy, 4-(methylsulfonyl)butoxy,
2-(methylsulfonyl)propoxy, 2-(ethylsulfonyl)propoxy,
1-(ethylsulfonyl)propoxy, 2,3-di(methylsulfonyl)
propoxy or the like;

$C_1$ to $C_4$ alkylsulfonyl-substituted $C_1$ to $C_{10}$ alkylamino
groups such as (methylsulfonyl)methylamino,
(ethylsulfonyl)methylamino, (propylsulfonyl)
methylamino 2-(methylsulfonyl)methylamino,
2-(ethylsulfonyl)methylamino, 3-(methylsulfonyl)
propylamino, 4-(methylsulfonyl)butylamino,
2-(methylsulfonyl)propylamino, 2-(ethylsulfonyl)
propylamino, 1-(ethylsulfonyl)propylamino, 2,3-di
(methylsulfonyl)propylamino or the like;

{$C_1$ to $C_4$ alkylsulfonyl-substituted di($C_1$ to $C_6$ alkyl)
}amino groups such as methyl(2-
methylsulfonylmethyl)amino, ethyl(2-methylsulfonyl)
ethylamino, methyl{(2-ethylsulfonyl)propyl}amino,
di{(2-ethylsulfonyl)ethyl}amino, di{(2-ethylsulfonyl)
methyl}amino or the like;

$C_1$ to $C_4$ alkylsulfonyl-substituted phenyl groups such as
2-(methylsulfonyl)phenyl, 3-(methylsulfonyl)phenyl,
4-(methylsulfonyl)phenyl or the like;

$C_1$ to $C_4$ alkylsulfonyl-substituted phenylamino groups such as 2-(methylsulfonyl)phenylamino, 3-(methylsulfonyl)phenylamino, 4-(methylsulfonyl)phenylamino or the like;

($C_1$ to $C_4$ alkylsulfonyl-substituted phenyl) $C_1$ to $C_3$ alkyl groups such as {2-(methylsulfonyl)phenyl}methyl, {3-(methylsulfonyl)phenyl}methyl, {4-(methylsulfonyl)phenyl}methyl or the like;

($C_1$ to $C_4$ alkylsulfonyl-substituted phenyl) $C_1$ to $C_3$ alkyloxy groups such as {2-(methylsulfonyl)phenyl}methyloxy, (3-(methylsulfonyl)phenyl}methyloxy, {4-(methylsulfonyl)phenyl}methyloxy or the like; and ($C_1$ to $C_4$ alkylsulfonyl-substituted phenyl) $C_1$ to $C_3$ alkylamino groups such as {2-(methylsulfonyl)phenyl}methylamino, {3-(methylsulfonyl)phenyl}methylamino, {4-(methylsulfonyl)phenyl}methylamino or the like.

In the case where $X^1$ is a cyano group and n is 1:

cyano-substituted $C_1$ to $C_{10}$ alkyl groups such as cyanomethyl, 2-cyanoethyl, 3-cyanopropyl, 4-cyanobutyl or the like;

cyano-substituted $C_1$ to $C_{10}$ alkyloxy groups such as 2-cyanoethyloxy, 3-cyanopropyloxy, 4-cyanobutyloxy or the like;

cyano-substituted $C_1$ to $C_{10}$ alkylamino groups such as cyanomethylamino, 2-cyanoethylamino, 3-cyanopropylamino, 4-cyanobutylamino or the like;

{cyano-substituted di($C_1$ to $C_6$ alkyl)}amino groups such as (cyanomethyl)(methyl)amino, (2-cyanoethyl)(ethyl)amino, di(2-cyanoethyl)amino or the like;

cyano-substituted phenyl groups such as 2-cyanophenyl, 3-cyanophenyl, 4-cyanophenyl or the like;

cyano-substituted phenylamino groups such as 2-cyanophenylamino, 3-cyanophenylamino, 4-cyanophenylamino or the like;

(cyano-substituted phenyl) $C_1$ to $C_3$ alkyl groups such as (2-cyanophenyl)methyl, (3-cyanophenyl)methyl, (4-cyanophenyl)methyl or the like;

(cyano-substituted phenyl) $C_1$ to $C_3$ alkyloxy groups such as (2-cyanophenyl)methyloxy, (3-cyanophenyl)methyloxy, (4-cyanophenyl)methyloxy or the like; and (cyano-substituted phenyl) $C_1$ to $C_3$ alkylamino groups such as (2-cyanophenyl)methylamino, (3-cyanophenyl)methylamino, (4-cyanophenyl)methylamino or the like.

In the case where $X^1$ is a cycloalkyl group and n is 1:

$C_3$ to $C_6$ cycloalkyl-substituted $C_1$ to $C_{10}$ alkyl groups such as cyclopropylmethyl, cyclobutylmethyl, cyclopentylmethyl, cyclohexylmethyl, cyclopropylethyl or the like;

$C_3$ to $C_6$ cycloalkyl-substituted $C_1$ to $C_{10}$ alkoxy groups such as cyclopropylmethoxy, cyclobutylmethoxy, cyclopentylmethoxy, cyclohexylmethoxy, cyclopropylethoxy or the like; and $C_3$ to $C_6$ cycloalkyl-substituted $C_1$ to $C_{10}$ alkylamino groups such as cyclopropylmethylamino, cyclobutylmethylamino, cyclopentylmethylamino, cyclohexylmethylamino, cyclopropylethylamino or the like.

In the case where $X^1$ is a alkylcarbonyl group and n is 1:

$C_1$ to $C_4$ alkylcarbonyl-substituted $C_1$ to $C_{10}$ alkyl groups such as (methylcarbonyl)methyl, 2-(methylcarbonyl)ethyl, 3-(methylcarbonyl)propyl, 4-(methylcarbonyl)butyl, (ethylcarbonyl)methyl, 2-(ethylcarbonyl)ethyl, 3-(ethylcarbonyl)propyl, 4-(ethylcarbonyl)butyl, (butylcarbonyl)methyl, 2-(butylcarbonyl)ethyl, 3-(butylcarbonyl)propyl, 4-(butylcarbonyl)butyl or the like;

$C_1$ to $C_4$ alkylcarbonyl-substituted $C_1$ to $C_{10}$ alkoxy groups such as (methylcarbonyl)methoxy, 2-(methylcarbonyl)ethoxy, 3-(methylcarbonyl)propoxy, 4-(methylcarbonyl)butoxy, (ethylcarbonyl)methoxy, 2-(ethylcarbonyl)ethoxy, 3-(ethylcarbonyl)propoxy, 4-(ethylcarbonyl)butoxy, (butylcarbonyl)methoxy, 2-(butylcarbonyl)ethoxy or the like;

$C_1$ to $C_4$ alkylcarbonyl-substituted phenyl groups such as 2-(methylcarbonyl)phenyl, 3-(methylcarbonyl)phenyl, 4-(methylcarbonyl)phenyl or the like;

$C_1$ to $C_4$ alkylcarbonyl-substituted phenylamino groups such as {2-(methylcarbonyl)phenyl}amino, {3-(methylcarbonyl)phenyl}amino, {4-(methylcarbonyl)phenyl}amino or the like;

$C_1$ to $C_4$ alkylcarbonyl-substituted phenyl $C_1$ to $C_3$ alkyl groups such as {2-(methylcarbonyl)phenyl}methyl, {3-(methylcarbonyl)phenyl}methyl, {4-(methylcarbonyl)phenyl}methyl or the like;

$C_1$ to $C_4$ alkylcarbonyl-substituted phenyl $C_1$ to $C_3$ alkyloxy groups such as {2-(methylcarbonyl)phenyl}methyloxy, {3-(methylcarbonyl)phenyl}methyloxy, {4-(methylcarbonyl)phenyl}methyloxy or the like; and $C_1$ to $C_4$ alkylcarbonyl-substituted phenyl $C_1$ to $C_3$ alkylamino groups such as {2-(methylcarbonyl)phenyl}methylamino, {3-(methylcarbonyl)phenyl}methylamino, {4-(methylcarbonyl)phenyl}methylamino or the like; and $C_1$ to $C_4$ alkylcarbonyl-substituted arylalkyloxyamino groups such as 2-(methylcarbonyl)phenylmethyloxyamino, 3-(methylcarbonyl)phenylmethyloxyamino, 4-(methylcarbonyl)phenylmethyloxyamino or the like.

In the case where $X^1$ is an amino group and n is 1:

amino-substituted $C_1$ to $C_{10}$ alkyl groups such as 2-aminoethyl, 3-aminopropyl, 4-aminobutyl or the like; and amino-substituted $C_1$ to $C_{10}$ alkoxy groups such as 2-aminoethoxy, 3-aminopropoxy, 4-aminobutoxy or the like.

In the case where $X^1$ is a hydroxyl group and n is 1 to 2:

hydroxy-substituted $C_1$ to $C_{10}$ alkyl groups such as 2-hydroxyethyl, 3-hydroxypropyl, 2,3-dihydroxypropyl, 4-hydroxybutyl or the like;

hydroxy-substituted $C_1$ to $C_{10}$ alkoxy groups such as 2-hydroxyethoxy, 3-hydroxypropoxy, 2,3-dihydroxypropoxy, 4-hydroxybutoxy or the like; and hydroxy-substituted phenyl groups such as 2-hydroxyphenyl, 3-hydroxyphenyl, 4-hydroxyphenyl or the like.

In the case where $X^1$ is a thiol group and n is 1:

thiol-substituted $C_1$ to $C_{10}$ alkyl groups such as 2-mercaptoethyl, 3-mercaptopropyl, 4-mercaptobutyl or the like;

thiol-substituted $C_1$ to $C_{10}$ alkoxy groups such as 2-mercaptoethoxy, 3-mercaptopropoxy, 2,3-dimercaptopropoxy, 4-mercaptobutoxy or the like; and thiol-substituted phenyl groups such as 2-mercaptophenyl, 3-mercaptophenyl, 4-mercaptophenyl or the like.

As $X^1{}_n$—$A^1$ in which the alkyl moiety of $X^1$ is further substituted with halogen atom(s), there may be exemplified the following substituents. The halogen-substituted alkyl moiety of $X^1$ is hereinafter referred to as "haloalkyl".

In the case where $X^1$ is a haloalkyl group:
  $C_1$ to $C_4$ haloalkyl-substituted phenyl groups such as 3-(trifluoromethyl)phenyl, 4-(trifluoromethyl)phenyl, 2-(trifluoromethyl)phenyl or the like;
  $C_1$ to $C_4$ haloalkyl-substituted phenylamino groups such as 3-(trifluoromethyl)phenylamino or the like; and
  $C_1$ to $C_4$ haloalkyl-substituted phenyl $C_1$ to $C_4$ alkyloxy groups such as 3-(trifluoromethyl)phenylmethyloxy, 4-(trifluoromethyl)phenylmethyloxy or the like;

In the case where $X^1$ is a haloalkoxy group:
  $C_1$ to $C_4$ haloalkoxy-substituted $C_1$ to $C_{10}$ alkyl groups such as 3-(trifluoromethoxy)ethyl, 2-(2,2,2-trifluoroethoxy) ethyl, (2,2,2-trifluoroethoxy)methyl, (2,2,3,3,3-pentafluoropropoxy)methyl, 2-(difluoromethoxy)ethyl, 2-(2-fluoroethoxy)ethyl, 1-(2-fluoroethoxy)methyl, 2-(chloroethoxy)ethyl, 2-(bromoethoxy)ethyl, 2-(trichloromethoxy)ethyl or the like;
  $C_1$ to $C_4$ haloalkoxy-substituted $C_1$ to $C_{10}$ alkoxy groups such as 2-(trifluoromethoxy)ethoxy, 2-(2,2,2-trifluoroethoxy)ethoxy, (2,2,2-trifluoroethoxy) methoxy, 2-(difluoromethoxy)ethoxy, (2-fluoroethoxy) methoxy, 2-(chloroethoxy)ethoxy, 2-(bromoethoxy) ethoxy or the like;
  $C_1$ to $C_4$ haloalkoxy-substituted phenyl groups such as 3-(trifluoromethoxy)phenyl, 4-(trifluoromethoxy) phenyl, 2-(trifluoromethoxy)phenyl or the like;
  $C_1$ to $C_4$ haloalkoxy-substituted phenylamino groups such as 3-(trifluoromethoxy)phenylamino or the like; and
  $C_1$ to $C_4$ haloalkoxy-substituted phenyl $C_1$ to $C_3$ alkyloxy groups such as 3-(trifluoromethoxy)phenylmethyloxy, 4-(trifluoromethoxy)phenylmethyloxy or the like;

In the case where $X^1$ is a haloalkylthio group:
  $C_1$ to $C_4$ haloalkylthio-substituted $C_1$ to $C_1$ alkoxy such as 2-(trifluoromethylthio)ethyl, 2-(2,2,2-trifluoroethylthio) ethyl, (2,2,2-trifluoroethylthio) methyl, (2,2,3,3,3-pentafluoropropylthio)methyl, 2-(difluoromethylthio)ethyl, 2-(2-fluoroethylthio)ethyl, (2-fluoroethylthio)methyl, 2-(chloroethylthio)ethyl, 2-(bromoethylthio)ethyl, 2-(trichloromethylthio)ethyl or the like;
  $C_1$ to $C_4$ haloalkylthio-substituted $C_1$ to $C_{10}$ alkoxy groups such as 2-(trifluoromethylthio)ethoxy, 2-(2,2,2-trifluoroethylthio)ethoxy, (2,2,2-trifluoroethylthio) methoxy, 2-(difluoromethylthio)ethoxy, 2-(2-fluoroethylthio)ethoxy, (2-fluoroethylthio)methoxy, 2-(chloroethylthio)ethoxy, 2-(bromoethylthio)ethoxy or the like;
  $C_1$ to $C_4$ haloalkylthio-substituted phenyl groups such as 3-(trifluoromethylthio)phenyl, 4-(trifluoromethylthio) phenyl, 2-(trifluoromethylthio)phenyl or the like;
  $C_1$ to $C_4$ haloalkylthio-substituted phenylamino groups such as 3-(trifluoromethylthio)phenylamino or the like;
  $C_1$ to $C_4$ haloalkylthio-substituted phenyl $C_1$ to $C_3$ alkyl groups such as {3-(trifluoromethylthio)phenyl}methyl, {4-(trifluoromethylthio)phenyl}methyl or the like;
  $C_1$ to $C_4$ haloalkylthio-substituted phenyl $C_1$ to $C_3$ alkyloxy groups such as {3-(trifluoromethylthio)phenyl}methyloxy, {4-(trifluoromethylthio)phenyl}methyloxy or the like; and
  $C_1$ to $C_4$ haloalkylthio-substituted phenyl $C_1$ to $C_3$ alkylamino groups such as {3-(trifluoromethylthio)phenyl}methylamino, {4-(trifluoromethylthio)phenyl}methylamino or the like.

In the case where $X^1$ is a haloalkylsulfinyl group:
  $C_1$ to $C_4$ haloalkylsulfinyl-substituted $C_1$ to $C_{10}$ alkyl groups such as 2-(trifluoromethylsulfinyl)ethyl, 2-(2,2,2-trifluoroethylsulfinyl)ethyl, (2,2,2-trifluoroethylsulfinyl)methyl, (2,2,3,3,3-pentafluoropropylsulfinyl)methyl, 2-(difluoromethylsulfinyl)ethyl, 2-(2-fluoroethylsulfinyl)ethyl, (2-fluoroethylsulfinyl) methyl, 2-(chloroethylsulfinyl)ethyl, 2-(bromoethylsulfinyl)ethyl, 2-(trichloromethylsulfinyl)ethyl or the like;
  $C_1$ to $C_4$ haloalkylsulfinyl-substituted $C_1$ to $C_{10}$ alkoxy groups such as 2-(trifluoromethylsulfinyl)ethoxy, 2-(2,2,2-trifluoroethylsulfinyl)ethoxy, (2,2,2-trifluoroethylsulfinyl)methoxy, 2-(difluoromethylsulfinyl)ethoxy, 2-(2-fluoroethylsulfinyl)ethoxy, (2-fluoroethylsulfinyl) methoxy, 2-(chloroethylsulfinyl)ethoxy, 2-(bromoethylsulfinyl)methoxy or the like;
  $C_1$ to $C_4$ haloalkylsulfinyl-substituted phenyl groups such as 3-(trifluoromethylsulfinyl)phenyl, 4-(trifluoromethylsulfinyl)phenyl, 2-(trifluoromethylsulfinyl)phenyl or the like;
  $C_1$ to $C_4$ haloalkylsulfinyl-substituted phenylamino groups such as 3-(trifluoromethylsulfinyl)phenylamino or the like;
  $C_1$ to $C_4$ haloalkylsulfinyl-substituted phenyl $C_1$ to $C_3$ alkyl groups such as {3-(trifluoromethylsulfinyl)phenyl}methyl, {4-(trifluoromethylsulfinyl)phenyl}methyl or the like;
  $C_1$ to $C_4$ haloalkylsulfinyl-substituted phenyl $C_1$ to $C_3$ alkyloxy groups such as {3-(trifluoromethylsulfinyl)phenyl}methyloxy, {4-(trifluoromethylsulfinyl)phenyl}methyloxy or the like; and
  $C_1$ to $C_4$ haloalkylsulfinyl-substituted phenyl $C_1$ to $C_3$ alkylamino groups such as {3-(trifluoromethylsulfinyl)phenyl}methylamino, {4-(trifluoromethylsulfinyl)phenyl}methylamino or the like.

In the case where $X^1$ is a haloalkylsulfonyl group:
  $C_1$ to $C_4$ haloalkylsulfonyl-substituted $C_1$ to $C_{10}$ alkyl groups such as 2-(trifluoromethylsulfonyl)ethyl, 2-(2,2,2-trifluoroethylsulfonyl)ethyl, (2,2,2-trifluoroethylsulfonyl)methyl, (2,2,3,3,3-pentafluoropropylsulfonyl)methyl, 2-(difluoromethylsulfonyl)ethyl, 2-(2-fluoroethylsulfonyl)ethyl, (2-fluoroethylsulfonyl) methyl, 2-(chloroethylsulfonyl)ethyl, 2-(bromoethylsulfonyl)methyl, 2-(trichloromethylsulfonyl)ethyl or the like;
  $C_1$ to $C_4$ haloalkylsulfonyl-substituted $C_1$ to $C_{10}$ alkoxy groups such as 2-(trifluoromethylsulfonyl)ethoxy, 2-(2,2,2-trifluoroethylsulfonyl)ethoxy, (2,2,2-trifluoroethylsulfonyl)methoxy, 2-(difluoromethylsulfonyl)ethoxy, 2-(2-fluoroethylsulfonyl)ethoxy, (2-fluoroethylsulfonyl) methoxy, 2-(chloroethylsulfonyl)ethoxy, 2-(bromoethylsulfonyl)ethoxy or the like;
  $C_1$ to $C_4$ haloalkylsulfonyl-substituted phenyl groups such as 3-(trifluoromethylsulfonyl)phenyl, 4-(trifluoromethylsulfonyl)phenyl, 2-(trifluoromethylsulfonyl)phenyl or the like;
  $C_1$ to $C_4$ haloalkylsulfonyl-substituted phenylamino groups such as 3-(trifluoromethylsulfonyl) phenylamino or the like;

- $C_1$ to $C_4$ haloalkylsulfonyl-substituted phenyl $C_1$ to $C_3$ alkyl groups such as {3-(trifluoromethylsulfonyl)phenyl}methyl, {4-(trifluoromethylsulfonyl)phenyl}methyl or the like;
- $C_1$ to $C_4$ haloalkylsulfonyl-substituted phenyl $C_1$ to $C_3$ alkyloxy groups such as {3-(trifluoromethylsulfonyl)phenyl}methyloxy, {4-(trifluoromethylsulfonyl)phenyl}methyloxy or the like; and
- $C_1$ to $C_4$ haloalkylsulfonyl-substituted phenyl $C_1$ to $C_3$ alkylamino groups such as {3-(trifluoromethylsulfonyl)phenyl}methylamino, {4-(trifluoromethylsulfonyl)phenyl}methylamino or the like.

In the case where $X^1$ is a haloalkylcarbonyl group:
- $C_1$ to $C_4$ haloalkylcarbonyl-substituted $C_1$ to $C_{10}$ alkyl groups such as 2-(trifluoromethylcarbonyl)ethyl, 2-(trifluoromethylcarbonyl)methyl, 2-(2,2,2-trifluoroethylcarbonyl)ethyl, (2,2,2-trifluoroethylcarbonyl)methyl, 2-(2,2,3,3,3-pentafluoropropylcarbonyl)methyl, 2-(1,1,2,2,2-pentafluoroethylcarbonyl)ethyl, 2-(trichloromethylcarbonyl)ethyl or the like;
- $C_1$ to $C_4$ haloalkylcarbonyl-substituted phenyl groups such as 3-(trifluoromethylcarbonyl)phenyl, 4-(trifluoromethylcarbonyl)phenyl, 2-(trifluoromethylcarbonyl)phenyl or the like;
- ($C_1$ to $C_4$ haloalkylcarbonyl-substituted phenyl)amino groups such as {3-(trifluoromethylcarbonyl)phenyl}amino or the like;
- ($C_1$ to $C_4$ haloalkylcarbonyl-substituted phenyl) $C_1$ to $C_3$ alkyl groups such as {3-(trifluoromethylcarbonyl)phenyl}methyl, {4-(trifluoromethylcarbonyl)phenyl}methyl or the like;
- $C_1$ to $C_4$ haloalkylcarbonyl-substituted phenyl $C_1$ to $C_3$ alkyloxy groups such as {3-(trifluoromethylcarbonyl)phenyl}methyloxy, {4-(trifluoromethylcarbonyl)phenyl}methyloxy or the like; and
- ($C_1$ to $C_4$ haloalkylcarbonyl-substituted phenyl) $C_1$ to $C_3$ alkylamino groups such as {3-(trifluoromethylcarbonyl)phenyl}methylamino, {4-(trifluoromethylcarbonyl)phenyl}methylamino or the like.

Further, in the case where $X^1$ is a halogen-substituted $C_1$ to $C_3$ cycloalkyl group, as the $X^1_n$—$A^1$, there may be exemplified 2,2-dichlorocyclopropylmethyl or the like.

Next, among the above-mentioned definitions of $X^1_n$—$A^1$, specific preferred examples thereof are shown below:
- hydroxyl;
- methyl, ethyl, propyl, butyl, pentyl or hexyl;
- 2-propenyl or 2-propynyl;
- cyclopropyl, cyclobutyl, cyclopentyl or cyclohexyl;
- methoxy, ethoxy, propoxy, butoxy, 2-propenyloxy or 2-propynyloxy;
- methylamino, ethylamino, propylamino, butylamino, dimethylamino, diethylamino or methyl(ethyl)amino;
- phenyl, phenylamino, phenylmethyl, phenylmethyloxy or phenylmethylamino;
- 1-methylethyl, 1-methylpropyl, 1-methylbutyl, 2-methylpropyl, 2-methylbutyl, 1-ethylpropyl, 1,1-dimethylethyl, 1,1-dimethylpropyl or 1,1-dimethylethylamino;
- 2-methylphenyl, 3-methylphenyl or 4-methylphenyl;
- 2-fluoroethyl, 2,2,2-trifluoroethyl, 3,3,3-trifluoropropyl, 2,2,3,3,3-pentafluoropropyl, 2,2,3,3,4,4,4-heptafluorobutyl, 2-chloroethyl, 3-chloropropyl, 2-bromoethyl or 2,2-dichloroethenyl;
- 2-fluoroethoxy or 2,2,2-trifluoroethoxy;
- 2-chlorophenyl, 3-chlorophenyl, 4-chlorophenyl, 2-fluorophenyl, 3-fluorophenyl, 4-fluorophenyl or 2,4-difluorophenyl;
- methoxymethyl, ethoxymethyl, 2-(methoxy)ethyl, 1-(methoxy)ethyl, 1-(methoxy)propyl, 2-(ethoxy)ethyl, 3-(methoxy)propyl, methoxymethoxy, ethoxymethoxy or propoxymethoxy;
- 3-(methoxy)phenyl or 4-(methoxy)phenyl;
- methylthiomethyl, ethylthiomethyl, 2-(methylthio)ethyl, 2-(ethylthio)ethyl, 3-(methylthio)propyl, methylthiomethoxy, ethylthiomethoxy or 4-(methylthio)phenyl;
- 2-(dimethylamino)ethyl;
- methylsulfinylmethyl, ethylsulfinylmethyl, methylsulfinylethyl, 2-(ethylsulfinyl)ethyl or 3-(methylsulfinyl)propyl;
- methylsulfonylmethyl, ethylsulfonylmethyl, propylsulfonylmethyl, methylsulfonylethyl, 2-(ethylsulfonyl)ethyl or 3-(methylsulfonyl)propyl or methylsulfonylmethoxy;
- 1-cyanomethyl, 2-cyanoethyl or 3-cyanopropyl;
- cyclopropylmethyl;
- 1-(methylcarbonyl)methyl, 2-(methylcarbonyl)ethyl, 1-(ethylcarbonyl)methyl, 2-(ethylcarbonyl)ethyl or 2-hydroxyethyl;
- 3-hydroxypropyl, 3-(trifluoromethyl)phenyl, 4-(trifluoromethyl)phenyl, 2-(trifluoromethyl)phenyl, 2-(2,2,2-trifluoroethoxy)ethyl or 2-(2-fluoroethoxy)ethyl;
- 2-(trifluoromethylthio)ethyl, 2-(2,2,2-trifluoroethylthio)ethyl, 2-(2-fluoroethylthio)ethyl, 2-(trifluoromethylsulfonyl)ethyl, 2-(2,2,2-trifluoroethylsulfonyl)ethyl or 2-(2-fluoroethylsulfonyl)ethyl; and
- 1-methoxy-2,2,2-trifluoroethyl or cyclopropylmethoxy.

Among the above definitions, the following substituents ($A^1$—$X^1_n$) are more preferred:
- methyl, ethyl, propyl, butyl, pentyl, propenyl, cyclopropyl, cyclobutyl, cyclopentyl or cyclohexyl;
- methoxy, propoxy or 2-propenyloxy;
- methylamino, 1,1-dimethylethylamino or dimethylamino;
- phenyl, phenylmethyl, 1-methylethyl, 1-methylpropyl, 2-methylpropyl or 2-fluoroethyl;
- 2,2,2-trifluoroethyl, 2,2,3,3,3-pentafluoropropyl, 2,2,3,3,4,4,4-heptafluorobutyl, 2-chloroethyl, 3-chloropropyl or 2,2-dichloroethenyl;
- 2-fluoroethoxy, 4-chlorophenyl or 4-fluorophenyl;
- ethoxymethyl, 2-(methoxy)ethyl, 3-(methoxy)propyl or ethoxymethoxy;
- 2-(methylthio)ethyl, 2-(ethylthio)ethyl or 3-(methylthio)propyl;
- 2-(ethylsulfinyl)ethyl, methylsulfonylmethyl, 2-(methylsulfonyl)ethyl, 2-(ethylsulfonyl)ethyl or 3-(methylsulfonyl)propyl;
- cyanomethyl, 2-cyanoethyl or cyclopropylmethyl;
- 1-(ethylcarbonyl)methyl; and
- 2-hydroxyethyl, 2-(2-fluoroethoxy)ethyl, 2-(2,2,2-trifluoroethylthio)ethyl, 2-(2-fluoroethylthio)ethyl, 1-methoxy-2,2,2-trifluoroethyl or cyclopropylmethoxy.

Among the above definitions, the following substituents ($A^1$—$X^1_n$) are still more preferred:

propyl, butyl, cyclopropyl, cyclobutyl, cyclopentyl or cyclohexyl;

methoxy, propoxy or 2-propenyloxy;

dimethylamino or 1,1-dimethylethylamino;

1-methylethyl, 1-methylpropyl or 2-methylpropyl;

2-fluoroethyl, 2,2,2-trifluoroethyl, 2,2,3,3,3-pentafluoropropyl, 2,2,3,3,4,4,4-heptafluorobutyl, 2-chloroethyl, 3-chloropropyl or 2,2-dichloroethenyl; and ethoxymethyl, methylsulfonylmethyl, methylsulfonylethyl, 2-cyanoethyl or cyclopropylmethyl.

The above-specified contents of $X^1$—$A^1$ are common to specific contents of $X^2_n$—$A^2$, $X^{1b}_n$—$A^{1b}$, $X^3_n$—$A^3$, $X^3_n$—$A^{3a}$, $X^4_n$—$A^{4a}$—$E^1$, $X^5_n$—$A^5$, $(HE^2)_j(X^{5a})_kA^5$, $(R^5—E^2)_{j1}(HE^2)_{j2}(X^{5a})_kA^5$ and $X^{1f}_n$—$A^{1f}$ within the scopes of definitions thereof.

In the case where the two $A^1$s in $(X^1_n—A^1)_2$ both are alkyl chains, the $A^1$s may be directly bonded to each other or may be bonded to each other through an oxygen atom of the hydroxyl group or a nitrogen atom of the amino group or the $C_1$ to $C_4$ alkylamino group which groups are bonded to one of the two $A^1$s to form a ring including nitrogen of carboxamide or thiocarboxamide of the present compound (I).

When such cyclic secondary amines are represented as groups bonded to a carbonyl or thiocarbonyl group of the carboxamide or thiocarboxamide of the present compound (I), there may be exemplified the following groups:

Groups forming a ring by direct bond between carbon atoms of respective $A^1$s which carbon atoms lack in bonding number, such as propylene imine-1-yl (The term "-1-yl" indicates that the carbonyl or thiocarbonyl group of carboxamide or thiocarboxamide is formed at the 1-position of propylene imine; hereinafter described using the similar regularity), azetidine-1-yl, pyrrolidine-1-yl, piperidine-1-yl, 2-methyl piperidine-1-yl or 3-methyl piperidine-1-yl;

Groups forming a ring by bonding a carbon atom of one of the two $A^1$s with an oxygen atom of $X^1$ (=hydroxy) bonded to the other of the $A^1$s, i.e., through the oxygen atom, such as morpholine-4-yl or 2,6-dimethyl morpholine-4-yl; and Groups forming a ring by bonding a carbon atom of one of the two $A^1$s with a nitrogen atom of $X^1$ (=amino group or $C_1$ to $C_4$ alkylamino group) bonded to the other of the $A^1$s, i.e., through the nitrogen atom, such as piperazine-1-yl or 4-methyl piperazine-1-yl.

Among these cyclic secondary amines, 3- to 10-membered rings are preferred, and 3- to 6-membered rings are especially preferred.

The above-specified contents of $(X^1_n—A^1)_2$ are common to specific contents of $(X^{1b}_n—A^{1b})_2$, $(HE^2—A^5)_2$, $(R^5—HE^2—A^5)$ and $(X^{1f}_n—A^{1f})_2$ within the scopes of definitions thereof.

The integer p is preferably 1 or 2, more preferably 1.

The sum of s and p (s+p) represents 2.

The above-specified contents of s and p are common to specific contents of t, v, w, x and y within the scopes of definitions thereof.

As $Y^1$ of the present compound (I), there may be exemplified the following specific substituents:

$C_1$ to $C_4$ haloalkyl groups such as trifluoromethyl;

$C_1$ to $C_4$ alkyl groups such as methyl, ethyl or (1-methyl)ethyl;

$C_1$ to $C_4$ alkoxy groups such as methoxy, ethoxy or (1-methyl)ethoxy;

$C_1$ to $C_4$ haloalkoxy groups such as trifluoromethoxy or difluoromethoxy;

$C_1$ to $C_4$ alkylthio groups such as methylthio, ethylthio or (1-methyl)ethylthio;

$C_1$ to $C_4$ haloalkylthio groups such as trifluoromethylthio or difluoromethylthio; and halogen atoms such as, usually, fluorine, chorine or bromine.

Among the above definitions, the preferred $Y^1$s are the following substituents:

trifluoromethyl, methyl, methoxy, trifluoromethoxy, difluoromethoxy, trifluoromethylthio, difluoromethylthio, chlorine or bromine.

The more preferred $Y^1$s are trifluoromethyl, trifluoromethoxy, difluoromethoxy or trifluoromethylthio.

The integer m of $Y^1$ of the present compound (I) is preferably in the range of 0 (indicating that the compound is unsubstituted with $Y^1$) to 3. It is still more preferred that m is 1 and $Y^1$ is bonded to the 3-position of the compound.

The above-specified contents of $Y^1$ are common to specific contents of $Y^2$ within the scope of definition thereof.

In view of combinations between the above-mentioned substituents and integers, as the present compounds (I), there may be exemplified compounds shown in the following Tables 1 to 10.

TABLE 1

| | | | Substituent | | | |
|---|---|---|---|---|---|---|
| Comp. No. | $R^1$ | $A^1$ a) | Substituent $X^1$n on $A^1$ b) | p | $Y^1$m | Z |
| I-1 | $OCH_3$ | Ph | — | 1 | 3-$CF_3$ | O |
| I-2 | $OCH_3$ | $C_6H_4$ | 4-Cl | 1 | 3-$CF_3$ | O |
| I-3 | $OCH_3$ | $C_6H_4$ | 3-Cl | 1 | 3-$CF_3$ | O |
| I-4 | $OCH_3$ | $C_6H_4$ | 2-Cl | 1 | 3-$CF_3$ | O |
| I-5 | $OCH_3$ | $C_6H_4$ | 4-$CH_3$ | 1 | 3-$CF_3$ | O |
| I-6 | $OCH_3$ | $C_6H_4$ | 3-$CH_3$ | 1 | 3-$CF_3$ | O |
| I-7 | $OCH_3$ | $C_6H_4$ | 2-$CH_3$ | 1 | 3-$CF_3$ | O |
| I-8 | $OCH_3$ | $C_6H_4$ | 4-$OCH_3$ | 1 | 3-$CF_3$ | O |
| I-9 | $OCH_3$ | $C_6H_4$ | 4-$SCH_3$ | 1 | 3-$CF_3$ | O |
| I-10 | $OCH_3$ | $C_6H_4$ | 3-$CF_3$ | 1 | 3-$CF_3$ | O |
| I-11 | $OCH_3$ | $C_6H_4$ | 4-F | 1 | 3-$CF_3$ | O |
| I-12 | $OCH_3$ | $C_6H_4$ | 3-F | 1 | 3-$CF_3$ | O |
| I-13 | $OCH_3$ | $C_6H_4$ | 2-F | 1 | 3-$CF_3$ | O |
| I-14 | $OCH_3$ | $C_6H_3$ | 2,4-$F_2$ | 1 | 3-$CF_3$ | O |
| I-15 | $OCH_3$ | Ph | — | 1 | 3-Cl | O |
| I-16 | $OCH_3$ | Ph | — | 1 | 3-$CH_3$ | O |
| I-17 | $OCH_3$ | Ph | — | 1 | 3-$OCH_3$ | O |
| I-18 | $OCH_3$ | Ph | — | 1 | 3-$SCH_3$ | O |
| I-19 | $OCH_3$ | Ph | — | 1 | 3-$OCHF_2$ | O |

TABLE 2

| | | | Substituent | | | |
|---|---|---|---|---|---|---|
| Comp. No. | $R^1$ | $A^1$ a) | Substituent $X^1$n on $A^1$ b) | p | $Y^1$m | Z |
| I-20 | $OCH_3$ | Ph | — | 1 | 3-$OCF_3$ | O |
| I-21 | $OCH_3$ | Ph | — | 1 | 3-$SCF_3$ | O |
| I-22 | $SCH_3$ | Ph | — | 1 | 3-$CF_3$ | O |
| I-23 | $NHCH_3$ | Ph | — | 1 | 3-$CF_3$ | O |
| I-24 | $N(CH_3)_2$ | Ph | — | 1 | 3-$CF_3$ | O |
| I-25 | $OCH_2CH_3$ | Ph | — | 1 | 3-$CF_3$ | O |
| I-26 | $OCH_3$ | Ph | — | 1 | 3-$CF_3$ | S |
| I-27 | $OCH_3$ | Ph | 3-$OCH_3$ | 1 | 3-$CF_3$ | O |

TABLE 2-continued

| Comp. No. | R$^1$ | A$^1$ a) | Substituent X$^1$n on A$^1$ b) | p | Y$^1$m | Z |
|---|---|---|---|---|---|---|
| I-28 | OCH$_3$ | C$_6$H$_4$ | 4-CH$_3$ | 1 | 3-CH$_3$ | 0 |
| I-29 | N(CH$_3$)CH$_2$Ph | Ph | — | 1 | 3-CF$_3$ | 0 |
| I-30 | OCH$_3$ | C$_6$H$_4$ | 4-CH$_3$ | 1 | 3-OCF$_3$ | 0 |
| I-31 | OCH$_3$ | C$_6$H$_4$ | 4-Cl | 1 | 3-CF$_3$ | S |
| I-32 | OCH$_3$ | C$_6$H$_4$ | 4-Br | 1 | 3-CF$_3$ | 0 |
| I-33 | OCH$_3$ | (CH$_2$)$_2$CH$_3$ | — | 1 | 3-CF$_3$ | 0 |
| I-34 | OCH$_3$ | (CH$_2$)$_2$CH$_3$ | — | 1 | 3-CF$_3$ | S |
| I-35 | OCH$_3$ | CH$_2$CH$_2$ | 2-Cl | 1 | 3-CF$_3$ | 0 |
| I-36 | OCH$_3$ | (CH$_2$)$_3$CH$_3$ | — | 1 | 3-CF$_3$ | 0 |
| I-37 | OCH$_3$ | CHCH$_3$ | 1-CH$_3$ | 1 | 3-CF$_3$ | 0 |
| I-38 | OCH$_3$ | CHCH$_3$ | 1-CH$_3$ | 1 | 3-OCHF$_2$ | 0 |
| I-39 | OCH$_3$ | CHCH$_3$ | 1-CH$_3$ | 1 | 3-OCF$_3$ | 0 |

TABLE 3

| Comp. No. | R$^1$ | A$^1$ a) | Substituent X$^1$n on A$^1$ b) | p | Y$^1$m | Z |
|---|---|---|---|---|---|---|
| I-40 | OCH$_3$ | CHCH$_3$ | 1-CH$_3$ | 1 | 3-SCF$_3$ | 0 |
| I-41 | OCH$_3$ | CCH$_3$ | 1,1-(CH$_3$)$_2$ | 1 | 3-CF$_3$ | 0 |
| I-42 | OCH$_3$ | CH$_2$CH=CH$_2$ | — | 1 | 3-CF$_3$ | 0 |
| I-43 | OCH$_3$ | cyclohexyl | — | 1 | 3-CF$_3$ | 0 |
| I-44 | OCH$_3$ | CH$_2$CH$_3$ | — | 1 | 3-CF$_3$ | S |
| I-45 | OCH$_3$ | CH$_2$Ph | — | 1 | 3-CF$_3$ | 0 |
| I-46 | OCH$_3$ | CH$_3$ | — | 1 | 3-CF$_3$ | 0 |
| I-47 | OCH$_3$ | CH$_3$ | — | 1 | 3-CF$_3$ | S |
| I-48 | OCH$_3$ | cyclopropyl | — | 1 | 3-CF$_3$ | 0 |
| I-49 | OCH$_3$ | cyclobutyl | — | 1 | 3-CF$_3$ | 0 |
| I-50 | OCH$_3$ | cyclopentyl | — | 1 | 3-CF$_3$ | 0 |
| I-51 | OCH$_3$ | CH$_2$CH$_3$ | — | 1 | 3-CF$_3$ | 0 |
| I-52 | OCH$_3$ | (CH$_2$)$_4$CH$_3$ | — | 1 | 3-CF$_3$ | 0 |
| I-53 | OCH$_3$ | (CH$_2$)$_5$CH$_3$ | — | 1 | 3-CF$_3$ | 0 |
| I-54 | OCH$_3$ | (CH$_2$)$_6$CH$_3$ | — | 1 | 3-CF$_3$ | 0 |
| I-55 | SCH$_3$ | CHCH$_3$ | 1-CH$_3$ | 1 | 3-CF$_3$ | 0 |
| I-56 | NHCH$_3$ | CHCH$_3$ | 1-CH$_3$ | 1 | 3-CF$_3$ | 0 |
| I-57 | N(CH$_3$)$_2$ | CHCH$_3$ | 1-CH$_3$ | 1 | 3-CF$_3$ | 0 |
| I-58 | N(CH$_3$)CH$_2$Ph | CHCH$_3$ | 1-CH$_3$ | 1 | 3-CF$_3$ | 0 |
| I-59 | OCH$_2$CH$_3$ | CHCH$_3$ | 1-CH$_3$ | 1 | 3-CF$_3$ | 0 |

TABLE 4

| Comp. No. | R$^1$ | A$^1$ a) | Substituent X$^1$n on A$^1$ b) | p | Y$^1$m | Z |
|---|---|---|---|---|---|---|
| I-60 | OCH$_2$CH$_3$ | CH$_3$ | — | 1 | 3-CF$_3$ | 0 |
| I-61 | OCH$_3$ | CH$_2$CH$_2$ | 2-OCH$_3$ | 1 | 3-CF$_3$ | 0 |
| I-62 | OCH$_3$ | CH$_2$CH$_2$ | 2-SCH$_3$ | 1 | 3-CF$_3$ | 0 |
| I-63 | OCH$_3$ | CH$_2$CH$_2$ | 2-SO$_2$CH$_3$ | 1 | 3-CF$_3$ | 0 |
| I-64 | OCH$_3$ | CH$_2$CH$_2$ | 2-N(CH$_3$)2 | 1 | 3-CF$_3$ | 0 |
| I-65 | OCH$_3$ | CH$_2$CH$_2$ | 2-Br | 1 | 3-CF$_3$ | 0 |
| I-66 | OCH$_3$ | CH$_2$CH$_2$ | 2-OCH$_2$CH$_3$ | 1 | 3-CF$_3$ | 0 |
| I-67 | OCH$_3$ | CH$_2$CH$_2$ | 2-SCH$_2$CH$_3$ | 1 | 3-CF$_3$ | 0 |
| I-68 | OCH$_3$ | CH$_2$CH$_2$ | 2-SO$_2$CH$_2$CH$_3$ | 1 | 3-CF$_3$ | 0 |
| I-69 | OCH$_3$ | CH$_2$CH$_2$ | 2-SOCH$_2$CH$_3$ | 1 | 3-CF$_3$ | 0 |
| I-70 | OCH$_3$ | CH$_2$CH$_2$ | 2-COCH$_3$ | 1 | 3-CF$_3$ | 0 |
| I-71 | OCH$_3$ | CH$_2$CH$_2$ | 2-CN | 1 | 3-CF$_3$ | 0 |
| I-72 | OCH$_3$ | CH$_2$CHCH$_3$ | 2-CH$_3$ | 1 | 3-CF$_3$ | 0 |
| I-73 | OCH$_3$ | CHCH$_2$CH$_3$ | 1-CH$_3$ | 1 | 3-CF$_3$ | 0 |
| I-74 | OCH$_3$ | CH$_2$CH$_2$ | 2-F | 1 | 3-CF$_3$ | 0 |
| I-75 | OCH$_3$ | CH$_2$CH$_2$CH$_2$ | 3-OCH$_3$ | 1 | 3-CF$_3$ | 0 |
| I-76 | OCH$_3$ | CH$_2$CH$_2$CH$_2$ | 3-SCH$_3$ | 1 | 3-CF$_3$ | 0 |

TABLE 4-continued

| Comp. No. | R$^1$ | A$^1$ a) | Substituent X$^1$n on A$^1$ b) | p | Y$^1$m | Z |
|---|---|---|---|---|---|---|
| I-77 | OCH$_3$ | CH$_2$CH$_2$CH$_2$ | 3-SO$_2$CH$_3$ | 1 | 3-CF$_3$ | 0 |
| I-78 | OCH$_3$ | CH$_2$CH$_2$CH$_2$ | 3-SOCH$_3$ | 1 | 3-CF$_3$ | 0 |

TABLE 5

| Comp. No. | R$^1$ | A$^1$ a) | Substituent X$^1$n on A$^1$ b) | p | Y$^1$m | Z |
|---|---|---|---|---|---|---|
| I-79 | OCH$_3$ | CH$_2$CH$_2$CH$_2$ | 3-Cl | 1 | 3-CF$_3$ | 0 |
| I-80 | OCH$_3$ | CH$_2$CCC | 2,2,3,3,4,4,4-F$_7$ | 1 | 3-CF$_3$ | 0 |
| I-81 | OCH$_3$ | CH$_2$CC | 2,2,3,3,3-F$_5$ | 1 | 3-CF$_3$ | 0 |
| I-82 | OCH$_3$ | CH$_2$C | 2,2,2-F$_3$ | 1 | 3-CF$_3$ | 0 |
| I-83 | OCH$_3$ | CH=C | 2,2-Cl$_2$ | 1 | 3-CF$_3$ | 0 |
| I-84 | OCH$_3$ | CH$_2$ | 1-CN | 1 | 3-CF$_3$ | 0 |

TABLE 6

| Comp. No. | R$^1$ | A$^1$ a) | Substituent X$^1$n on A$^1$ b) | p | Y$^1$m | Z |
|---|---|---|---|---|---|---|
| I-85 | OCH$_3$ | CH$_2$ | 1-cyclopropyl | 1 | 3-CF$_3$ | 0 |
| I-86 | OCH$_3$ | CH$_2$ | 1-COCH$_2$CH$_3$ | 1 | 3-CF$_3$ | 0 |
| I-87 | OCH$_3$ | CH$_2$ | 1-OCH$_2$CH$_3$ | 1 | 3-CF$_3$ | 0 |
| I-88 | OCH$_3$ | CHC | 1-OCH$_3$-2,2,2-F$_3$ | 1 | 3-CF$_3$ | 0 |
| I-89 | OCH$_3$ | CH$_2$CH$_2$ | 2-OH | 1 | 3-CF$_3$ | 0 |
| I-90 | OCH$_3$ | CH$_2$CH$_2$ | 2-OCH$_2$F | 1 | 3-CF$_3$ | 0 |
| I-91 | OCH$_3$ | CH$_2$CH$_2$ | 2-SH | 1 | 3-CF$_3$ | 0 |
| I-92 | OCH$_3$ | CH$_2$CH$_2$ | 2-SCH$_2$CH$_2$F | 1 | 3-CF$_3$ | 0 |
| I-93 | OCH$_3$ | CH$_2$CH$_2$ | 2-SO$_2$CH$_2$CH$_2$F | 1 | 3-CF$_3$ | 0 |
| I-94 | OCH$_3$ | CH$_2$CH$_2$ | 2-SCH$_2$CF$_3$ | 1 | 3-CF$_3$ | 0 |
| I-95 | OCH$_3$ | CH$_2$CH$_2$ | 2-SO$_2$CH$_2$CF$_3$ | 1 | 3-CF$_3$ | 0 |
| I-96 | OCH$_3$ | OH | — | 1 | 3-CF$_3$ | 0 |
| I-97 | OCH$_3$ | OCH$_3$ | — | 1 | 3-CF$_3$ | 0 |
| I-98 | OCH$_3$ | OCH$_2$CH$_3$ | — | 1 | 3-CF$_3$ | 0 |
| I-99 | OCH$_3$ | O(CH$_2$)$_2$CH$_3$ | — | 1 | 3-CF$_3$ | 0 |
| I-100 | OCH$_3$ | OCH$_2$CH=CH$_2$ | — | 1 | 3-CF$_3$ | 0 |
| I-101 | OCH$_3$ | OCH$_2$C≡CH | — | 1 | 3-CF$_3$ | 0 |
| I-102 | OCH$_3$ | OCH$_2$ | 2-F | 1 | 3-CF$_3$ | 0 |
| I-103 | OCH$_3$ | OCH$_2$ | 1-SCH$_3$ | 1 | 3-CF$_3$ | 0 |

TABLE 7

| Comp. No. | R$^1$ | A$^1$ a) | Substituent X$^1$n on A$^1$ b) | p | Y$^1$m | Z |
|---|---|---|---|---|---|---|
| I-104 | OCH$_3$ | OCH$_2$ | 1-SO$_2$CH$_3$ | 1 | 3-CF$_3$ | 0 |
| I-105 | OCH$_3$ | OCH$_2$ | 1-OCH$_2$CH$_3$ | 1 | 3-CF$_3$ | 0 |
| I-106 | OCH$_3$ | OCH$_2$Ph | — | 1 | 3-CF$_3$ | 0 |
| I-107 | OCH$_3$ | OCH$_2$ | 1-cyclopropyl | 1 | 3-CF$_3$ | 0 |
| I-108 | OCH$_3$ | NHCH$_3$ | — | 1 | 3-CF$_3$ | 0 |
| I-109 | OCH$_3$ | N(CH$_3$)$_2$ | — | 1 | 3-CF$_3$ | 0 |
| I-110 | OCH$_3$ | N(CH$_2$CH$_3$)$_2$ | — | 1 | 3-CF$_3$ | 0 |
| I-111 | OCH$_3$ | NHPh | — | 1 | 3-CF$_3$ | 0 |
| I-112 | OCH$_3$ | NHCH$_2$Ph | — | 1 | 3-CF$_3$ | 0 |
| I-113 | OCH$_3$ | CHCH$_3$ | 1-CH$_3$ | 1 | 3-Cl | 0 |
| I-114 | OCH$_3$ | (CH$_2$)$_2$CH$_3$ | — | 1 | 3-Cl | 0 |
| I-115 | OCH$_3$ | CHCH$_3$ | 1-CH$_3$ | 1 | 3-CH$_3$ | 0 |
| I-116 | OCH$_3$ | (CH$_2$)$_2$CH$_3$ | — | 1 | 3-CH$_3$ | 0 |
| I-117 | OCH$_3$ | CHCH$_3$ | 1-CH$_3$ | 1 | 3-OCH$_3$ | 0 |
| I-118 | OCH$_3$ | (CH$_2$)$_2$CH$_3$ | — | 1 | 3-OCH$_3$ | 0 |

TABLE 7-continued

| Comp. No. | R$^1$ | A$^1$ a) | Substituent X$^1$n on A$^1$ b) | p | Y$^1$m | Z |
|---|---|---|---|---|---|---|
| I-119 | OCH$_3$ | CHCH$_3$ | 1-CH$_3$ | 1 | 3-SCH$_3$ | 0 |
| I-120 | OCH$_3$ | (CH$_2$)$_2$CH$_3$ | — | 1 | 3-SCH$_3$ | 0 |
| I-121 | OCH$_3$ | CHCH$_3$ | 1-CH$_3$ | 1 | 3-Br | 0 |
| I-122 | OCH$_3$ | (CH$_2$)$_2$CH$_3$ | — | 1 | 3-Br | 0 |

TABLE 8

| Comp. No. | R$^1$ | A$^1$ a) | Substituent X$^1$n on A$^1$ b) | p | Y$^1$m | Z |
|---|---|---|---|---|---|---|
| I-123 | OCH$_3$ | — | — | 0 | 3-CF$_3$ | 0 |
| I-124 | N(CH$_3$)$_2$ | — | — | 0 | 3-CF$_3$ | 0 |
| I-125 | N(CH$_3$)$_2$ | OH | — | 1 | 3-CF$_3$ | 0 |
| I-126 | OCH$_3$ | NHCCH$_3$ | 1,1-(CH$_3$)$_2$ | 1 | 3-CF$_3$ | 0 |
| I-127 | OCH$_3$ | CH$_2$ | 1-SO$_2$CH$_3$ | 1 | 3-CF$_3$ | 0 |

TABLE 9

| Comp. No. | R$^1$ | A$^1$, A$^1$ a) | X$^1$, X$^1$ b) | p | Y$^1$m | Z |
|---|---|---|---|---|---|---|
| I-200 | OCH$_3$ | CH$_2$CH$_3$, CH$_2$CH$_3$ | — — | 2 | 3-CF$_3$ | 0 |
| I-201 | OCH$_3$ | CH$_3$, CH$_2$CH$_3$ | — — | 2 | 3-CF$_3$ | 0 |
| I-202 | OCH$_3$ | CH$_3$, NHCH$_3$ | — — | 2 | 3-CF$_3$ | 0 |
| I-203 | OCH$_3$ | CH$_3$, OCH$_3$ | — — | 2 | 3-CF$_3$ | 0 |
| I-204 | OCH$_3$ | CH$_2$CH$_3$, NHCH$_2$CH$_3$ | — — | 2 | 3-CF$_3$ | 0 |
| I-205 | OCH$_3$ | CH$_2$CH$_3$, OCH$_2$CH$_3$ | — — | 2 | 3-CF$_3$ | 0 |

TABLE 10

| Comp. No. | R$^1$ | A$^1$, A$^1$ a) | X$^1$, X$^1$ b) | Linkage part of ring c) | p | Y$^1$m | Z |
|---|---|---|---|---|---|---|---|
| I-300 | OCH$_3$ | CH$_2$, CHCH$_3$ | —, — | — | 2 | 3-CF$_3$ | 0 |
| I-301 | OCH$_3$ | CH$_2$, CH$_2$CH$_2$ | —, — | — | 2 | 3-CF$_3$ | 0 |
| I-302 | OCH$_3$ | CH$_2$CH$_2$, CH$_2$CH$_2$ | —, — | — | 2 | 3-CF$_3$ | 0 |
| I-303 | OCH$_3$ | CH$_2$CH$_2$, CH$_2$CH$_2$ | —, 0 | 0 | 2 | 3-CF$_3$ | 0 |
| I-304 | OCH$_3$ | CH$_2$CH$_2$, CH$_2$CH$_2$ | —, N—CH$_3$ | N | 2 | 3-CF$_3$ | 0 | a): The symbol: "Ph" represents a phenyl group.

One of carbon atoms of CH$_2$CH$_2$ of the compound (I-35), which lacks in hydrogen atoms capable of bonding thereto, is bonded to a nitrogen atom of 2-CONH of pyridine, and the other carbon atom is bonded to (X$^1$)$_n$.

"2-Cl" indicates that chlorine is bonded to the 2-position carbon atom, assuming that the carbon atom in CH$_2$CH$_2$ which is bonded to the nitrogen atom of 2-CONH of pyridine, is located at the 1-position.

"CCH$_3$" of the compound (I-41) indicates that the carbon atom which lacks in hydrogen atoms capable of bonding thereto, is bonded to the nitrogen atom of 2-CONH of pyridine, and that the same carbon atom is also bonded to two CH$_3$ groups.

"OCH$_2$CH$_2$" of the compound (I-102) indicates that the oxygen atom which lacks in bonding number, is bonded to the nitrogen atom of 2-CONH of pyridine, and that the 2-position carbon atom which lacks in bonding number, is bonded to a fluorine atom.

"NHCCH$_3$" of the compound (I-126) indicates that the nitrogen atom which lacks in bonding number, is bonded to the nitrogen atom of 2-CONH of pyridine, and that the 1-position carbon atom which lacks in bonding number, is bonded to two methyl groups.

Thus, when A$^1$ is represented by carbon atoms and hydrogen atoms, the carbon atoms to be bonded to the nitrogen atom of 2-CONH of pyridine or (X$^1$)$_n$ are indicated in such a condition as being deficient in bonding number.

The "—" (em dash) means an unsubstituted condition (n=0).

b): The "—" (em dash) means an unsubstituted condition (n=0).

In the case where A$^1$ is Ph having substituents thereon, the number prefixed to the "-" (en dash) represents a bonding position of each substituent, and the name of each substituent and the number of 2 or more bonding positions, if any, are suffixed to the "-" (en dash).

In the compound (I-35), it is indicated that A$^1$ is CH$_2$CH$_2$ and "chloro" (chlorine atom) is bonded to the 2-position.

"4-Cl" of the compound (I-2) indicates that A$^1$ is Ph and only one Cl (chloro) is bonded to the 4-position thereof. "2,4-F$_2$" of the compound (I-14) indicates that two "fluoro" (fluorine atoms) are bonded to the 2- and 4-position thereof.

c): The "—" (em dash) means that the two alkyl chains are directly bonded each other to form a ring. In addition, "O" or "N" means that the ring is formed by interposing an oxygen atom or a nitrogen atom therein. For example, in the compound (I-300), it is indicated that carbon atoms of methyl and ethyl groups (represented as "CH$_2$" and "CHCH$_3$", respectively, in Table) bonded to a nitrogen atom of amide moiety of the carboxamide of which carbon atoms lack in bonding number, are directly bonded together to form a 3-membered ring.

In the compound (I-303), it is indicated that the ethyl group bonded to a nitrogen atom of amide moiety of the carboxamide and the ethyl group bonded to an oxygen atom (represented "CH$_2$CH$_2$" and "CH$_2$CH$_2$O", respectively, in Table) are bonded together through the carbon atom and the oxygen atom both of which lack in bonding number to form a 6-membered ring.

In the compound (I-304), it is indicated that the ethyl group bonded to a nitrogen atom of amide moiety of the carboxamide and the ethyl group bonded to a nitrogen atom of CH$_3$N (represented "CH$_2$CH$_2$" and "CH$_2$CH$_2$NCH$_3$", respectively, in Table) are bonded together through the carbon atom and the nitrogen atom both of which lack in bonding number to form a 6-membered ring.

Next, the process for producing the compound (I) is explained.

In the production process according to the present invention, the below-exemplified solvents can be usually used in reaction and separation steps thereof:

Aromatic hydrocarbons such as benzene, toluene, xylene, methyl naphthalene or the like; aliphatic hydrocarbons such as petroleum ethers, pentane, hexane, heptane, methyl cyclohexane or the like; halogenated hydrocarbons such as methylene chloride, chloroform, carbon tetrachloride, chlorobenzene or the like; amides such as dimethyl formamide, dimethyl acetamide, N-methyl-2-pyrrolidinone or the like; ethers such as diethyl ether, dimethoxy ethane, diisopropyl ether, tetrahydrofuran, diethylene glycol dimethyl ether (DIGLYM), dioxane or the like; carbon disulfide; acetonitrile; acetone; ethyl acetate; pyridine; dimethyl sulfoxide; hexamethylphosphoric amide; or the like {the above-mentioned organic solvents inclusive of from benzene to hexamethylphosphoric amide are occasionally herein referred to as "aprotic" solvents}.

As other usable solvents, there may be exemplified alcohols such as methanol, ethanol or the like; organic acids such as acetic acid, formic acid or the like; water; acetic anhydride; or the like.

These solvents may be used in the form of a mixture of any two or more thereof. All reaction steps of the production process according to the present invention can be advantageously carried out in the presence of either a solvent or a mixed solvent. In addition, there may be used a solvent composition containing solvents which are inhibited from forming a uniform layer when mixed with each other. In the case where such a solvent composition is used, it may be adequate to add to the reaction system a phase transfer catalyst, for example, ordinarily used quaternary ammonium salt or crown ether.

Further, in the case where a base is used in reaction and separation steps of the production process according to the present invention, there may be usually exemplified the following bases:

Alkali metals such as lithium, sodium, potassium or the like; alkali earth metals such as magnesium or the like; alkali metal alkoxides such as sodium methoxide, sodium ethoxide, potassium t-butoxide or the like; alkali metal hydrides such as sodium hydride, potassium hydride or the like; alkali metal carbonates such as potassium carbonate, sodium carbonate or the like; alkali earth metal carbonates such as calcium carbonate, barium carbonate or the like; alkali earth metal hydrides such as calcium hydride or the like; alkali metal hydroxides such as sodium hydroxide, potassium hydroxide or the like; alkali earth metal hydroxides such as calcium hydroxide, magnesium hydroxide or the like; alkali earth metal oxides such as magnesium oxide, calcium oxide or the like; organic metal compounds such as methyl lithium, ethyl lithium, butyl lithium, sec-butyl lithium, tert-butyl lithium, phenyl lithium or the like; Grignard reagents such as methyl magnesium iodide, ethyl magnesium bromide, n-butyl magnesium bromide or the like; organic copper compounds prepared by reacting organic alkali metal compounds or Grignard reagents with monovalent copper salts; or alkali metal amides such as lithium diisopropyl amide or the like. These bases may be used in the form of a mixture of any two or more thereof.

Furthermore, in the case where an acid is used in reaction and separation steps of the production process according to the present invention, as the acids, there may be usually exemplified inorganic acids such as hydrochloric acid, hydrobromic acid, hydroiodic acid, perchloric acid, sulfuric acid or the like; organic acids such as formic acid, acetic acid, butyric acid, p-toluene sulfonic acid or the like; Lewis acids such as boron trifluoride, aluminum chloride, zinc chloride or the like. These acids may be used in the form of a mixture of any two or more thereof.

Next, there is described the production process according to the second aspect of the present invention, which process comprises the step of forming a carbon-carbon bond between the metallized carbon atom of the compound (II) and the carbon atom of isocyanate group or isothiocyanate group of the compound (III) (hereinafter referred to merely as "step A").

That is, N-substituted-4-substituted-6-(substituted or unsubstituted) phenoxy-2-pyridine carboxamide or thiocarboxamide represented by the general formula (I-a), can be produced by subjecting 2-(metal-substituted)-4-substituted-6-(substituted or unsubstituted) phenoxy pyridine represented by the general formula (II) with substituted isocyanate (or isothiocyanate) represented by the general formula (III) to addition reaction; and then substituting a proton for the metal. The substitution of proton for the metal may be carried out by treating the obtained addition-reaction solution with an acidic aqueous solution.

The above reaction can be represented by the following reaction formula 1:

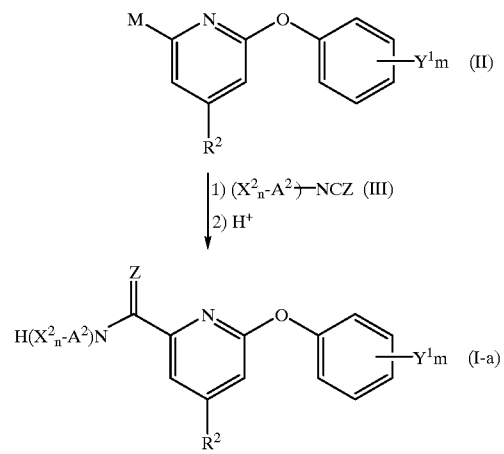

wherein $R^2$ is a $C_1$ to $C_4$ alkoxy group, a $C_1$ to $C_4$ alkylthio group, a di($C_1$ to $C_4$ alkyl)amino group or a ($C_1$ to $C_4$ alkyl)($C_7$ to $C_8$ aralkyl)amino group;

$A^2$ may be substituted with $X^2$, and is a $C_1$ to $C_{10}$ alkyl group, a $C_3$ to $C_6$ alkenyl group, a $C_3$ to $C_6$ alkynyl group, a $C_3$ to $C_6$ cycloalkyl group, a phenyl group or an arylalkyl group (whose alkyl moiety has 1 to 3 carbon atoms), {wherein the chain-like hydrocarbon moiety of $A^2$ is constituted by a longest carbon chain as a main chain exclusive of a $C_1$ to $C_4$ alkyl group bonded as side chain to the main chain and the $C_1$ to $C_4$ alkyl groups as side chains constitute $X^2$};

$X^2$ is a halogen atom, a $C_1$ to $C_4$ alkoxy group, a $C_1$ to $C_4$ alkylthio group, a $C_1$ to $C_4$ alkyl group (which is not bonded to a terminal position of $A^2$ when said $A^2$ is a $C_1$ to $C_{10}$ alkyl group), a $C_3$ to $C_6$ cycloalkyl group or a di($C_1$ to $C_4$ alkyl)amino group, wherein the alkyl moiety of $X^2$ may be substituted with halogen atom(s);

n is 0 or an integer selected from numbers of hydrogen atoms of $A^2$ which can be substituted with $X^2$, and when n is an integer of not less than 2, $X^2$s may be the same or different;

$Y^1$ is a $C_1$ to $C_4$ haloalkyl group, a $C_1$ to $C_4$ alkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom;

m is an integer of 0 to 5, and when m is an integer of not less than 2, $Y^1$s may be the same or different;

Z is an oxygen atom or a sulfur atom; and

M is an alkali metal, an alkali earth metal-Q wherein Q is a halogen atom, or ½(Cu-alkali metal).

The above-mentioned compound (II) can be readily produced by the method described hereinafter. In addition, as the above-mentioned compound (III), there may be used commercially available compounds or those capable of being produced by known or existing techniques.

Examples of these compounds are enumerated in Tables 11 and 12.

TABLE 11

Phenyl isocyanate; phenyl isothiocyanate; benzyl isocyanate; cyclohexyl isocyanate; 4-chlorophenyl isocyanate; 3-chlorophenyl isocyanate; 2-chlorophenyl isocyanate; 4-methylphenyl isocyanate; 3-methylphenyl isocyanate; 2-methylphenyl isocyanate; 4-methoxyphenyl isocyanate; 4-bromophenyl isocyanate; 4-(methylthio)phenyl isocyanate; 3-(trifluoromethyl)phenyl isocyanate

TABLE 12

4-fluorophenyl isocyanate; 3-fluorophenyl isocyanate; 2-fluorophenyl isocyanate; 2,4-difluorophenyl isocyanate; allyl isocyanate; methyl isothiocyanate; ethyl isothiocyanate; 2-chloroethyl isocyanate; n-propyl isocyanate; n-propyl isothiocyanate; i-propyl isocyanate; t-butyl isocyanate; n-butyl isocyanate; n-butyl isothiocyanate In the addition reaction for obtaining the compound (I-a), the amount of the compound (III) used is usually 0.5 to 2.5 moles, preferably 1.0 to 2.5 moles based on one mole of the compound (II). The reaction temperature is usually −100 to 150° C., preferably −80 to 80° C. The reaction time is usually in the range of from several minutes to 10 hours.

As solvents used in the above-mentioned addition reaction, there may be exemplified such solvents as suitably used in the reaction of isocyanate. Examples of these suitable solvents may include, usually, aliphatic hydrocarbons such as petroleum ethers, pentane, hexane, heptane or methyl cyclohexane; ethers such as diethyl ether, dimethoxy ethane, diisopropyl ether, tetrahydrofuran, diethylene glycol dimethyl ether (DIGLYM) or dioxane; aromatic hydrocarbons such as benzene, toluene, xylene or methyl naphthalene; or the like. These solvents may be used in the form of a mixture of any two or more thereof.

The substitution of proton for the metal may be carried out by treating the obtained addition reaction solution with an acid aqueous solution.

As the acids used in the above-mentioned substitution of proton for the metal, there may be usually exemplified inorganic acids such as hydrochloric acid, hydrobromic acid, hydroiodic acid, perchloric acid or sulfuric acid; organic acids such as formic acid, acetic acid, butyric acid or p-toluene sulfonic acid; or the like. These acids may be used in the form of a mixture of any two or more thereof.

The compound (I-a) obtained in the above-mentioned reaction may be separated by ordinary separation methods. For example, the reaction mixture is extracted with an organic solvent, and the solvent is distilled off to obtain a residue. The obtained residue is separated into components by column chromatography, and the resultant separated solution is concentrated and treated with lean solvent to obtain a precipitate. If required, the precipitate may be further purified by recrystallization.

As the solvents used in the above separation step, there may be usually exemplified aromatic hydrocarbons such as benzene, toluene, xylene or methyl naphthalene; aliphatic hydrocarbons such as petroleum ethers, pentane, hexane, heptane or methyl cyclohexane; halogenated hydrocarbons such as methylene chloride, chloroform, carbon tetrachloride or chlorobenzene; amides such as dimethyl formamide, dimethyl acetamide or N-methyl-2-pyrrolidinone; ethers such as diethyl ether, dimethoxy ethane, diisopropyl ether, tetrahydrofuran, diethylene glycol dimethyl ether (DIGLYM) or dioxane; or the like. As other usable solvents, there may be exemplified water, carbon disulfide, acetonitrile, ethyl acetate, dimethyl sulfoxide, hexamethylphosphoric amide or the like. These sovents may be used in the form of a mixture of any two or more thereof.

The compound (II) used in the above-mentioned step A may be produced by metalation of the compound represented by the general formula (XII). The compound (XII) may be produced by nucleophilically substituting one of halogen atoms of 2,6-dihalogeno-4-substituted pyridine represented by the general formula (XIII) with phenol represented by the general formula (XI).

This reaction can be shown by the following reaction formula 7:

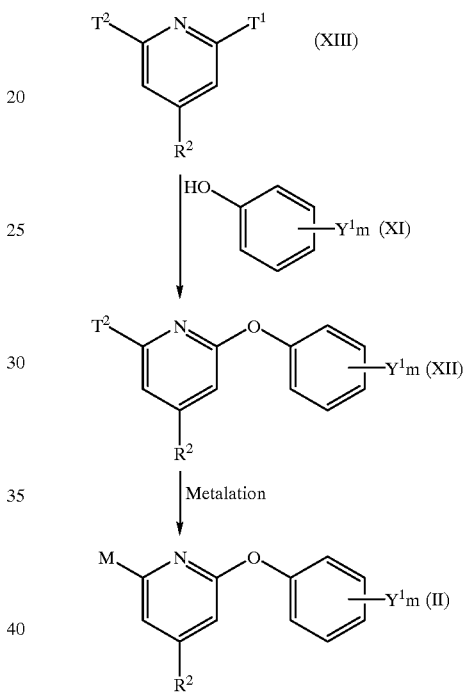

wherein $R^2$, $T^1$, $Y^1$, m and M have the same meanings as defined above, and $T^2$ represents a halogen atom.

As the above-mentioned compound (XI), there may be used commercially available compounds or those capable of being produced by known or existing techniques.

Examples of these compounds are enumerated in Table 13.

TABLE 13

3-chlorophenol; 3-methylphenol; 3-methoxyphenol; 3-(methylthio)phenol; 3-(trifluoromethyl)phenol; 3-(trifluoromethoxy)phenol; 3-(difluoromethoxy)phenol; 3-(trifluoromethylthio)phenol As the above-mentioned compound (XIII), there may also be used commercially available compounds or those capable of being produced by known or existing techniques.

As the halogen atoms represented by $T^1$ or $T^2$, there may be suitably used chlorine, bromine, iodine or the like. Among these compounds, 2,6-dichloro-4-methoxy pyridine {corresponding to the compound (XIII) wherein $T^1$ and $T^2$ are Cl and $R^2$ is $OCH_3$} or 2,6-dibromo-4-methoxy pyridine {corresponding to the compound (XIII) wherein $T^1$ and $T^2$ are Br and $R^2$ is $OCH_3$} have been respectively described in "J. Chem. Soc. B", 1967, (8), 758, "Chem. Ber.", 122(3), 589(1989) or the like. Further, 2,6-dihalogeno-4-(alkoxy, alkylamino or alkylthio) pyridine {corresponding to the compound (XIII) wherein $T^1$ and $T^2$ are halogen atoms and $R^2$ is a $C_1$ to $C_4$ alkoxy group, a $C_1$ to $C_4$ alkylamino group or a $C_1$ to $C_4$ alkylthio group} can be produced by nucleophilically substituting 2,6-dihalogeno-4-nitropyridine {corresponding to the compound (XIII) wherein $T^1$ and $T^2$ are halogen atoms and $R^2$ is a nitro group, which has been used as a raw compound} with $C_1$ to $C_4$ alkanol, $C_1$ to $C_4$ alkyl amine or $C_1$ to $C_4$ alkylthiol, under a basic condition.

Also, 2,6-dihalogeno-4-($C_1$ to $C_4$ alkyl)amino pyridine {corresponding to the compound (XIII) wherein $T^1$ and $T^2$ are halogen atoms and $R^2$ is a $C_1$ to $C_4$ alkylamino group} can be produced by nucleophilically substituting the nitrogen atom of $C_1$ to $C_4$ alkylamino group thereof with a halogenated ($C_1$ to $C_4$ alkyl) group or a halogenated ($C_1$ to $C_4$ aralkyl) group, under a basic condition, thereby converting the $C_1$ to $C_4$ alkylamino group into a di($C_1$ to $C_4$ alkyl)amino group or a $C_1$ to $C_4$ alkyl)($C_7$ to $C_8$ aralkyl) amino group.

Since one more nucleophilically substitutable halogen atom remains in the compound (XII) as a reaction intermediate, from the standpoint of yield of the compound (XII), it is preferred that less than 2 moles of the compound (XI) be reacted with one mole of the compound (XIII).

Accordingly, the compound (XI) is added in an amount of usually 0.5 to 1.5 moles, preferably 0.8 to 1.2 moles based on one mole of the compound (XIII) for the reaction therebetween. The base may be used in an equimolar amount to moles of the compound (XI) in the above-mentioned molar ratio.

Since the reaction rapidly proceeds under a basic condition, the degree of reaction can be usually controlled by varying the amount of the base used. Therefore, there may also be adopted such a method in which the amount of the base charged is adjusted to be identical to the above molar ratio of the compound (XI) to be charged, while the compound (XI) itself is used in an amount larger than that of the base.

From the viewpoint of facilitated separation of the compound (XII) as the aimed product, it is suitable to lessen the amount of compound (XI) remaining unreacted. Accordingly, it is preferred to use the compound (XI) in a molar amount identical to or slightly larger than that of the base used.

The reaction temperature is usually in the range of 0 to 250° C., preferably 60 to 180° C. The reaction time is in the range of from several minutes to several days.

Next, there will be described a method of producing the compound (II) by metalation of the compound (XII). As the solvents used in the reaction for producing the compound (II), there may be exemplified those solvents which can be suitably used to prepare organic metal compounds. Examples of these suitable solvents may include, usually, aliphatic hydrocarbons such as petroleum ethers, pentane, hexane, heptane, methyl cyclohexane or the like; ethers such as diethyl ether, dimethoxy ethane, diisopropyl ether, tetrahydrofuran, diethylene glycol dimethyl ether (DIGLYM), dioxane or the like; aromatic hydrocarbons such as benzene, toluene, xylene, methyl naphthalene or the like.

As metallizing reagents used for carrying out the metalation, there may be usually exemplified organic alkali metal compounds such as butyl lithium, sec-butyl lithium, tert-butyl lithium, methyl lithium, phenyl lithium or the like; alkali metals such as lithium, sodium, potassium or the like; alkali earth metals such as magnesium or the like. As the metallized compound (II), there may be used, for example, copper-containing compounds (II) {corresponding to the compound (II) wherein M is ½(Cu-alkali metal) or ½(Cu-alkali earth metal halogen)} prepared by reacting a compound of alkali metal such as lithium, sodium or potassium, preferably lithium {corresponding to the compound (II) wherein M is alkali metal, preferably lithium} or a Grignard reagent of the compound (II) {corresponding to the compound (II) wherein M is alkali earth metal-halogen} with a monovalent-copper salt such as copper iodide (CuI).

The amount of the metallizing reagent used is usually 0.5 to 3 moles, preferably 0.8 to 1.5 moles based on one mole of the compound (XII) in order to sufficiently react equivalent amounts of these compounds with each other. The reaction temperature is usually −100 to 150° C., preferably −80 to 80° C. The reaction time is from several minutes to several hours.

The production process according to the third aspect of the present invention comprises the step of forming a carbon-nitrogen bond between the carbon atom of carbonyl or thiocarbonyl group of the compound (IV) and the nitrogen atom of the compound (V) (hereinafter referred to merely as "step B").

That is, N-(substituted or unsubstituted)-4-substituted-6-(substituted or unsubstituted) phenoxy-2-pyridine carboxamide or thiocarboxamide represented by the general formula (I-b) can be produced by substituting a leaving group of the compound represented by the general formula (IV) with (substituted or unsubstituted) amine, (substituted or unsubstituted) hydroxyl amine or (substituted or unsubstituted) hydrazine represented by the general formula (V), usually in an organic solvent.

This reaction is shown by the following reaction formula 2:

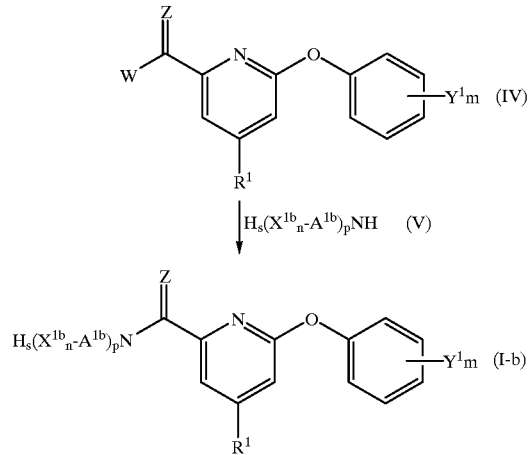

wherein $R^1$ is a $C_1$ to $C_4$ alkoxy group, a $C_1$ to $C_4$ alkylthio group, a $C_1$ to $C_4$ alkylamino group, a di($C_1$ to $C_4$ alkyl) amino group or a ($C_1$ to $C_4$ alkyl)($C_7$ to $C_8$ aralkyl)amino group;

$A^{1b}$ may be substituted with $X^{1b}$, and is a $C_1$ to $C_{10}$ alkyl group, a $C_2$ to $C_6$ alkenyl group, a $C_3$ to $C_6$ alkynyl group, a $C_3$ to $C_6$ cycloalkyl group, a $C_1$ to $C_{10}$ alkoxy group, a $C_3$ to $C_6$ alkenyloxy group, a $C_3$ to $C_6$ alkynyloxy group, a $C_1$ to $C_{10}$ alkylamino group, a di($C_1$ to $C_6$ alkyl)amino group, a phenyl group, a phenylamino group, an arylalkyl group (whose alkyl moiety has 1 to 3 carbon atoms), an arylalkyloxy group (whose alkyl moiety has 1 to 3 carbon atoms), an arylalkylamino group (whose alkyl moiety has 1 to 3 carbon atoms), an amino group or a hydroxyl group, {wherein the chain-like hydrocarbon moiety of $A^{1b}$ is constituted by a longest carbon chain as a main chain exclusive of a $C_1$ to $C_4$ alkyl group bonded as side chain to the main chain, and the $C_1$ to $C_4$ alkyl groups as side chains constitute $X^{1b}$};

$X^{1b}$ is a halogen atom, a $C_1$ to $C_4$ alkoxy group, a $C_1$ to $C_4$ alkylthio group, a $C_1$ to $C_4$ alkyl group (which is not bonded to a terminal position of $A^{1b}$ when the $A^{1b}$ is a $C_1$ to $C_{10}$ alkyl group, a $C_1$ to $C_{10}$ alkoxy group, a $C_1$ to $C_{10}$ alkylamino group or a di($C_1$ to $C_6$ alkyl)amino group), a $C_3$ to $C_6$ cycloalkyl group, a $C_1$ to $C_4$ alkylcarbonyl group, a $C_1$ to $C_4$ alkylamino group, a di($C_1$ to $C_4$ alkyl)amino group, a $C_1$ to $C_4$ alkylsulfonyl group, a $C_1$ to $C_4$ alkylsulfinyl group, a hydroxyl group, an amino group, a cyano group or a thiol group, wherein the alkyl moiety of $X^{1b}$ may be substituted with halogen atom(s);

n is 0 or an integer selected from numbers of hydrogen atoms of $A^{1b}$ which can be substituted with $X^{1b}$, and when n is an integer of not less than 2, $X^1$s may be the same or different;

p and s are an integer of 0 to 2 with the proviso that the sum of p and s (p+s) is 2; when p is 2, $A^{1b}$s may be the same or different; and when p is 2 and two $A^{1b}$s are alkyl chains, the $A^{1b}$s may be directly bonded together or may be bonded to each other through an oxygen atom of the hydroxyl group, or a nitrogen atom of the amino group or the $C_1$ to $C_4$ alkylamino group which groups are bonded to one of the two $A^{1b}$s, to form a ring;

$Y^1$ is a $C_1$ to $C_4$ haloalkyl group, a $C_1$ to $C_4$ alkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom;

m is an integer of 0 to 5, and when m is not less than 2, $Y^1$s may be the same or different;

Z is an oxygen atom or a sulfur atom; and

W is a leaving group.

The leaving group means a substituent bonded to a carbonyl or thiocarbonyl group of the compound (IV) which is substituted with the nitrogen atom of amine moiety of the compound (V) under the specific reaction conditions. As the suitable leaving groups, there may be exemplified halogen atoms such as chlorine atom, bromine atom or the like, alkoxy groups such as methoxy, ethoxy or the like; a hydroxyl group; or the like. Especially preferred leaving groups are halogen atoms. Among them, chlorine atom is more preferred.

In the case where W of the compound (IV) is a halogen atom, hydrogen halide tends to be disadvantageously generated in the course of the reaction for substituting the halogen atom using the compound (V) {when there is used such a compound (V) whose amine moiety is in the form of a salt such as hydrochloride, equimolar amount or more of a base such as triethyl amine is added thereto to form free amine}. Therefore, for the purpose of capturing the hydrogen halide, it is preferred that the compound (V) be added in such an excessive amount larger, e.g., not less than one equivalent, than that of the compound (IV). The amount of the compound (V) used is usually 2.0 moles to 10.0 moles, preferably 2.0 to 5.0 moles based on one mole of the compound (IV). Alternatively, instead of adding the excessive amount of the compound (V), there may be adopted a method of causing a base such as triethyl amine to co-exist in the reaction solution, thereby removing the hydrogen halide. In this case, the amount of the compound (V) used is usually 1.0 to 5.0 moles, preferably 1.0 to 3.0 moles based on one mole of the compound (IV).

In addition, in the case where the compound (V) has not less than two amine moieties capable of reacting with the compound (IV), there arises a disadvantage that the compound (I-b) produced is reacted again with the compound (IV). Further, in the case where the compound (V) used tends to generate hydrogen halide as a by-product, there also arises a disadvantage that the hydrogen halide is unsuitably reacted with the compound (I-b) produced. In these cases, it is preferred that the compound (V) be used in an excessive amount. The amount of the compound (V) used in such cases is usually 2.0 to 30.0 moles, preferably 2.0 to 15.0 moles based on one mole of the compound (IV).

The reaction temperature is usually 0 to 150° C., preferably 0 to 80° C. The reaction time is several minutes to about 20 hours.

When W of the compound (IV) is a lower alkoxy group, a base may be used. Alkyl amine, ammonia, etc. having a relatively high nucleophilic property can be substituted for the lower alkoxy group without using a base, under moderate conditions. On the other hand, in the case of aniline, etc. having a low nucleophilic property, a high temperature condition is required for the substitution. Therefore, the substitution is carried out in the absence of solvent or in the presence of a solvent having a high reflux temperature.

The reaction temperature is 0 to 250° C., preferably 0 to 180° C. The compound (V) is used in an excessive amount relative to that of the compound (IV). The amount of the compound (V) used is usually 1.0 to 100 moles, preferably 1.0 to 10 moles based on one mole of the compound (IV).

Under the condition using a base, in the case where the amine is converted into alkali amide using the base and the alkali amine is subjected to the reaction, the above-mentioned high temperature condition is not necessarily required to proceed the reaction. The reaction temperature is 0 to 150° C., preferably 0 to 100° C. The reaction time is several minutes to several days.

It is not necessary that the compound (V) is added in an excessive amount relative to the compound (IV). The amount of the compound (V) used is usually 1.0 to 5.0 moles, preferably 1.0 to 3.0 moles based on one mole of the compound (IV). The amount of the base used is usually 1.0 to 3.0 moles, preferably 1.0 to 2.0 moles based on one mole of the compound (IV).

In the case where W of the compound (IV) is a hydroxyl group, the reaction is usually carried out by using an excessive amount of the compound (V) and subjecting the compounds together with a solvent such as toluene or benzene to azeotropic dehydration which is conducted under reflux while heating, or a large excessive amount of amines is reacted therewith in the absence of a solvent. The reaction temperature is usually 30 to 300° C., preferably 50 to 200° C. In this case, the amount of the compound (V) used is usually 1.0 to 100 moles, preferably 1.0 to 10 moles based on one mole of the compound (IV). Also, in the case where a dehydrating agent such as carbodiimide is used, the above-mentioned high temperature is not required. The reaction temperature in the presence of a solvent is usually 0 to 120° C., preferably 0 to 80° C. The amount of the compound (V) used is usually 1.0 to 20 moles, preferably 1.0 to 10 moles based on one mole of the compound (IV). the reaction time is several minutes to several days. (substituted or unsubstituted) amines, (substituted or unsubstituted) hydroxyl amine, or (substituted or unsubstituted) hydrazine as the compound (V) used in the present invention (wherein $X^{1b}$, $A^{1b}$, n, s and p have the same meanings as defined above) may include commercially available products, or those which can be produced by known techniques. As the unsubstituted amines, hydroxyl amines or hydrazine, there may be exemplified ammonia, hydroxyl amine or hydrazine. Among the substituted amines, examples of the substituted primary amines may include alkyl amines such as methyl amine, ethyl amine, propyl amine, 2-(methyl)ethyl amine or the like; alkenyl amines such as allyl amine or the like; alkynyl amines such as propargyl amine, 1,1-dimethylpropargyl amine or the like; cycloalkyl amines such as cyclopropyl amine, cyclobutyl amine, cyclohexyl amine or the like; haloalkyl amines such as 2,2,2-trifluoroethyl amine, 2,2,3,3,3-pentafluoropropyl amine, 2,2,3,3,4,4,4-heptafluorobutyl amine, 2-fluoroethyl amine, 2-chloroethyl amine, 2-bromoethyl amine, 3-chloropropyl amine or the like; alkoxylalkyl amines such as 2-(ethoxy)ethyl amine, 3-(methoxy)propyl amine or the like; alkylthioalkyl amines such as 2-(ethylthio)ethyl amine, 3-(methylthio)propyl amine or the like; hydroxyalkyl amines such as ethanol amine, 2-amino-1-propanol, 3-amino-1-propanol or the like; mercapto-substituted alkyl amines such as 2-aminoethane thiol or the like; aniline, halogen-substituted anilines such as 2-chloroaniline, 4-bromoaniline or the like; alkyl-substituted anilines such as 4-methyl aniline, 4-ethyl aniline or the like; alkoxy-substituted anilines such as 4-methoxy aniline, 3-ethoxy aniline or the like; alkylthio-substituted anilines such as 4-(methylthio)aniline, 3-(methylthio)aniline or the like; haloalkyl-substituted anilines such as 3-(trifluoromethyl)aniline, 4-(trifluoromethyl)aniline or the like; haloalkoxy-substituted anilines such as 3-(trifluoromethoxy)aniline, 4-(trifluoromethoxy)aniline or the like; phenylalkyl amines such as benzyl amine or the like. In addition, there may also be used amines obtained by reduction of nitrile compounds or nitro compounds.

Further, there may also be used amines obtained by removing a protecting group such as phthalic acid or the like from N-substituted phthalimide or N-substituted amides prepared by reacting carboxamides such as phthalimide, benzamide or the like with the below-mentioned substituted halogen compounds, substituted dialkyl sulfate compounds, substituted sulfonate compounds or the like.

Furthermore, there may also be used amines obtained by subjecting compounds prepared by reacting amines with dicarboxylic anhydrides such as phthalic anhydride or acyl halides to protect the amino group, to various known modification reactions, for example, a substitution reaction in which the halogen atom of $X_{1b}$ is nucleophilically substituted with $C_1$ to $C_4$ alkanol or $C_1$ to $C_4$ alkylthiol under a basic condition, or an oxidation reaction in which sulfur atom, etc., is oxidized, and removing the protecting group from the modified compounds.

As the secondary amines and cyclic amines, there may also be used commercially available products or those compounds which can be produced by known techniques.

As the secondary amines, there may be exemplified the following compounds:

compounds {corresponding to compounds (V) wherein s is 0; p is 2; both of $A^{1b}$s are $C_1$ to $C_{10}$ alkyl groups; and n is 0 ($A^{1b}$ is unsubstituted with $X^{1b}$)} such as dimethyl amine, diethyl amine, dipropyl amine, dibutyl amine, N-ethylmethyl amine or the like (In these dialkyl amines, the $A^{1b}$s may be the same or different. These dialkyl amines are preferably di($C_1$ to $C_6$ alkyl)amines, more preferably di($C_1$ to $C_4$ alkyl)amines.);

compounds {corresponding to compounds (V) wherein s is 0; p is 2; one of $A^{1b}$s is $C_1$ to $C_{10}$ alkyl group and the other of $A^{1b}$s is $C_1$ to $C_{10}$ aralkyl group whose alkyl moiety has 1 to 3 carbon atoms; and n is 0 ($A^{1b}$ is unsubstituted with $X^{1b}$)} such as N-ethylbenzyl amine, N-methylbenzyl amine or the like (These alkyl(aralkyl) amines are preferably ($C_1$ to $C_6$ alkyl)phenyl ($C_1$ to $C_3$ alkyl)amines, more preferably ($C_1$ to $C_4$ alkyl)phenyl ($C_1$ to $C_2$ alkyl)amines.); and compounds {corresponding to compounds (V) wherein s is 0; p is 2; one of $A^{1b}$s is $C_1$ to $C_{10}$ alkyl group and the other of $A^{1b}$s is phenyl group; and n is 0 ($A^{1b}$ is unsubstituted with $X^{1b}$)} such as N-ethyl aniline, N-methyl aniline or the like (These alkyl(phenyl) amines are preferably ($C_1$ to $C_6$ alkyl)(phenyl)amines, more preferably ($C_1$ to $C_4$ alkyl)(phenyl)amines.).

As the cyclic secondary amines, there may be exemplified the following compounds:

compounds {corresponding to compounds (V) wherein s is 0; p is 2; both of $A^{1b}$s are $C_1$ to $C_{10}$ alkyl groups; n is 0 ($A^{1b}$ is unsubstituted with $X_{1b}$); and carbon atoms of the respective $A^{1b}$s which lack in bonding number, are directly bonded together to form a ring} such as propylene imine, azetidine, pyrrolidine, piperidine, 2-methyl piperidine, 3-methyl piperidine or the like;

compounds {corresponding to compounds (V) wherein s is 0; p is 2; both of $A^{1b}$s are $C_1$ to $C_{10}$ alkyl groups; and the carbon atom of one of $A^{1b}$s and the oxygen atom of $X^{1b}$ (=hydroxyl) bonded to the other of $A^{1b}$s are bonded together to form a ring through the oxygen atom} such as morpholine, 2,6-dimethyl morpholine or the like; and compounds {corresponding to compounds (V) wherein s is 0; p is 2; both of $A^{1b}$s are $C_1$ to $C_{10}$ alkyl groups; and the carbon atom of one of $A^{1b}$s and the nitrogen atom of $X^{1b}$ (=amino or $C_1$ to $C_4$ alkylamino) bonded to the other of $A^{1b}$s, are bonded together to form a ring through the nitrogen atom} such as piperazine, N-methyl piperazine or the like.

These cyclic secondary amines constitute preferably 3- to 10-membered ring, more preferably 3- to 6-membered ring.

Next, there will be described substituted hydroxyl amines. As the substituted hydroxyl amines, there may be exemplified various commercially available O-substituted or N-substituted hydroxyl amine compounds such as methoxyl amine, ethoxyl amine, allyloxyl amine, methoxylmethyl amine, phenylmethoxyl amine, N-methylhydroxyl amine or N-phenylhydroxyl amine. The substituted hydroxyl amines can also be produced by various known techniques, for example, by reacting an acyl-substituted compound such as N-hydroxyphthalimide, benzo-hydroxamic acid or the like with the below-mentioned substituted halogen compounds, substituted dialkyl sulfate compounds, substituted sulfonate compounds or the like, and removing the protecting group form the obtained compounds.

Further, there will be described substituted hydrazine compounds. As the substituted hydrazine compounds, there may be exemplified various commercially available substituted hydrazine compounds such as methyl hydrazine, 1,1-dimethyl hydrazine, 1,2-dimethyl hydrazine, 1,2-diethyl hydrazine, 2-chlorophenyl hydrazine, 3-chlorophenyl hydrazine, 4-chlorophenyl hydrazine, 2-methylphenyl hydrazine, 3-methoxyphenyl hydrazine, 3-(trifluoromethyl) phenyl hydrazine or the like. The substituted hydrazines can be produced by various known techniques, for example, by reacting an acyl-substituted hydrazine compound such as benzoyl-substituted hydrazine with the below-mentioned substituted halogen compound, substituted dialkyl sulfate compound, substituted sulfonate compound or the like and removing a protecting group from the resultant substituted amide compound; by reducing an N-acyl hydrazine compound; by reacting an azine compound with the above-mentioned alkylating reagent, followed by hydrolysis of the resultant compound; by reacting amines with hydroxyl amine-O-sulfonic acid or O-sulfonyl, or O-acyl hydroxyl amine; or the like. The thus produced substituted hydrazines may also be used in the present invention.

As the compound (IV) which is a raw material of the compound (I-b), there may be used the following compounds.

Especially preferred compounds may include 4-substituted-6-(substituted or unsubstituted) phenoxy-2-picolinic halide or thiopicolinic halide (IV-a).

In addition, there may also be used 4-substituted-6-(substituted or unsubstituted) phenoxy-2-picolinic acid lower alkyl ester or thiopicolinic acid lower alkyl ester (IV-b).

Further, there may also be used 4-substituted-6-(substituted or unsubstituted)phenoxy-2-picolinic acid (IV-c).

The processes for producing the respective compounds are described hereinafter.

First, the process for producing 4-substituted-6-(substituted or unsubstituted) phenoxy-2-picolinic chloride or thiopicolinic chloride (IV-a), is described below.

The above-mentioned compound (IV-a) can be produced by halogenating a 4-substituted-6-(substituted or unsubstituted) phenoxy-2-picolinic acid compound or a thiopicolinic acid compound (XIV-a) using a halogenating reagent such as thionyl chloride, phosphoryl chloride, phosphorous pentachloride, phosphorous trichloride or phosphoryl bromide.

This reaction process can be represented by the following reaction formula 8:

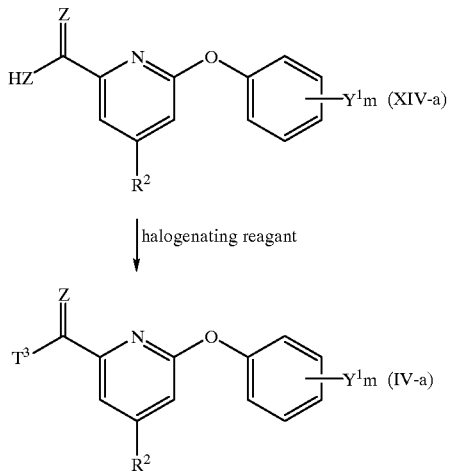

wherein $R^2$, Z, $Y^1$ and m have the same meanings as defined above, and $T^3$ represents a halogen atom.

As to the production conditions, the reaction can be conducted in the presence of a solvent inert to (thio)acid halide, such as benzene or toluene, at a temperature of 0 to 250° C., preferably 30 to 150° C.

The amount of the halogenating reagent used is usually 0.3 to 10 moles, preferably 1 to 5 moles based on one mole of the compound (XVI-a).

In addition, it is preferred to use an reaction accelerator such as dimethyl formamide or the like. The reaction time is usually several minutes to several days.

4-substituted-6-(substituted or unsubstituted) phenoxy-dithiopicolinic acid {corresponding to compound (XIV-a) wherein Z is S} or 4-substituted-6-(substituted or unsubstituted) phenoxy-picolinic acid {corresponding to compound (IV-c) wherein Z is O} which is used as a raw material immediately before the step B {step for producing the compound (I-b)}, can be produced in the following manner.

In the first method, the compound (XIV-a) can be produced by adding the compound (II) to carbon dioxide or carbon disulfide and then substituting a proton for the metal. This reaction can be represented by the following reaction formula 9:

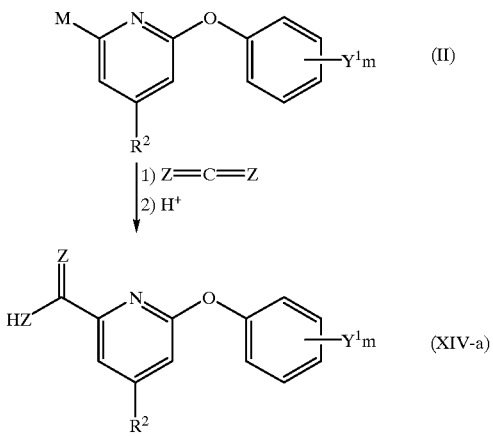

wherein $R^2$, M, $Y^1$, Z and m have the same meanings as defined above.

As to the production conditions, after the compound (II) is added to isocyanate, there can be used the conditions used for producing the compound (I-a) by proton substitution.

Incidentally, the production conditions described in the present specification, may include kind of solvent, reaction temperature, reaction time, kinds of reaction assistants (including acid, base, metallizing reagent, halogenating reagent or the like), amounts of these solvents and reagents or the like.

In the second method, the compound (XIV-b) can be produced by hydrolysis of 4-substituted-6-substituted-2-(substituted or unsubstituted) phenoxy pyridine {compound (XV)}. This reaction is represented by the following reaction formula 10:

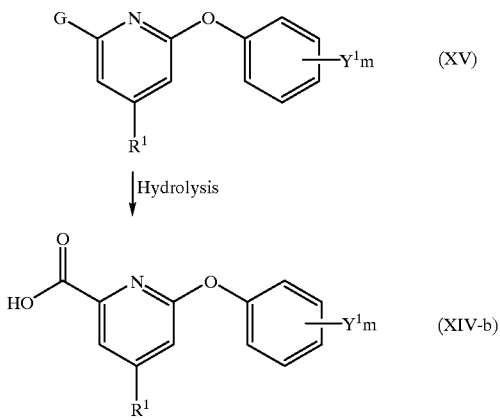

wherein $R^1$, $Y^1$ and m have the same meanings as defined above; G is a cyano group or a lower alkoxycarbonyl group.

The above-mentioned hydrolysis can be conducted under either acidic or basic conditions. In the case where the hydrolysis is conducted under acid conditions, as catalysts therefor, there may be usually used inorganic acids such as hydrochloric acid, hydrobromic acid or sulfuric acid. As solvents, water or water containing an organic acid such as acetic acid may be usually used. In the case where the hydrolysis is conducted under basic conditions, as the bases, there may be usually used alkali metal bases such as sodium hydroxide or potassium hydroxide. As solvents, water or water containing alcohols may be usually used. The hydrolysis temperature is usually in the range of from 20° C. up to reflux temperature, preferably from 50° C. up to the reflux temperature. The reaction time is several minutes to several days.

The compound (XV) used as a raw material in the step of the reaction formula 10 can be produced by nucleophilic substitution reaction between (substituted or unsubstituted) phenol represented by the formula (XI) and a halogen atom ($T^1$) of 4-substituted-6-substituted-2-halogenopyridine {compound (XVI)} under basic conditions. This reaction is represented by the following reaction formula 11.

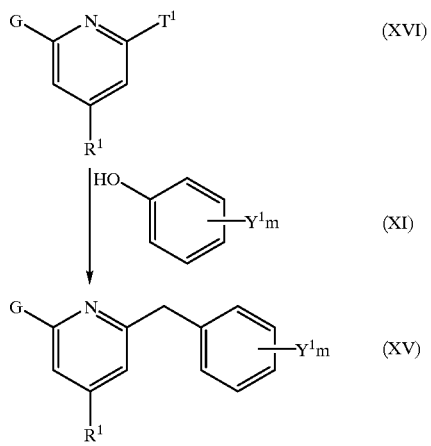

wherein $R^1$, $T^1$, G, $Y^1$ and m have the same meanings as defined above.

As the production conditions for the above reaction, there can be used conditions used in the below-mentioned step F for producing the compound (I-f) by phenoxylating the compound (X) with (substituted or unsubstituted) phenol (XI).

4-substituted-6-substituted-2-halogenopyridine {compound (XVI)} used for the production of the compound (XV) can be produced in the following manner.

4-substituted-2-cyano-6-halogenopyridine {compound (XVI) wherein G is CN} can be obtained by the following method.

2-cyano-6-chloro-4-substituted pyridine {compound (XVI) wherein $T^1$ is Cl; G is CN; and $R^1$ is a $C_1$ to $C_4$ alkoxy group, a $C_1$ to $C_4$ alkylamino group, a di($C_1$ to $C_4$ alkyl)amino group, a ($C_1$ to $C_4$ alkyl)($C_7$ to $C_8$ aralkyl) group or a $C_1$ to $C_4$ alkylthio group} is produced by nucleophilically substituting 2-cyano-4,6-dichloropyridine obtained by chlorinating 2-cyanopyridine with $C_1$ to $C_4$ alkanol, $C_1$ to $C_4$ alkylamine, di($C_1$ to $C_4$ alkyl)amine, ($C_1$ to $C_4$ alkyl)($C_7$ to $C_8$ aralkyl)amine or $C_1$ to $C_4$ alkylthiol under basic conditions.

The alkylamino group bonded to the 4-position of the compound (XVI) wherein $T^1$ is Cl; G is CN; and $R^1$ is a $C_1$ to $C_4$ alkylamino group, can be converted into a 4-di($C_1$ to $C_4$ alkyl)amino group or a 4-($C_1$ to $C_4$ alkyl)($C_7$ to $C_8$ aralkyl)amino group by nucleophilically substituting halogenated $C_1$ to $C_4$ alkyl and halogenated $C_7$ to $C_8$ aralkyl therewith under basic conditions.

Further, 2-cyano-4-methoxy-6-chloropyridine {compound (XVI) wherein $T^1$ is Cl; G is CN; and $R^1$ is $OCH_3$} is produced by alkylating an N-oxide moiety of 2-chloro-4-methoxypyridine N-oxide with dimethyl sulfate and then treating the obtained alkylated compound with sodium cyanide.

Next, 6-halogeno-4-substituted picolinic lower alkyl ester {compound (XVI) wherein G is a lower-alkoxy carbonyl group} can be obtained by the following method.

6-chloro-4-substituted picolinic lower alkyl ester {compound (XVI) wherein $T^1$ is Cl; G is a lower-alkoxy carbonyl group; and $R^1$ is a $C_1$ to $C_4$ alkoxy group, a $C_1$ to $C_4$ alkylamino group, a di($C_1$ to $C_4$ alkyl)amino group, a ($C_1$ to $C_4$ alkyl)($C_7$ to $C_8$ aralkyl) group or a $C_1$ to $C_4$ alkylthio group} can be produced by nucleophilically substituting 4,6-dichloropicolinic acid lower alkyl ester with $C_1$ to $C_4$ alkanol, $C_1$ to $C_4$ alkylamine, di($C_1$ to $C_4$ alkyl)amine, ($C_1$ to $C_4$ alkyl)($C_7$ to $C_8$ aralkyl)amine or $C_1$ to $C_4$ alkylthiol under basic conditions.

4,6-dichloropicolinic acid lower alkyl ester as a raw compound may be produced by treating 4,6-dichloropicolinic acid (for example, prepared by oxidizing 4,6-dichloro-2-methyl pyridine) with a halogenating reagent such as thionyl chloride to form an acid halide and then reacting the obtained acid halide with lower alkanol.

Further, the alkylamino group bonded to the 4-position of the compound (XVI) wherein $T^1$ is Cl; G is a lower alkoxy carbonyl group; and $R^1$ is a $C_1$ to $C_4$ alkylamino group, can be converted into a 4-di($C_1$ to $C_4$ alkyl)amino group or a 4-($C_1$ to $C_4$ alkyl)($C_7$ to $C_8$ aralkyl)amino group by nucleophilically substituting halogenated $C_1$ to $C_4$ alkyl and halogenated $C_7$ to $C_8$ aralkyl therewith under basic conditions.

4-substituted-6-(substituted or unsubstituted) phenoxy-2-picolinic acid lower alkyl ester {compound (XV) wherein G is lower alkoxy carbonyl} and 4-substituted-6-(substituted or unsubstituted) phenoxy-2-picolinic acid (XIV-b) can be used as a raw material for the step B {compound (IV) wherein Z is O; and W is OB or OH wherein OB represents lower alkoxy}.

4-substituted-6-(substituted or unsubstituted) phenoxy-2-picolinic acid lower alkyl ester or thiopicolinic acid lower alkyl ester {compound (IV-b)} can also be produced by reacting 4-substituted-6-(substituted or unsubstituted) phenoxy-2-picolinic halide {compound (IV-a)} with lower alkanol. This reaction is represented by the following reaction formula 12.

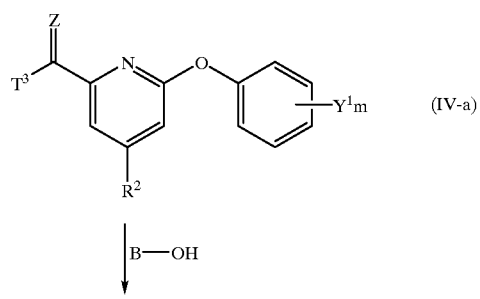

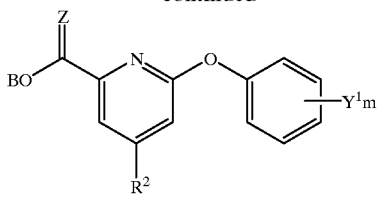

wherein $R^2$, $Y^1$, $Z$, $T^3$ and m have the same meanings as defined above; and B is a lower alkyl group.

This esterification reaction can be carried out by reacting the compound (IV-a) as an acid halide with lower alkanol, preferably in an inert solvent such as ether or benzene under the co-existence of a base such as triethyl amine or diethyl amine.

In the foregoing, there are described processes for producing the compound (IV) used in the step B.

The production process according to the fourth aspect of the present invention comprises a step of forming a nitrogen-carbon bond between the nitrogen atom of amide moiety of the compound (VI) and the carbon atom of the compound (VII-a) (hereinafter referred to merely as "step C").

That is, N-substituted-4-substituted-6-(substituted or unsubstituted) phenoxy-2-pyridine carboxamide or thiocarboxamide represented by the general formula (I-c) can be produced by reacting N-(substituted or unsubstituted)-4-substituted-6-(substituted or unsubstituted) phenoxy-2-pyridine carboxamide or thiocarboxamide represented by the general formula (VI) with a compound represented by the general formula (VII-a), usually in an aprotic organic solvent.

This reaction is expressed by the following reaction formula 3.
Reaction Formula 3:

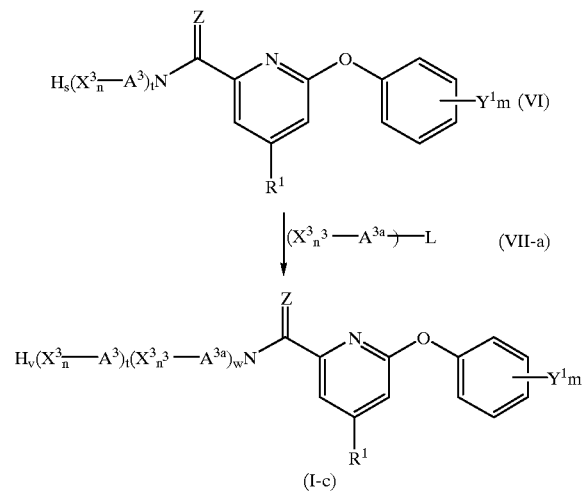

wherein $R^1$ is a $C_1$ to $C_4$ alkoxy group, a $C_1$ to $C_4$ alkylthio group, a $C_1$ to $C_4$ alkylamino group, a di($C_1$ to $C_4$ alkyl) amino group or a ($C_1$ to $C_4$ alkyl)($C_7$ to $C_8$ aralkyl)amino group;

$A^3$ may be substituted with $X^3$, and is a $C_1$ to $C_{10}$ alkyl group, a $C_3$ to $C_6$ alkenyl group, a $C_3$ to $C_6$ alkynyl group, a $C_3$ to $C_6$ cycloalkyl group, a $C_1$ to $C_{10}$ alkoxy group, a $C_3$ to $C_6$ alkenyloxy group, a $C_3$ to $C_6$ alkynyloxy group, a di($C_1$ to $C_6$ alkyl)amino group, a phenyl group, an arylalkyl group (whose alkyl moiety has 1 to 3 carbon atoms) or an arylalkyloxy group (whose alkyl moiety has 1 to 3 carbon atoms) {wherein the chain-like hydrocarbon moiety of $A^3$ is constituted by a longest carbon chain as a main chain exclusive of a $C_1$ to $C_4$ alkyl group bonded as side chain to the main chain, and the $C_1$ to $C_4$ alkyl groups as side chains constitute $X^3$};

$A^{3a}$ may be substituted with $X^3$, and is a $C_1$ to $C_{10}$ alkyl group, a $C_3$ to $C_6$ alkenyl group, a $C_3$ to $C_6$ alkynyl group, a $C_3$ to $C_6$ cycloalkyl group or an arylalkyl group (whose alkyl moiety has 1 to 3 carbon atoms) {wherein the chain-like hydrocarbon moiety of $A^{3a}$ is constituted by a longest carbon chain as a main chain exclusive of side chains, and the side chains constitute $X^3$};

$X^3$ is a halogen atom, a $C_1$ to $C_4$ alkoxy group, a $C_1$ to $C_4$ alkylthio group, a $C_1$ to $C_4$ alkyl group (which is not bonded to terminal positions of $A^3$ and $A^{3a}$ when the $A^3$ and $A^{3a}$ are a $C_1$ to $C_{10}$ alkyl group, a $C_1$ to $C_{10}$ alkoxy group or a di($C_1$ to $C_6$ alkyl)amino group), a $C_3$ to $C_6$ cycloalkyl group, a $C_1$ to $C_4$ alkylamino group, a di($C_1$ to $C_4$ alkyl)amino group, a $C_1$ to $C_4$ alkylsulfonyl group, a $C_1$ to $C_4$ alkylsulfinyl group or a cyano group wherein the alkyl moiety of $X^3$ may be substituted with halogen atom(s);

n and $n^3$ are 0 or an integer selected from numbers of hydrogen atoms of $A^3$ and $A^{3a}$ which can be substituted with $X^3$, and when n and $n^3$ are an integer of not less than 2, $X^3$s may be the same or different;

v is 0 or 1, t is 0 or 1, and w is 1 or 2 with the proviso that the sum of t and v (t+v) is 0 or 1 and the sum of t, v and w (t+v+w) is 2; and when w is 2, $A^{3a}$s may be the same or different;

$Y^1$ is a $C_1$ to $C_4$ haloalkyl group, a $C_1$ to $C_4$ alkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom;

m is an integer of 0 to 5, and when m is not less than 2, $Y^1$s may be the same or different;

Z is an oxygen atom or a sulfur atom; and

L is a leaving group.

In the reaction between the compounds (VI) and (VII-a), the leaving group (L) of the compound (VII-a) is nucleophilically substituted with the nitrogen atom of amide moiety of the compound (VI), thereby producing the compound (I-c). In the above-mentioned reaction, the compounds (VI) and (VII-a) are usually reacted with each other under basic conditions. The amount of the compound (VII-a) used is usually 0.8 to 10 moles, preferably 1.0 to 5 moles based on one mole of the compound (VI).

The amount of the base used is described below. In the case of the compound (VI) wherein s is 2, two substitutable hydrogen atoms are present on the nitrogen atom of carboxamide moiety thereof. Therefore, when it is aimed to obtain the compound (I-c) wherein v is 1, with a high yield, it is disadvantageous to use the base in such a molar amount largely exceeding that of the compound (VI). Accordingly, it is preferred that the base is used in a slightly excessive molar amount relative to that of the compound (VI). The amount of the base used is usually 0.8 to 1.5 moles, preferably 1.0 to 1.2 moles based on one mole of the compound (VI).

In the case of the compound (VI) wherein s is 1, since only one substitutable hydrogen atom is present on the nitrogen atom of the carboxamide, the base can be used in such an excessive amount exceeding the corresponding molar amount of the compound (VI).

In the above case, the amount of the base is usually 0.8 to 5 moles, preferably 1.0 to 3 moles based on one mole of the compound (VI). The reaction temperature is usually 0 to 200° C., preferably 10 to 150° C. The reaction time is several minutes to about 24 hours.

As the above-mentioned compound (VII), there can be used commercially available products or compounds producible by known techniques.

As the compounds (VII-a) used in the present invention, there may be exemplified substituted halides (compounds wherein L is a halogen atom; examples of the halogen atom may include chlorine atom, bromine atom, iodine atom or the like), substituted dialkyl sulfate compounds (compounds wherein L is a substituted sulfate), substituted sulfonate compounds (compounds wherein L is a substituted sulfonate) or the like.

Examples of the substituted halides may include halogenated alkyls such as 1-chloropropane, 2-chlorobutane, bromomethane, bromoethane, 1-bromopropane, 2-bromopropane, 1-bromobutane, iodomethane, iodoethane, 1-iodopropane, 1-bromo-2-fluoroethane, 1,3-dibromopropane, trifluoromethyl iodide, 1-iodo-2,2,2-trifluoroethane, 1-iodo-2,2,3,3,3-pentafluoropropane or the like; halogenated alkenyls such as allyl halide, 2-(methyl)allyl chloride, 2-bromo-2-butene, 4-bromo-1-butene, 1-bromo-2-methylpropene, 3-bromo-2-methyl propene, crotyl bromide, 1,4-dibromo-2-butene or the like; halogenated alkynyls such as propargyl bromide or the like; (halogenated alkoxy) alkyls such as 2-chloromethyl ethyl ether or the like; (halogenated alkylthio) alkyls such as (methylthio)methyl chloride or the like; (cycloalkyl)alkyl halides such as cyclopropylmethyl bromide, cyclohexylmethyl bromide or the like; halogenated cycloalkyls such as cyclohexyl iodide or the like; (substituted or unsubstituted) phenylalkyl halides such as phenylmethyl bromide, 4-chlorobenzyl chloride, 4-methylbenzyl chloride or the like; or various other halides.

As the substituted dialkyl sulfate compounds, there may be exemplified commercially available dimethyl sulfate, diethyl sulfate, dibutyl sulfate or the like; substituted dialkyl sulfate compounds commercially available or producible by known techniques which are produced by reacting various substituted alcohols (for example, alcohols such as methanol, ethanol, propanol or the like; alkoxy-substituted alcohols such as 2-methoxy ethanol, 2-ethoxy ethanol, 3-methoxy propanol or the like; alkylthio-substituted alcohols such as 2-methylthio ethanol, 2-ethylthio ethanol, 3-methylthio propanol or the like;

halogen-substituted alcohols such as 2,2,2-trifluoroethanol, 2,2,3,3,3-pentafluoropropanol or the like; dialkylamino-substituted alcohols such as 2-dimethylaminoethanol or the like) with, e.g., surfuryl chloride or fuming sulfuric acid; substituted sulfonate compounds commercially available or producible by known techniques which are produced by reacting the above-mentioned alcohols with substituted sulfonyl chloride (for example, paratoluene sulfonyl chloride, etc.); or the like.

As the compounds (VI) used as a raw material in the step C, there can be used the following compounds:

Compounds (I-a) as a reaction product in the step A;
Compounds (I-b) as a reaction product in the step B;
Compounds (I-c) wherein v is 1, as a reaction product in the step C;
Compounds (I-d) as a reaction product in the step D;
Compounds (I-e) as a reaction product in the step E;
Compounds (I-f) as a reaction product in the step F; and Compounds derived from the compounds (I-a) to (I-f), for example, compound (I-g) as a product obtained by hydrogenolysis thereof, compound (I-i) as a product obtained by oxidation of sulfide bond, or the like.

Further, the compound (I) {wherein $(A^1-X^1_n)$ is $CH=CX^{11}X^{12}$; s is 1; and p is 1} can be produced by the following production method using the formation of nitrogen-carbon bond, which is a similar method to the above-mentioned step C (step of producing the compound (I-c) using the formation of nitrogen-carbon bond on the nitrogen atom of carboxamide}.

That is, the compound (I) (wherein s is 2) and (substituted or unsubstituted)-2-halo-1-oxo($C_1$ to $C_4$)alkane (VII-a1) are subjected to addition reaction and then to reducing elimination reaction, thereby producing the compound (I) {wherein $(A^1-X^1_n)$ is $CH=CX^{11}X^{12}$; s is 1; and p is 1}.

$C(X^{11}X^{12}X^{13})CHO$      (VII-a1)

wherein $X^{13}$ is a halogen atom; and $X^{11}$ and $X^{12}$ are a hydrogen atom or have the same meanings as those defined in $X^1$.

As the $X^{13}$, chlorine atom and bromine atom are preferred.

As the compound (VII-a1), there may be exemplified chloral (trichloroacetaldehyde), 2,2,3-trichloro-1-oxobutane and tribromoacetaldehyde.

The production process according to the fifth aspect of the present invention comprises a step of forming a carbon-oxygen bond between the carbon atom to which the leaving group (L) of the compound (VII-b) is bonded and the oxygen atom of hydroxyl group directly bonded to the nitrogen atom of amide moiety of the compound (VIII), or forming a carbon-nitrogen bond between the carbon atom to which the leaving group (L) of the compound (VII-b) is bonded and the nitrogen atom of amino group or (substituted or unsubstituted) alkylamino group directly bonded to the nitrogen atom of amide moiety of the compound (VIII) (hereinafter referred to merely as "step D").

That is, N-substituted-4-substituted-6-(substituted or unsubstituted) phenoxy-2-pyridine carboxamide or thiocarboxamide represented by the general formula (I-d) can be produced by reacting N-substituted-4-substituted-6-(substituted or unsubstituted) phenoxy-2-pyridine carboxamide or thiocarboxamide represented by the general formula (VIII) with a compound (VII-b), usually in an aprotic organic solvent.

This reaction is expressed by the following reaction formula 4.

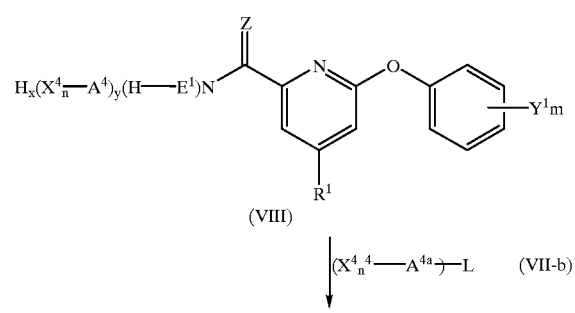

-continued

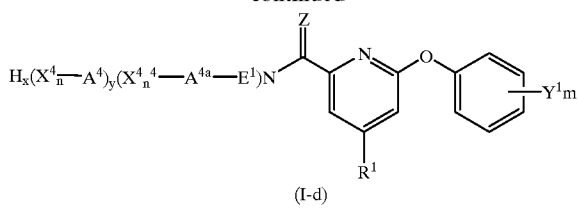

(I-d)

wherein $R^1$ is a $C_1$ to $C_4$ alkoxy group, a $C_1$ to $C_4$ alkylthio group, a $C_1$ to $C_4$ alkylamino group, a di($C_1$ to $C_4$ alkyl) amino group or a ($C_1$ to $C_4$ alkyl)($C_7$ to $C_8$ aralkyl)amino group;

$A^4$ may be substituted with $X^4$, and is a $C_1$ to $C_{10}$ alkyl group, a $C_3$ to $C_6$ alkenyl group, a $C_3$ to $C_6$ alkynyl group, a $C_3$ to $C_6$ cycloalkyl group, a phenyl group or an arylalkyl group (whose alkyl moiety has 1 to 3 carbon atoms), {wherein the chain-like hydrocarbon moiety of $A^4$ is constituted by a longest carbon chain as a main chain exclusive of a $C_1$ to $C_4$ alkyl group bonded as side chain to the main chain, and the $C_1$ to $C_4$ alkyl groups as side chains constitute $X^4$};

$A^{4a}$ may be substituted with $X^4$, and is a $C_1$ to $C_{10}$ alkyl group, a $C_3$ to $C_6$ alkenyl group, a $C_3$ to $C_6$ alkynyl group, a $C_3$ to $C_6$ cycloalkyl group or an arylalkyl group (whose alkyl moiety has 1 to 3 carbon atoms), wherein the chain-like hydrocarbon moiety of $A^{4a}$ is constituted by a longest carbon chain as a main chain exclusive of side chains, and the side chains constitute $X^4$;

$E^1H$ is a hydroxyl group, an amino group or a $C_1$ to $C_{10}$ alkylamino group which may be substituted with $X^4$, {wherein the chain-like hydrocarbon moiety of $E^1$ is constituted by a longest carbon chain as a main chain exclusive of a $C_1$ to $C_4$ alkyl group bonded as side chain to the main chain, and the $C_1$ to $C_4$ alkyl groups as side chains constitute $X^4$};

$X^4$ is a halogen atom, a $C_1$ to $C_4$ alkoxy group, a $C_1$ to $C_4$ alkylthio group, a $C_1$ to $C_4$ alkyl group (which is not bonded to a terminal position of $A^4$ and $A^{4a}$ when the $A^4$ and $A^{4a}$ are a $C_1$ to $C_{10}$ alkyl group), a $C_3$ to $C_6$ cycloalkyl group, a $C_1$ to $C_4$ alkylamino group, a di($C_1$ to $C_4$ alkyl)amino group, a $C_1$ to $C_4$ alkylsulfonyl group, a $C_1$ to $C_4$ alkylsulfinyl group, a hydroxyl group, amino group, a cyano group or a thiol group wherein the alkyl moiety of $X^4$ may be substituted with halogen atom(s);

n and $n^4$ are 0 or an integer selected from numbers of hydrogen atoms of $A^4$ and $A^{4a}$ which can be substituted with $X^4$, and when n and $n^4$ are an integer of not less than 2, $X^4$s may be the same or different;

x is 0 or 1 and y is 0 or 1 with the proviso that the sum of x and y (x+y) is 1;

$Y^1$ is a $C_1$ to $C_4$ haloalkyl group, a $C_1$ to $C_4$ alkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom;

m is an integer of 0 to 5, and when m is not less than 2, $Y^1$s may be the same or different;

Z is an oxygen atom or a sulfur atom; and

L is a leaving group.

This nucleophilic substitution reaction is usually carried out under basic conditions. The amount of the compound (VII-b) used is usually 0.8 to 4 moles, preferably 1.0 to 2 moles based on one mole of the compound (VIII).

The amount of the base used is described below. In the case where $E^1$ of the compound (VIII) wherein x is 1, is a hydroxyl group or a (substituted or unsubstituted) alkylamino group, since the compound (I-d) as a reaction product has a substitutable hydrogen atom on the nitrogen atom of carboxamide moiety thereof, it is disadvantageous to use the base in such a amount largely exceeding that of the compound (VIII). Therefore, it is preferred that in order to obtain the compound (I-d) wherein x is 1, with a high yield, the base is used in a slightly excessive molar amount relative to that of the compound (VIII). The amount of the base used is usually 0.8 to 1.5 moles, preferably 1.0 to 1.2 moles based on one mole of the compound (VIII).

In the case where $E^1$ of the compound (VIII) is an amino group, two substitutable hydrogen atoms are present on the $E^1$. Therefore, when it is aimed to convert the amino group into the (substituted or unsubstituted) alkylamino group, it is disadvantageous to use the base in such a molar amount largely exceeding that of the compound (VIII). Accordingly, it is preferred that the base is used in a slightly excessive molar amount relative to that of the compound (VIII). The amount of the base used is usually 0.8 to 1.5 moles, preferably 1.0 to 1.2 moles based on one mole of the compound (VIII).

In the case where $E^1H$ of the compound (VIII) wherein x is 0, is a hydroxyl group or (substituted or unsubstituted) alkylamino group, no substitutable hydrogen atom is present on the nitrogen atom of carboxamide of the produced compound (I-d). Therefore, the base can be used in an excessive molar amount exceeding that of the compound (VIII), and the use of excessive amount of the base is rather preferred. In this case, the amount of the base used is usually 0.8 to 2.0 moles, preferably 1.0 to 1.5 moles based on one mole of the compound (VIII). The reaction temperature is usually 0 to 200° C., preferably 10 to 150° C. The reaction time is several minutes to several days.

In the step D, as the compound (VII-b), there may be used substituted halides (compounds wherein L is a halogen atom; examples of the halogen atoms may include chlorine atom, bromine atom, iodine atom or the like), substituted dialkyl sulfate compounds (compounds wherein L is a substituted sulfate), substituted sulfonate compounds (compounds wherein L is a substituted sulfonate) or the like.

As the compounds (VII-b), there can also be used commercially available products or compounds similar to those exemplified with respect to the compounds (VII-a), which can be produced by known techniques.

As the compounds (VIII) usable as a raw material in the step D, there can used the following compounds:

Compounds (I-b) as a reaction product in the step B;

Compounds (I-f) as a reaction product in the step F; and

Compounds derived from the compounds (I-b) and (I-f), for example, compound (I-g) as a product obtained by hydrogenolysis thereof, compound (I-i) as a product obtained by oxidation of sulfide bond, or the like.

The production process according to the sixth aspect of the present invention comprises a step of forming a carbon-oxygen bond between the carbon atom to which the leaving group (L) of the compound (VII-c) is bonded and the oxygen atom of hydroxyl group as a substituent bonded to the $A^5$ of the compound (IX); forming a carbon-sulfur bond between the above-mentioned carbon atom and the thiol group; or forming a carbon-nitrogen bond between the above-mentioned carbon atom and the nitrogen atom of the amino group or (substituted or unsubstituted) alkylamino group (hereinafter referred to merely as "step E").

That is, N-substituted-4-substituted-6-(substituted or unsubstituted) phenoxy-2-pyridine carboxamide or thiocarboxamide represented by the general formula (I-e) can be produced by reacting N-substituted-4-substituted-6-(substituted or unsubstituted) phenoxy-2-pyridine carboxamide or thiocarboxamide represented by the general formula (IX) with a compound represented by the general formula (VII-c), usually in an aprotic organic solvent, This reaction is expressed by the following reaction formula 5.

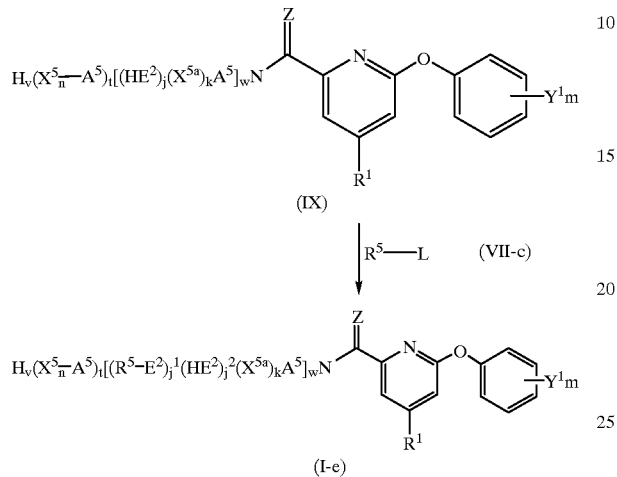

wherein $R^1$ is a $C_1$ to $C_4$ alkoxy group, a $C_1$ to $C_4$ alkylthio group, a $C_1$ to $C_4$ alkylamino group, a di($C_1$ to $C_4$ alkyl) amino group or a ($C_1$ to $C_4$ alkyl)($C_7$ to $C_8$ aralkyl)amino group;

$A^5$ may be substituted with $X^5$, and is a $C_1$ to $C_{10}$ alkyl group, a $C_2$ to $C_6$ alkenyl group, a $C_3$ to $C_6$ alkynyl group, a $C_3$ to $C_6$ cycloalkyl group, a $C_1$ to $C_{10}$ alkoxy group, a $C_3$ to $C_6$ alkenyloxy group, a $C_3$ to $C_6$ alkynyloxy group, a $C_1$ to $C_{10}$ alkylamino group, a di($C_1$ to $C_6$ alkyl)amino group, a phenyl group, a phenylamino group, an arylalkyl group (whose alkyl moiety has 1 to 3 carbon atoms), an arylalkyloxy group (whose alkyl moiety has 1 to 3 carbon atoms) or an arylalkylamino group (whose alkyl moiety has 1 to 3 carbon atoms), {wherein the chain-like hydrocarbon moiety of $A^5$ is constituted by a longest carbon chain as a main chain exclusive of a $C_1$ to $C_4$ alkyl group bonded as side chain to the main chain, and the $C_1$ to $C_4$ alkyl groups as side chains constitute $X^5$};

$X^5$ is a halogen atom, a $C_1$ to $C_4$ alkoxy group, a $C_1$ to $C_4$ alkylthio group, a $C_1$ to $C_4$ alkyl group (which is not bonded to a terminal position of $A^5$ when the $A^5$ is a $C_1$ to $C_{10}$ alkyl group, a $C_1$ to $C_{10}$ alkoxy group, a $C_1$ to $C_{10}$ alkylamino group or a di($C_1$ to $C_6$ alkyl)amino group), a $C_3$ to $C_6$ cycloalkyl group, a $C_1$ to $C_4$ alkylamino group, a di($C_1$ to $C_4$ alkyl)amino group, a $C_1$ to $C_4$ alkylsulfonyl group, a $C_1$ to $C_4$ alkylsulfinyl group, a hydroxyl group, an amino group, a cyano group or a thiol group, wherein the alkyl moiety of $X^5$ may be substituted with halogen atom(s);

$X^{5a}$ is a halogen atom, a $C_1$ to $C_4$ alkoxy group, a $C_1$ to $C_4$ alkylthio group, a $C_1$ to $C_4$ alkyl group (which is not bonded to terminal positions of $A^5$ when said $A^5$ is a $C_1$ to $C_{10}$ alkyl group, a $C_1$ to $C_{10}$ alkoxy group, a $C_1$ to $C_{10}$ alkylamino group or a di($C_1$ to $C_6$ alkyl)amino group), a $C_3$ to $C_6$ cycloalkyl group, a di($C_1$ to $C_4$ alkyl)amino group, a $C_1$ to $C_4$ alkylsulfonyl group, a $C_1$ to $C_4$ alkylsulfinyl group or a cyano group, wherein the alkyl moiety of $X^{5a}$ may be substituted with halogen atom(s);

n is 0 or an integer selected from numbers of hydrogen atoms of $A^5$ which can be substituted with $X^5$, and when n is an integer of not less than 2, $X^5$s may be the same or different;

t is 0 or 1, v is 0 or 1 and w is 1 or 2 with the proviso that the sum of t and v (t+v) is 0 or 1 and the sum of t, v and w (t+v+w) is 2; when w is 2, and t and w are 1, $A^5$s may be the same or different; and when w is 2 and $A^5$s are alkyl chains, the $A^5$s may be directly bonded together or may be bonded to each other through an oxygen atom of the hydroxyl group, or a nitrogen atom of the amino group or the $C_1$ to $C_4$ alkylamino group which groups are bonded to one of the $A^5$s, to form a ring;

$E^2H$ is a hydroxyl group, an amino group, thiol group or a $C_1$ to $C_4$ alkylamino group which may be substituted with halogen atom(s);

$R^5$ is $C_1$ to $C_4$ alkyl group which may be substituted with halogen atom;

j is an integer of not less than 1 and k is an integer of not less than 0, with the proviso that the sum of j and k (j+k) is 1 or an integer selected from numbers of hydrogen atoms of $A^5$ which can be substituted with $X^5$; when j is not less than 2, $E^2$Hs may be the same or different; and when k is not less than 2, X5as may be the same or different;

$j^1$ is an integer of not less than 1 and $j^2$ is an integer of not less than 0 with the proviso that the sum of $j^1+j^2$ is j;

$Y^1$ is a $C_1$ to $C_4$ haloalkyl group, a $C_1$ to $C_4$ alkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom;

m is an integer of 0 to 5, and when m is not less than 2, $Y^1$s may be the same or different;

Z is an oxygen atom or a sulfur atom; and

L is a leaving group.

The compound (I-e) can be produced by the reaction between the compound (VII-c) and the compound (IX), specifically by nucleophilically substituting the leaving group (L) of the compound (VII-c) with the oxygen, sulfur atom or nitrogen atom of the compound (IX).

The mount of the compound (VII-c) used is usually 0.8 to 4 moles, preferably 1.0 to 2 moles based on one mole of the compound (IX).

The above reaction is carried out usually under basic conditions. The amount of the base used is described below. In the case where $E^2$ of the compound (IX) wherein v is 1 and j is 1, is a hydroxyl group, a thiol group or a (substituted or unsubstituted) alkylamino group, the compound (I-e) as a reaction product has a substitutable hydrogen atom on the nitrogen atom carboxamide thereof. Therefore, when it is aimed to obtain the compound (I-e) wherein x is 1, it is disadvantageous to use the base in such a molar amount largely exceeding that of the compound (IX). Accordingly, it is preferred that the base be used in a slightly excessive molar amount relative to that of the compound (IX). The amount of the base used is usually 0.8 to 1.5 moles, preferably 1.0 to 1.2 moles based on one mole of the compound (IX).

In the compound (IX), in the case where $E^2$ thereof is an amino group, two substitutable hydrogen atoms are present on the $E^2$. Therefore, when it is aimed to convert the amino group into the (substituted or unsubstituted) alkylamino group, it is disadvantageous to use the base in such a molar amount exceeding that of the compound (IX). Accordingly, it is preferred that the base be used in a slightly excessive molar amount relative to that of the compound (IX). The amount of the base used is usually 0.8 to 1.5 moles, preferably 1.0 to 1.2 moles based on one mole of the compound (IX).

In the compound (IX) wherein v is 0 and j is 1, in the case where $E^2$ thereof is a hydroxyl group, a thiol group or a (substituted or unsubstituted) alkylamino group, no substitutable hydrogen atoms are present on the compound (I-e) as a reaction product. Therefore, it is possible to use the base in such a molar amount exceeding that of the compound (IX), and it is rather preferred to use an excessive amount of the base. In this case, the amount of the base used is usually 0.8 to 2.0 moles, preferably 1.0 to 1.5 moles based on one mole of the compound (IX). The reaction temperature is usually 0 to 200° C., preferably 10 to 150° C.

In the compound (IX), in the case where a plurality of substitutable hydrogen atoms are present on the $E^2$ thereof and all the hydrogen atoms are to be substituted with the compound (VII-c), it is preferred that the compound (VII-c) be used in an amount of 1 to 3 equivalents, and the base be used in an equivalent amount or in an excessive amount based on one equivalent of the substituted hydrogen atom of the compound (IX). the reaction time is several minutes to several days.

In the step E, as the compound (VII-c), there may be used substituted halides (compounds wherein L is a halogen atom; examples of the halogen atoms may include chlorine atom, bromine atom, iodine atom or the like), substituted dialkyl sulfate compounds (compounds wherein L is a substituted sulfate), substituted sulfonate compounds (compounds wherein L is a substituted sulfonate) or the like.

As the compounds (VII-c), there can also be used commercially available products or compounds similar to those exemplified with respect to the compounds (VII-a), which can be produced by known techniques.

As the compounds (IX) usable as a raw material in the step E, there can used the following compounds:

Compounds (I-b) as a reaction product in the step B;

Compounds (I-c) as a reaction product in the step C;

Compounds (I-d) as a reaction product in the step D;

Compounds (I-e) as a reaction product in the step E;

Compounds (I-f) as a reaction product in the step F; and

Compounds derived from the compounds (I-a) to (I-f), for example, compound (I-g) as a product obtained by hydrogenolysis thereof, compound (I-i) as a product obtained by oxidation of sulfide bond, or the like.

The production process according to the seventh aspect of the present invention comprises a step of forming a carbon-oxygen bond between the carbon atom to which the halogen atom represented by $T^1$ in the compound (X) is bonded and the oxygen atom of phenol of the compound (XI) (hereinafter referred to merely as "step F").

That is, N-(substituted or unsubstituted)-4-substituted-6-(substituted or unsubstituted) phenoxy-2-pyridine carboxamide or thiocarboxamide represented by the general formula (I-f) can be produced by reacting N-(substituted or unsubstituted)-4-substituted-6-halogeno-2-pyridine carboxamide or thiocarboxamide represented by the general formula (X) with (substituted or unsubstituted) phenol represented by the general formula (XI), usually in an aprotic organic solvent.

This reaction is expressed by the following reaction formula 6.

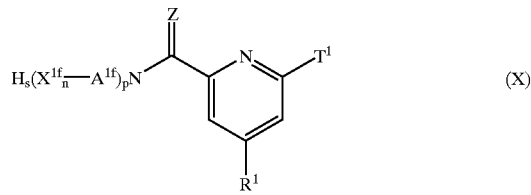

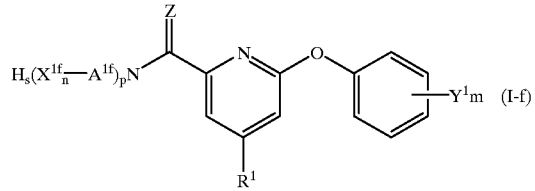

wherein $R^1$ is a $C_1$ to $C_4$ alkoxy group, a $C_1$ to $C_4$ alkylthio group, a $C_1$ to $C_4$ alkylamino group, a di($C_1$ to $C_4$ alkyl) amino group or a ($C_1$ to $C_4$ alkyl)($C_7$ to $C_8$ aralkyl)amino group;

$A^{1f}$ may be substituted with $X^{1f}$, and is a $C_1$ to $C_{10}$ alkyl group, a $C_2$ to $C_6$ alkenyl group, a $C_3$ to $C_6$ alkynyl group, a $C_3$ to $C_6$ cycloalkyl group, a $C_1$ to $C_{10}$ alkoxy group, a $C_3$ to $C_6$ alkenyloxy group, a $C_3$ to $C_6$ alkynyloxy group, a $C_1$ to $C_{10}$ alkylamino group, a di($C_1$ to $C_6$ alkyl)amino group, a phenyl group, a phenylamino group, an arylalkyl group (whose alkyl moiety has 1 to 3 carbon atoms), an arylalkyloxy group (whose alkyl moiety has 1 to 3 carbon atoms), an arylalkylamino group (whose alkyl moiety has 1 to 3 carbon atoms) or a hydroxyl group, (wherein the chain-like hydrocarbon moiety of $A^{1f}$ is constituted by a longest carbon chain as a main chain exclusive of a $C_1$ to $C_4$ alkyl group bonded as side chain to the main chain, and the $C_1$ to $C_4$ alkyl groups as side chains constitute $X^{1f}$);

$X^{1f}$ is a halogen atom, a $C_1$ to $C_4$ alkoxy group, a $C_1$ to $C_4$ alkylthio group, a $C_1$ to $C_4$ alkyl group (which is not bonded to a terminal position of $A^{1f}$ when the $A^{1f}$ is a $C_1$ to $C_{10}$ alkyl group, a $C_1$ to $C_{10}$ alkoxy group, a $C_1$ to $C_{10}$ alkylamino group or a di($C_1$ to $C_6$ alkyl)amino group), a $C_3$ to $C_6$ cycloalkyl group, a $C_1$ to $C_4$ alkylcarbonyl group, a $C_1$ to $C_4$ alkylamino group, a di($C_1$ to $C_4$ alkyl)amino group, a $C_1$ to $C_4$ alkylsulfonyl group, a $C_1$ to $C_4$ alkylsulfinyl group, a hydroxyl group, an amino group, a cyano group or a thiol group, wherein the alkyl moiety of $X^{1f}$ may be substituted with halogen atom(s);

n is 0 or an integer selected from numbers of hydrogen atoms of $A^{1f}$ which can be substituted with $X^{1f}$, and when n is an integer of not less than 2, $X^{1f}$s may be the same or different;

p and s are an integer of 0 to 2 with the proviso that the sum of p and s (p+s) is 2; when p is 2, $A^{1f}$s may be the same or different; and when p is 2 and $A^{1f}$s are alkyl chains, the $A^{1f}$s may be directly bonded together or may be bonded to each other through an oxygen atom of the hydroxyl group, or a nitrogen atom of the amino group or the $C_1$ to $C_4$ alkylamino group which groups are bonded to one of the $A^{1f}$s, to form a ring;

$Y^1$ is a $C_1$ to $C_4$ haloalkyl group, a $C_1$ to $C_4$ alkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom;

m is an integer of 0 to 5, and when m is not less than 2, $Y^1$s may be the same or different;

Z is an oxygen atom or a sulfur atom; and $T^1$ is a halogen atom.

The compound (I-f) can be produced by the reaction between the above-mentioned compounds (X) and (XI), specifically by nucleophilically substituting the halogen atom ($T^1$) of the compound (X) with the oxygen atom of phenol of the compound (XI). In the phenoxylation reaction of the compound (X), the compounds (X) and (XI) are reacted with each other, usually under basic conditions.

In the above-mentioned reaction, it is possible to use the base in such a molar mount exceeding that of the compound (X). The amount of the compound (XI) charged is allowed to exceed 2 moles based on one mole of the compound (X) in the presence of such an excessive amount of the base. The amount of the base used is usually 0.8 to 10 moles, preferably 1 to 5 moles based on one mole of the compound (X).

The amount of the compound (XI) charged is usually 0.8 to 15 moles, preferably 1.2 to 10 moles based on one mole of the compound (X).

Also, it is preferred to add a catalyst such as copper halide. The amount of the catalyst added is usually 0.01 to 10 moles, preferably 0.1 to 5 moles based on one mole of the compound (X).

The reaction temperature is usually 0 to 200° C., preferably 60 to 180° C. the reaction time is several hours to several days.

The compound (X) used as a raw material in the step F may be produced in the following manner.

First, in the first method, the compound (X-a) is produced by obtaining 2-halogeno-4-substituted-6-(metal-substituted) pyridine represented by the general formula (XVII) by metalation of the compound (XIII); thereafter subjecting the metalated pyridine to addition-reaction to a carbon-nitrogen double bond of the compound (III); and then substituting a proton for the metal of the obtained addition product.

The substitution of proton for the metal of the addition product, can be carried out by treating the obtained addition reaction solution with an acid aqueous solution.

This reaction is expressed by the following reaction formula 13.

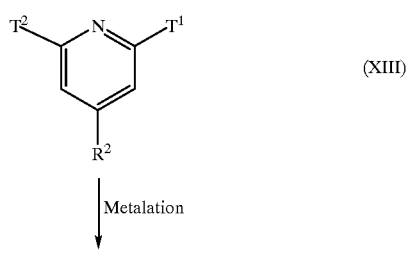

(XIII)

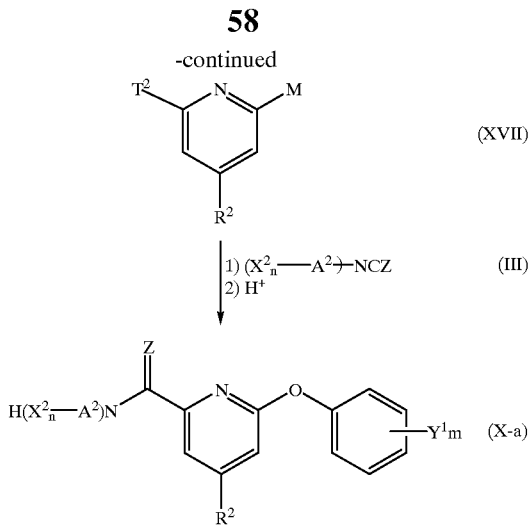

wherein $R^2$, $T^1$, $T^2$, M, $A^2$, $X^2$, Z and n have the same meanings as defined above.

In the metalation for the production of the compound (XVII), since two substitutable halogen atoms are present in the compound (XIII), the amount of the metalating reagent used for the metalation of the compound (XIII) is usually 0.5 to 1.7 moles, preferably 0.8 to 1.4 moles based on one mole of the compound (XIII). In general, after the metalation, the metalated product is subjected to the next addition reaction without isolation of the compound (XVII). The amount of the compound (III) used is usually 0.6 to 3 moles, preferably 0.8 to 2.5 moles based on one mole of the compound (XVII).

As the production conditions, there may be adopted the conditions used in the step A for the metalation, the addition of the compound (II) to isocyanate and then the production of the compound (I-a) by proton-substitution.

N-(substituted or unsubstituted)-4-substituted-6-halogeno-2-pyridine carboxamide or thiocarboxamide used as a raw material in the step F, may be produced in the following manner.

The above-mentioned compound (X-b) can be obtained by treating 4-substituted-6-halogeno-2-picolinic acid or dithiopicolinic acid compound (XVIII-a) with a halogenating reagent such as thionyl chloride to prepare 4-substituted-6-halogeno-2-picolinic halide or thiopicolinic halide and then subjecting the halide to amidation using the compound (V-a). This reaction is expressed by the following reaction formula 14.

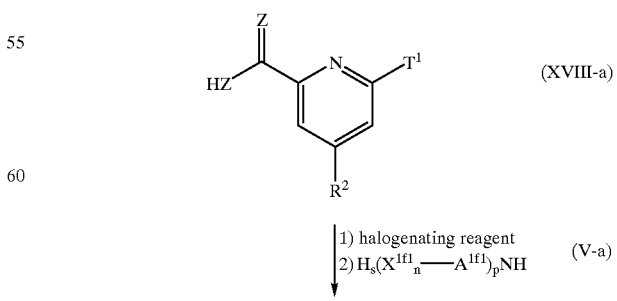

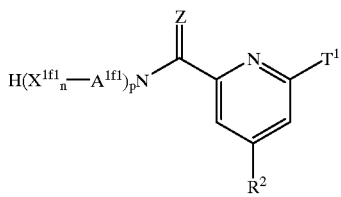

(X-b)

wherein $R^2$, Z, $T^1$, p, s and n have the same meanings as defined above; and $A^{1f1}$ and $X^{1f1}$ have the same meanings as those for $A^1$ and $X^1$.

As the production conditions, there may be adopted the conditions used in the step B for producing the compound (I-b) by the reaction between the compound (IV) wherein W is a halogen atom, and the compound (V).

4-substituted-6-halogeno-2-picolinic acid or dithiopicolinic acid compound (XVIII-a) used in the above step, may be produced by the following methods.

In the first method, the compound (XVIII-a) may be obtained by adding the above-mentioned compound (XVII) to carbon dioxide or carbon disulfide and then subjecting the obtained product to proton-substitution. This reaction is expressed by the following reaction formula 15.

Reaction Formula 15:

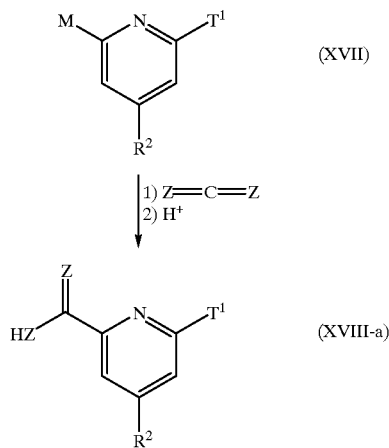

wherein $R^2$, M, Z and $T^1$ have the same meanings as defined above.

As the production conditions, there may be adopted the conditions used in the step A for the addition of the compound (II) to isocyanate and then the production of the compound (I-a) by proton-substitution.

In the second method, the compound (XVIII-b) may be obtained by hydrolysis of the above-mentioned 4-substituted-6-halogeno-2-halogenopyridine {compound (XVI)}. This reaction is expressed by the following reaction formula 16:

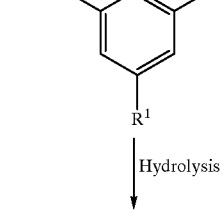

(XVI)

Hydrolysis

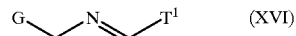

(XVIII-b)

wherein $R^1$, $T^1$ and G have the same meanings as defined above.

As the production conditions, there may be adopted the conditions used in the above reaction formula 10 for the hydrolysis of the compound (XV).

In addition, as other methods, there may also be used, for example, a method of producing 4-methoxy-6-chloropicolinic acid {compound (XVIII-b) wherein $R^1$ is $OCH_3$ and $T^1$ is Cl} by oxidizing the hydroxymethyl group of 4-methoxy-6-chloro-2-pyridine methanol.

Further, for example, 4-unsubstituted-6-halogeno-2-pyridine carboxamide or thiocarboxamide {compound (X-c)} used as a raw material in the step F, may be produced in the following manner.

The compound (X-c) may be obtained by subjecting the above-prepared compound (XVIII-b) and the compound (V-b) to condensation reaction. This reaction is expressed by the following reaction formula 17:

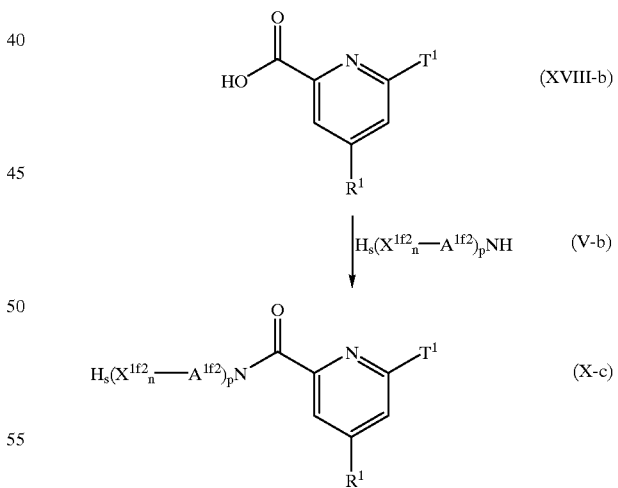

wherein $R^1$, $T^1$, p, s and n have the same meanings as defined above; and $A^{1f2}$ and $X^{1f2}$ have the same meanings as those for $A^1$ and $X^1$.

As the production conditions, there may be adopted the conditions used in the step B for producing the compound (I-b) by the reaction between the compound (IV) wherein W is OH, and the compound (V).

Further, the compound (X-d) may be obtained by the reaction between the compound (XVI-a) {compound (XVI)

wherein G is lower alkylcarbonyl, which is used as a raw material in the reaction formula 11} and the compound (V-c). This reaction is expressed by the following reaction formula 18.

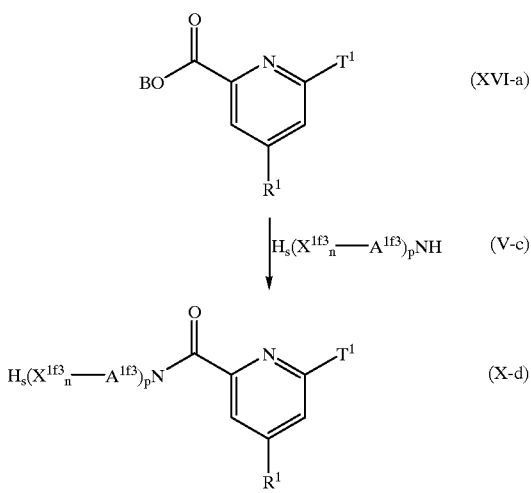

wherein $R^1$, Z, $T^1$, B, p, s and n have the same meanings as defined above; and $A^{1f3}$ and $X^{1f3}$ have the same meanings as those for $A^1$ and $X^1$.

As the production conditions, there may be adopted the conditions used in the step B for producing the compound (I-b) by the reaction between the compound (IV) wherein W is lower alkoxy, and the compound (V).

Further, the compound (X-e) {same as compound (X) wherein Z is S} may be obtained by sulfidization of Z of the compound (X-f) {same as the compound (X) wherein Z is O}. This reaction is expressed by the following reaction formula 19:

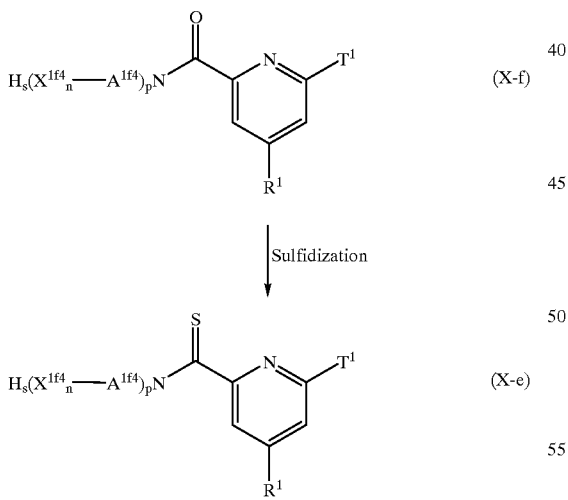

wherein $R^1$, $T^1$, p, s and n have the same meanings as defined above; and $A^{1f4}$ and $X^{1f4}$ have the same meanings as those for $A^1$ and $X^1$.

The sulfidization reaction may be carried out in an inert aromatic organic solvent (such as benzene, toluene or pyridine) using phosphorus pentaoxide or a Lawesson reagent. The reaction temperature is usually 0 to 200° C., preferably 60 to 140° C. The reaction time is several minutes to several days.

Further, such compounds (X) obtained by modifying the amide moiety of each of the above-mentioned compounds (X-a), (X-b), (X-c), (X-d) and (X-e) using the conditions of modification reactions in the steps C, D, E, etc., may also be used as a raw material in the step F.

The method of producing the compound (I) wherein $R^1$ is a $C_1$ to $C_4$ alkylamino group by hydrogenolysis, will be explained below.

N-(substituted or unsubstituted)-4-($C_1$ to $C_4$ alkylamino)-6-(substituted or unsubstituted) phenoxy-2-pyridine carboxamide or thiocarboxamide represented by the general formula (I-g) may be obtained by hydrogenolysis of a phenylmethyl group of N-(substituted or unsubstituted)-4-{$C_1$ to $C_4$ alkyl(phenylmethyl)amino}-6-(substituted or unsubstituted) phenoxy-2-pyridine carboxamide or thiocarboxamide represented by the general formula (I-h) usually in a solvent. This reaction is expressed by the following reaction formula 20.

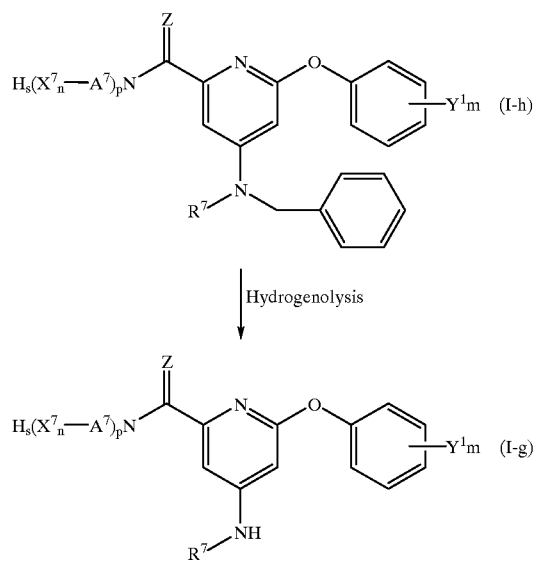

wherein $Y^1$, Z, p, s and m are the same as defined above; $X^7$ is the same as defined in $X^1$; $R^7$ is a $C_1$ to $C_4$ alkyl group; $A^7$ may be substituted with $X^7$, and is a $C_1$ to $C_{10}$ alkyl group, a $C_3$ to $C_6$ cycloalkyl group, a $C_1$ to $C_{10}$ alkoxy group, a $C_1$ to $C_{10}$ alkylamino group, a di($C_1$ to $C_6$ alkyl)amino group, a phenyl group, a phenylamino group, an arylalkyl group (whose alkyl moiety has 1 to 3 carbon atoms), an arylalkyloxy group (whose alkyl moiety has 1 to 3 carbon atoms), an arylalkylamino group (whose alkyl moiety has 1 to 3 carbon atoms), an amino group or a hydroxyl group, {wherein the chain-like hydrocarbon moiety of $A^7$ is constituted by a longest carbon chain as a main chain exclusive of a $C_1$ to $C_4$ alkyl group bonded as side chain to the main chain, and the $C_1$ to $C_4$ alkyl groups as side chains constitute $X^7$};

$X^7$ is a halogen atom, a $C_1$ to $C_4$ alkoxy group, a $C_1$ to $C_4$ alkylthio group, a $C_1$ to $C_4$ alkyl group {which is not bonded to a terminal position of $A^7$ when the $A^7$ is a $C_1$ to $C_{10}$ alkyl group, a $C_1$ to $C^{10}$ alkoxy group, a $C_1$ to $C^{10}$ alkylamino group or a di($C_1$ to $C_6$ alkyl)amino group}, a $C_3$ to $C_6$ cycloalkyl group, a $C_1$ to $C_4$ alkylcarbonyl group, a $C_1$ to $C_4$ alkylamino group, a di($C_1$ to $C_4$ alkyl)amino group, a $C_1$ to $C_4$ alkylsulfonyl group, a $C_1$ to $C_4$ alkylsulfinyl group, a hydroxyl group, an amino group, a cyano group or a thiol group, wherein the alkyl moiety of $X^7$ may be further substituted with halogen atom(s);

n is 0 or an integer selected from number of hydrogen atoms of $A^7$ which can be substituted with $X^7$, and when n is an integer of not less than 2, $X^1$s may be the same or different;

when p is 2, $A^1$s may be the same or different;

when p is 2 and both of $A^7$s are alkyl chains, the $A^7$s may be directly bonded together or may be bonded to each other through an oxygen atom of the hydroxyl group, or a nitrogen atom of the amino group or the $C_1$ to $C_4$ alkylamino group which groups are bonded to one of the $A^1$s, to form a ring.

As hydrogenating catalysts used in the hydrogenolysis, there may be usually exemplified platinum, palladium, nickel, etc., whose surface area is increased to enhance the catalytic activity, or those obtained by supporting these metals on activated carbon, carbon, barium carbonate, alumina or the like. Among these catalysts, there may be preferably used palladium carbon, Raney nickel or the like. In addition, as the reaction accelerators, among the above-mentioned acids, there may be preferably used hydrochloric acid, perchloric acid, acetic acid or the like. The reaction may be conducted in a temperature range of from room temperature to 40° C. for 30 minutes to several days.

Next, there will be described the method of producing the compound (I) {wherein $X^1$ is a ($C_1$ to $C_4$ alkyl)sulfonyl group and/or a ($C_1$ to $C_4$ alkyl)sulfinyl group, whose alkyl group may be substituted with halogen atom(s)} by the oxidation of sulfur atom of the compound (I) {wherein $X^1$ is a ($C_1$ to $C_4$ alkyl)thio group whose alkyl group may be substituted with halogen atom(s)}.

The compound (I-i) may be obtained by oxidizing a sulfur atom of (halogen-substitutable $C_1$ to $C_4$ alkyl)thio group bonded to $A^8$ of the compound (I-j). This reaction is expressed by the following reaction formula 21.

a $C_1$ to $C_{10}$ alkoxy group, a $C_3$ to $C_6$ alkenyloxy group, a $C_3$ to $C_6$ alkynyloxy group, a $C_1$ to $C_{10}$ alkylamino group, a di($C_1$ to $C_6$ alkyl)amino group, a phenyl group, a phenylamino group, an arylalkyl group (whose alkyl moiety has 1 to 3 carbon atoms), an arylalkyloxy group (whose alkyl moiety has 1 to 3 carbon atoms), an arylalkylamino group (whose alkyl moiety has 1 to 3 carbon atoms), an amino group or a hydroxyl group {wherein the chain-like hydrocarbon moiety of $A^8$ is constituted by a longest carbon chain as a main chain exclusive of a $C_1$ to $C_4$ alkyl group bonded as side chain to the main chain, and the $C_1$ to $C_4$ alkyl groups as side chains constitute $X^8$ or $X^{8a}$};

$X^8$ is a halogen atom, a $C_1$ to $C_4$ alkoxy group, a $C_1$ to $C_4$ alkylthio group, a $C_1$ to $C_4$ alkyl group (which alkyl group is not bonded to a terminal position of $A^8$ when the $A^8$ is a $C_1$ to $C_{10}$ alkyl group, a $C_1$ to $C_{10}$ alkoxy group, a $C_1$ to $C_{10}$ alkylamino group or a di($C_1$ to $C_6$ alkyl)amino group), a $C_3$ to $C_6$ cycloalkyl group, a $C_1$ to $C_4$ alkylcarbonyl group, a $C_1$ to $C_4$ alkylamino group, a di($C_1$ to $C_4$ alkyl)amino group, a $C_1$ to $C_4$ alkylsulfonyl group, a $C_1$ to $C_4$ alkylsulfinyl group, a hydroxyl group, an amino group or a cyano group, wherein the alkyl moiety of $X^8$ may be further substituted with halogen atom(s);

$X^{8a}$ is a halogen atom, a $C_1$ to $C_4$ alkoxy group, a $C_1$ to $C_4$ alkyl group (which alkyl group is not bonded to a terminal position of $A^8$ when the $A^8$ is a $C_1$ to $C_{10}$ alkyl group, a $C_1$ to $C_{10}$ alkoxy group, a $C_1$ to $C_{10}$ alkylamino group or a di($C_1$ to $C_6$ alkyl)amino group), a $C_3$ to $C_6$ cycloalkyl group, a $C_1$ to $C_4$ alkylcarbonyl group, a $C_1$ to $C_4$ alkylamino group, a di($C_1$ to $C_4$ alkyl)amino group, a $C_1$ to $C_4$ alkylsulfonyl group, a $C_1$ to $C_4$ alkylsulfinyl group, a hydroxyl group, an amino group or a cyano group, wherein the alkyl moiety of $X^{8a}$ may be further substituted with halogen atom(s);

$R^8$ is a $C_1$ to $C_4$ alkyy group which may be substituted with a halogen atom;

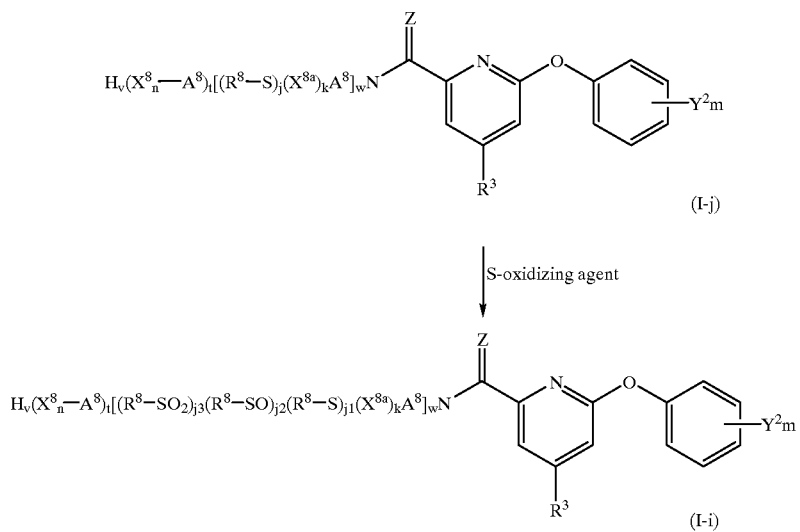

wherein $R^3$ is a $C_1$ to $C_4$ alkoxy group;

$A^8$ may be substituted with $X^8$, $X^{8a}$, $R^8S$, $R^8SO$ or $R^8SO_2$, and is a $C_1$ to $C_{10}$ alkyl group, a $C_2$ to $C_6$ alkenyl group, a $C_3$ to $C_6$ alkynyl group, a $C_3$ to $C_6$ cycloalkyl group, n is 0 or an integer selected from numbers of hydrogen atoms of $A^8$ which can be substituted with $X^8$;

when n is an integer of not less than 2, $X^8$s may be the same or different;

t is 0 or 1, v is 0 or 1 and w is 1 or 2 with the proviso that the sum of t and v (t+v) is 0 or 1 and the sum of t, v and w (t+v+w) is 2;

when w is 2 and t and w are 1, $A^8$s may be the same or different;

when w is 2 and both of $A^8$s are alkyl chains, the $A^8$s may be directly bonded together or may be bonded to each other through an oxygen atom of the hydroxyl group, or a nitrogen atom of the amino group or the $C_1$ to $C_4$ alkylamino group which groups are bonded to one of the $A^8$s, to form a ring;

j is an integer of not less than 1 and k is an integer of not less than 0 with the proviso that the sum of j and k (j+k) is 1 or an integer selected from numbers of hydrogen atoms of $A^8$ which can be substituted with $X^8$;

when j is not less than 2, $R^8$s may be the same or different;

when k is not less than 2, $X^{8a}$s may be the same or different;

$j^1$, $j^2$ and $j^3$ is an integer of not less than 0 with the proviso that the sum of $j^2$ and $j^3$ ($j^2+j^3$) is not less than 1 and the sum of $j^1$, $j^2$ and $j^3$ ($j^1+j^2+j^3$) is j;

$Y^2$ is a $C_1$ to $C_4$ haloalkyl group, a $C_1$ to $C_4$ alkyl group, a $C_1$ to $C_4$ alkoxy group, a $C_1$ to $C_4$ haloalkoxy group or a halogen atom;

m is an integer of 0 to 5, and when m is not less than 2, $Y^2$s may be the same or different; and Z is an oxygen atom or a sulfur atom.

As solvents used in the above oxidation reaction, there may be usually exemplified aromatic hydrocarbons such as benzene, toluene, xylene or methyl naphthalene; aliphatic hydrocarbons such as petroleum ethers, pentane, hexane, heptane, methyl cyclohexane or the like; halogenated hydrocarbons such as methylene chloride, chloroform, carbon tetrachloride, chlorobenzene or the like; amides such as dimethyl formamide, dimethyl acetamide, N-methyl-2-pyrrolidinone or the like; ethers such as diethyl ether, dimethoxy ethane, diisopropyl ether, tetrahydrofuran, diethylene glycol dimethyl ether (DIGLYM), dioxane or the like; aliphatic alcohols such as methanol, ethanol or the like; organic acids such as acetic acid or formic acid; or the like. As other solvents usable in the above oxidation reaction, there may be exemplified water, carbon disulfide, acetonitrile, ethyl acetate, acetic anhydride, dimethyl sulfoxide, hexamethylphophoric amide or the like. These solvents may be used in the form of a mixture of any two or more thereof.

As the oxidizing agents used in the above oxidation reaction, there may be usually exemplified organic peroxides such as m-chloro-perbenzoic acid, peracetic acid or the like; hydrogen peroxide, potassium permanganate, ruthenium oxide, osmium oxide, chromic acid, periodic acid or the like. The reaction temperature is usually 0 to 100° C., preferably 0 to 70° C. The reaction time is several minutes to several days.

Next, there will be described the method of producing the compound (I) {wherein $X^1$ is a ($C_1$ to $C_4$ alkyl)carbonyl group whose alkyl group may be substituted with a halogen atom} by carrying out an addition reaction between a ($C_1$ to $C_4$ alkyl)metal compound whose alkyl group may be substituted with a halogen atom and the cyano group of $X^1$ of the compound (I) wherein $X^1$ is a cyano group to form a carbon-carbon bond, and then subjecting the obtained product to hydrolysis.

The compound (I-k) may be obtained by carrying out an addition reaction between a ($C_1$ to $C_4$ alkyl)metal compound whose alkyl group may be substituted with a halogen atom and the cyano group of $A^9$ of the compound (I-m), and then subjecting the obtained product to hydrolysis.

This reaction is expressed by the following reaction formula 22.

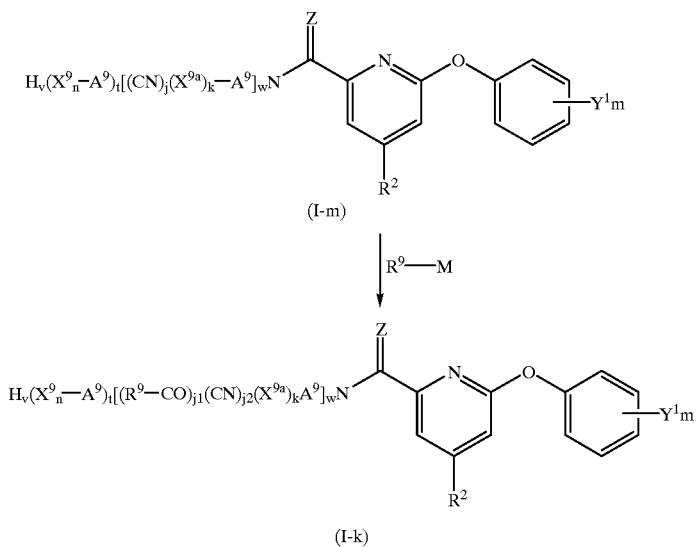

wherein $R^2$, $Y^1$, Z, M and m are the same as defined above;
$A^9$ may be substituted with $X^9$, $X^{9a}$, cyano or $R^9CO$, and is a $C_1$ to $C_{10}$ alkyl group, a $C_2$ to $C_6$ alkenyl group, a $C_3$ to $C_6$ alkynyl group, a $C_3$ to $C_6$ cycloalkyl group, a $C_1$ to $C_{10}$ alkoxy group, a $C_3$ to $C_6$ alkenyloxy group, a $C_3$ to $C_6$ alkynyloxy group, a di($C_1$ to $C_6$ alkyl)amino group, a phenyl group, an arylalkyl group (whose alkyl moiety has 1 to 3 carbon atoms) or an arylalkyloxy group (whose alkyl moiety has 1 to 3 carbon atoms) {wherein the chain-like hydrocarbon moiety of $A^9$ is constituted by a longest carbon chain as a main chain exclusive of a $C_1$ to $C_4$ alkyl group bonded as side chain to the main chain, and the $C_1$ to $C_4$ alkyl groups as side chains constitute $X^9$ or $X^{9a}$};

$X^9$ is a halogen atom, a $C_1$ to $C_4$ alkoxy group, a $C_1$ to $C_4$ alkylthio group, a $C_1$ to $C_4$ alkyl group {which alkyl group is not bonded to a terminal position of $A^9$ when the $A^9$ is a $C_1$ to $C_{10}$ alkyl group, a $C_1$ to $C_{10}$ alkoxy group or a di($C_1$ to $C_6$ alkyl)amino group}, a $C_3$ to $C_6$ cycloalkyl group, a di($C_1$ to $C_4$ alkyl)amino group, a $C_1$ to $C_4$ alkylsulfonyl group, a $C_1$ to $C_4$ alkylsulfinyl group or a cyano group, wherein the alkyl moiety of $X^9$ may be further substituted with halogen atom(s);

$X^{9a}$ is a halogen atom, a $C_1$ to $C_4$ alkoxy group, a $C_1$ to $C_4$ alkylthio group, a $C_1$ to $C_4$ alkyl group (which alkyl group is not bonded to a terminal position of $A^9$ when the $A^9$ is a $C_1$ to $C_{10}$ alkyl group, a $C_1$ to $C_{10}$ alkoxy group or a di($C_1$ to $C_6$ alkyl)amino group), a $C_3$ to $C_6$ cycloalkyl group, a di($C_1$ to $C_4$ alkyl)amino group, a $C_1$ to $C_4$ alkylsulfonyl group or a $C_1$ to $C_4$ alkylsulfinyl group, wherein the alkyl moiety of $X^{9a}$ may be further substituted with halogen atom(s);

$R^9$ is a $C_1$ to $C_4$ alkyl group which may be substituted with a halogen atom;

n is 0 or an integer selected from numbers of hydrogen atoms of $A^9$ which can be substituted with $X^9$;

when n is an integer of not less than 2, $X^9$s may be the same or different;

t is 0 or 1, v is 0 or 1 and w is 1 or 2 with the proviso that the sum of t and v (t+v) is 0 or 1 and the sum of t, v and w (t+v+w) is 2;

when w is 2 or t and w are 1, $A^9$s may be the same or different;

when w is 2 and both of $A^9$s are alkyl chains, the $A^9$s may be directly bonded together or may be bonded to each other through an oxygen atom of the hydroxyl group or a nitrogen atom of the amino group or the $C_1$ to $C_4$ alkylamino group, the hydroxyl, amino or alkyl amino group bonded to one of the $A^9$s, to form a ring;

j is an integer of not less than 1 and k is an integer of not less than 0 with the proviso that the sum of j and k (j+k) is 1 or an integer selected from numbers of hydrogen atoms of $A^9$ which can be substituted with $X^9$;

when j is not less than 2, $R^9$s may be the same or different;

when k is not less than 2, $X^{9a}$s may be the same or different; and $j^1$ is an integer of not less than 1 and $j^2$ is an integer of not less than 0 with the proviso that the sum of $j^1$ and $j^2$ ($j^1+j^2$) is j.

As solvents used in the above alkylcarbonylation reaction, there may be used solvents suited to the reaction of organic metal compounds. Examples of these solvents may include usually aliphatic hydrocarbons such as petroleum ethers, pentane, hexane, heptane, methyl cyclohexane or the like; ethers such as diethyl ether, dimethoxy ethane, diisopropyl ether, tetrahydrofuran, diethylene glycol dimethyl ether (DIGLYM), dioxane or the like; aromatic hydrocarbons such as benzene, toluene, xylene methyl naphthalene or the like.

As the alkyl metal reagents used in the above alkylcarbonylation reaction, there may be usually used organic alkali metal compounds such as butyl lithium, sec-butyl lithium, tert-butyl lithium, methyl lithium or the like; Grignard reagents such as methyl magnesium bromide, ethyl magnesium bromide or the like; or organic copper compounds produced by the above-mentioned compounds with a monovalent copper salt such as copper iodide (CuI). As the alkyl metal halide reagents, there may be used such reagents obtained by reacting alkyl halide with the above-mentioned alkyl metal reagent, alkali metal such as lithium, alkali earth metal such as magnesium, copper or the like. Examples of these reagents may include trichloromethyl lithium, 2,2,2-trifluoroethyl lithium, pentafluoroethyl lithium, pentafluoroethyl magnesium bromide or the like.

The amount of the metal reagent used is usually 0.5 to 2 moles, preferably 0.8 to 1.5 moles based on one mole of the compound (I-m). The reaction temperature is usually −100 to 100° C., preferably −80 to 80° C. The reaction time is several minutes to several hours.

The reaction temperature and the reaction time described above in each step, can be varied according to necessity of reaction operations, for example, the reaction temperature can be shifted to either lower or higher temperature side and the reaction time can be elongated unless adversely affecting the yield of aimed products.

The present compound (I) may be used as a herbicide as it is. However, the compound (I) may be usually formulated together with preparation auxiliaries or adjuvants into various configurations such as dusting powder, water-dispersible powder, granules or emulsion. In this case, the obtained preparation may contain at least one compound (I) in an amount of usually 0.1 to 95% by weight, preferably 0.5 to 90% by weight, more preferably 2 to 70% by weight based on the weight of the preparation. Carriers, diluents and surfactants used as the preparation auxiliaries or adjuvants are exemplified as follows. Examples of solid carriers may include usually talc, kaolin, bentonite, diatomaceous earth, white carbon, clay or the like. Examples of liquid diluents may include usually water, xylene, toluene, chlorobenzene, cyclohexane, cyclohexanone, dimethyl sulfoxide, dimethyl formamide, alcohols or the like.

Various surfactants may be selectively used according to the applications. As emulsions, there may be usually exemplified polyoxyethylene alkylaryl ether, polyoxyethylene alkyl ether, polyoxyethylene sorbitan monolaurate or the like. As dispersants, there may be usually exemplified lignin sulfonate, dibutylnaphthalene sulfonate or the like. As wetting agents, there may be usually exemplified alkyl sulfonate, alkylphenyl sulfonate or the like.

The above-mentioned preparations are used without diluting, or are used as a preparation which is diluted with a diluent such as water to the predetermined concentration. In the case where the preparations are diluted upon use, the concentration of the present compound (I) in the preparations is usually in the range of 0.01 to 1.0%. The amount of the present compound (I) is usually 0.001 to 10 kg, preferably 0.01 to 5 kg per one hectare (ha). The concentrations and amounts of the preparations used may be varied according to types of preparations used, the time, method or place of use, kinds of crops to be treated or the like and, therefore, increased or decreased concentrations or amounts may also be used without being limited to the above-specified range. Further, the present compound (I) may be used in combination with other effective ingredients, for example, germicide, insecticide, miticide, herbicide or the like.

BEST MODE FOR CARRYING OUT THE INVENTION

Next, the present invention will be described in more detail below by examples, but these examples are not intended to limit the scope of the present invention.

PRODUCTION EXAMPLE 1

Production of N-phenyl-4-methoxy-6-{3-(trifluoromethyl)phenoxy}-2-pyridine carboxamide (compound No. I-1)

(1) <Production of 2,6-dibromo-4-methoxy pyridine as an intermediate product>

1.49 g (ca. 60% in mineral oil; 0.0355×1.05 mol) of sodium hydride (hereinafter referred to merely as "NaH") was washed with hexane and suspended in tetrahydrofuran (hereinafter referred to merely as "THF"). The suspension was mixed with 1.70 g (0.0355×1.5 mol) of methanol and then with 10.00 g (0.0355 mol) of 2,6-dibromo-4-nitropyridine, and stirred at room temperature for about one hour. Further, the suspension was mixed with 0.2 g (ca. 60% in mineral oil; 0.0355×0.14 mol) of NaH, and stirred for about one hour. Next, 1.0 g (0.0355×0.9 mol) of methanol was added to the obtained suspension, and after it was determined that no foaming was caused therein, the reaction solution was distributed in ethyl acetate-saturated sodium bicarbonate water. The organic phase of the obtained reaction solution was washed with saturated brine, dried with anhydrous sodium sulfate and then concentrated, thereby obtaining an aimed product.

Yield by weight: 9.27 g; yield by percentage: 98%; solid; melting point: 131 to 133° C.; $^1$H-NMR (60 MHz, CDCl$_3$, δ): 3.79 (3H, s), 6.89 (2H, s).

(2) <Production of 2-bromo-4-methoxy-6-{3-(trifluoromethyl)phenoxy} pyridine as an intermediate product>

3.34 g (0.187×1.1 mol) of 3-(trifluoromethyl) phenol was dissolved in about 30 ml of dimethyl formamide (hereinafter referred to merely as "DMF"). The solution was further mixed with 0.78 g (ca. 60% in mineral oil; 0.0187×1.04 mol) of NaH and then with 5.00 g (0.0187 mol) of 2,6-dibromo-4-methoxy pyridine. After stirring at about 120° C. for about 2 hours, the resultant mixture was allowed to stand for cooling to room temperature. After the reaction solution was distributed in hexane-saturated sodium bicarbonate water, the organic phase of the obtained solution was washed with saturated brine and dried with anhydrous sodium sulfate. The resultant solution was concentrated and then purified by silica gel column chromatography (eluting solution: ethyl acetate/hexane), and the obtained eluate was subjected to recrystallization using hexane, thereby obtaining an aimed product.

Yield by weight: 3.23 g; yield by percentage: 50%; solid; melting point: 57 to 60° C.; $^1$H-NMR (60 MHz, CDCl$_3$, δ): 3.75 (3H, s), 6.26 (1H, d, J=2 Hz), 6.75 (1H, d, J=2 Hz), 7.0–7.6 (4H, complex).

(3) <Production of N-phenyl-4-methoxy-6-{3-(trifluoromethyl)phenoxy}-2-pyridine carboxamide (compound No. I-1)>

1.0 g (0.0029 mol) of 2-bromo-4-methoxy-6-{3-(trifluoromethyl)phenoxy} pyridine was dissolved in about 15 ml of diethyl ether. The solution was cooled in a dry ice-acetone bath in an argon atmosphere and mixed with 1.9 ml of a 1.69M-hexane solution of n-butyl lithium (0.0029× 1.1 mol; hereinafter referred to merely as "BuLi"), followed by stirring for about 10 minutes. After 0.86 g (0.0029×2.5 mol) of phenyl isocyanate dissolved in about 5 ml of diethyl ether was added to the reaction solution, the solution was removed from the bath and stirred at room temperature for about 30 minutes. The reaction solution was mixed with about 5 ml of 1.2N aqueous hydrochloric acid solution, and then distributed in ethyl acetate-water, followed by washing with saturated sodium bicarbonate water and saturated brine. The organic phase of the obtained solution was dried with anhydrous sodium sulfate, concentrated and subjected to silica gel column chromatography (eluting solution: ethyl acetate/hexane) to separate a main fraction therefrom. The fraction was concentrated and then subjected to precipitation using hexane, thereby obtaining an aimed product.

Yield by weight: 0.57 g; yield by percentage: 51%; solid; melting point: 140 to 142° C.; $^1$H-NMR (60 MHz, CDCl$_3$, δ): 3.83 (3H, s), 6.48 (1H, d, J=2 Hz), 6.8–7.7 (9H, complex), 7.52 (1H, d, J=2 Hz), 9.23 (1H, s).

PRODUCTION EXAMPLE 2

Production of N-phenyl-4-methoxy-6-{3-(trifluoromethoxy)phenoxy}-2-pyridine carboxamide (compound No. I-20)

(1) <Production of 2-bromo-4-methoxy-6-{3-(trifluoromethoxy)phenoxy} pyridine as an intermediate product>

2.00 g (0.00937×1.2 mol) of 3-(trifluoromethoxy) phenol was dissolved in about 20 ml of DMF. The solution was further mixed with 0.39 g (ca. 60% in mineral oil; 0.00937× 1.04 mol) of NaH and then with 2.50 g (0.00937 mol) of 2,6-dibromo-4-methoxy pyridine. After stirring at about 110° C. for about 4 hours, the obtained mixture was allowed to stand for cooling to room temperature. After the reaction solution was distributed in hexane-saturated sodium bicarbonate water, the organic phase of the obtained solution was washed with saturated brine and dried with anhydrous sodium sulfate. The resultant solution was concentrated and then purified by silica gel column chromatography (eluting solution: ethyl acetate/hexane), and the obtained eluate was subjected to recrystallization using hexane, thereby obtaining an aimed product.

Yield by weight: 1.40 g; yield by percentage: 41%; oily substance; $^1$H-NMR (60 MHz, CDCl$_3$, δ): 3.73 (3H, s), 6.25 (1H, d, J=2 Hz), 6.69 (1H, d, J=2 Hz), 6.7–7.5 (4H, complex).

(2) <Production of N-phenyl-4-methoxy-6-{3-(trifluoromethoxy)phenoxy)-2-pyridine carboxamide (compound No. I-20)>

1.0 g (0.0027 mol) of 2-bromo-4-methoxy-6-{3-(trifluoromethoxy)phenoxy} pyridine was dissolved in about 15 ml of diethyl ether. The obtained solution was cooled in a dry ice-acetone bath in an argon atmosphere and mixed with 2.6 ml of a 1.6M-hexane solution of BuLi (0.0027×1.5 mol), followed by stirring for about 10 minutes. After 0.74 g (0.0027×2.3 mol) of phenyl isocyanate dissolved in about 5 ml of diethyl ether was added to the reaction solution, the obtained solution was removed from the bath and stirred at room temperature for about 45 minutes. The reaction solution was mixed with about 5 ml of a 1.2N-aqueous hydrochloric acid solution, and then distributed in ethyl acetate-water, followed by washing with saturated brine. The organic phase of the obtained solution was dried with anhydrous sodium sulfate, concentrated and subjected to silica gel column chromatography (eluting solution: ethyl acetate/hexane) to separate a main fraction therefrom. The obtained fraction was concentrated and then subjected to precipitation using hexane, thereby obtaining an aimed product.

Yield by weight: 0.74 g; yield by percentage: 67%; solid; melting point: 95 to 98° C.; $^1$H-NMR (60 MHz, CDCl$_3$, δ): 3.82 (3H, s), 6.39 (1H, d, J=2 Hz), 6.6–7.6 (9H, complex), 7.44 (1H, d, J=2 Hz), 9.19 (1H, s).

PRODUCTION EXAMPLE 3

Production of N-phenyl-4-methylmercapto-6-{3-(trifluoromethyl)phenoxy}-2-pyridine carboxamide (compound No. I-22)

(1) <Production of 2,6-dibromo-4-methylmercapto pyridine as an intermediate product>

A THF solution containing 3.00 g (0.0106 mol) of 2,6-dibromo-4-nitropyridine was mixed with a 15%-aqueous solution containing 5.22 g (0.0106×1.05 mol) of sodium methyl mercaptan, and the obtained mixture was stirred at room temperature for about one hour. Further, the obtained solution was mixed with a 15%-aqueous solution containing 0.5 g (0.0106×0.1 mol) of sodium methyl mercaptan and stirred at room temperature for about one hour. After the resultant reaction solution was distributed in ethyl acetate-water, the organic phase of the solution was washed with saturated sodium bicarbonate water and saturated brine, dried with anhydrous sodium sulfate, concentrated and then subjected to precipitation by adding hexane thereto, thereby obtaining an aimed product.

Yield by weight: 2.64 g; yield by percentage: 88%; solid; melting point: 115 to 119° C.; $^1$H-NMR (60 MHz, CDCl$_3$, δ): 2.42 (3H, s), 7.04 (2H, s).

(2) <Production of 2-bromo-4-methylmercapto-6-{3-(trifluoromethyl)phenoxy} pyridine as an intermediate product>

2.06 g (0.0106×1.2 mol) of 3-(trifluoromethyl) phenol was dissolved in about 20 ml of DMF. The solution was further mixed with 0.45 g (ca. 60% in mineral oil; 0.0106× 1.06 mol) of NaH and then with 3.00 g (0.0106 mol) of 2,6-dibromo-4-methylmercapto pyridine. After stirring at about 110° C. for about 2 hours, the mixture was allowed to stand for cooling to room temperature. After the reaction solution was distributed in hexane-saturated sodium bicarbonate water, the organic phase of the obtained solution was washed with saturated brine and dried with anhydrous sodium sulfate. The resultant solution was concentrated and then purified by silica gel column chromatography (eluting solution: ethyl acetate/hexane), and the obtained eluate was subjected to recrystallization using hexane, thereby obtaining an aimed product.

Yield by weight: 2.49 g; yield by percentage: 64%; solid; melting point: 54 to 57° C.; $^1$H-NMR (60 MHz, CDCl$_3$, δ): 2.37 (3H, s), 6.50 (1H, d, J=2 Hz), 6.89 (1H, d, J=2 Hz), 7.0–7.5 (4H, complex).

(3) <Production of N-phenyl-4-methylmercapto-6-{3-(trifluoromethyl)phenoxy}-2-pyridine carboxamide (compound No. I-22)>

0.8 g (0.0022 mol) of 2-bromo-4-methylmercapto-6-{3-(trifluoromethyl)phenoxy} pyridine was dissolved in about 15 ml of diethyl ether. While cooling the obtained solution in a dry ice-acetone bath in an argon atmosphere, 1.5 ml of a 1.6M-hexane solution of BuLl (0.0022×1.1 mol) was added to the solution, followed by stirring the resultant mixture for about 10 minutes. After 0.52 g (0.0022×2.0 mol) of phenyl isocyanate dissolved in about 5 ml of diethyl ether was added to the reaction solution, the obtained solution was removed from the bath and stirred at room temperature for about 30 minutes. The reaction solution was mixed with about 5 ml of a 1.2N-aqueous hydrochloric acid solution, and then distributed in ethyl acetate-water, followed by washing with saturated sodium bicarbonate water and saturated brine. The organic phase of the obtained solution was dried with anhydrous sodium sulfate, concentrated and subjected to silica gel column chromatography (eluting solution: ethyl acetate/hexane) to separate a main fraction therefrom. The fraction was concentrated and then subjected to precipitation using hexane, thereby obtaining an aimed product.

Yield by weight: 0.52 g; yield by percentage: 59%; solid; melting point: 131 to 133° C.; $^1$H-NMR (60 MHz, CDCl$_3$, δ): 2.44 (3H, s), 6.76 (1H, d, J=2 Hz), 6.8–7.6 (9H, complex), 7.71 (1H, d, J=2 Hz), 9.11 (1H, s).

PRODUCTION EXAMPLE 4

Production of N-phenyl-4-(methyl(phenylmethyl) amino}-6-{3-(trifluoromethyl)phenoxy}-2-pyridine carboxamide (compound No. I-29)

(1) <Production of 2,6-dibromo-4-methylamino pyridine as an intermediate product>

About 10 ml of an acetonitrile solution containing 1.00 g (0.00355 mol) of 2,6-dibromo-4-nitropyridine was mixed with a 40%-aqueous solution containing 1.10 g (0.00355× 4.0 mol) of methyl amine, and the obtained mixture was stirred at room temperature for about 2 hours. After the reaction solution was distributed in ethyl acetate-water, the organic phase of the solution was washed with saturated sodium bicarbonate water and saturated brine, dried with anhydrous sodium sulfate, concentrated and then subjected to precipitation by adding hexane thereto, thereby obtaining an aimed product.

Yield by weight: 0.82 g; yield by percentage: 87%; solid; melting point: 189 to 193° C.; $^1$H-NMR (60 MHz, CDCl$_3$+ DMSO-d6, δ): 2.70 (3H, d, J=5 Hz), 6.49 (2H, s), 6.4–7.0 (1H, mult.).

(2) <Production of 4-{methyl(phenylmethyl)amino}-2,6-dibromo pyridine as an intermediate product>

3.0 g (0.011 mol) of 2,6-dibromo-4-methylamino pyridine was added to a mixed solvent comprising about 30 ml of DMF and about 50 ml of THF, and then mixed with 0.47 g (ca. 60% in mineral oil; 0.011×1.07 mol) of NaH. The obtained solution was further mixed with 2.32 g (0.011×1.2 mol) of benzyl bromide and stirred at room temperature for about 3 hours. After the reaction solution was distributed in hexane-sodium bicarbonate water, the organic phase of the solution was washed with saturated brine, dried with anhydrous sodium sulfate, and then concentrated. The obtained solid was washed out with hexane, thereby obtaining an aimed product.

Yield by weight: 3.0 g; yield by percentage: 75%; solid; melting point: 125 to 129° C.; $^1$H-NMR (60 MHz, CDCl$_3$, δ): 2.92 (3H, s), 4.45 (2H, s), 6.53 (2H, s), 6.7–7.4 (5H, complex).

(3) <Production of 2-bromo-4-{methyl(phenylmethyl) amino}-6-{3-(trifluoromethyl)phenoxy} pyridine as an intermediate product>

1.56 g (0.0080×1.2 mol) of 3-(trifluoromethyl) phenol was dissolved in about 20 ml of DMF. The solution was further mixed with 0.34 g (ca. 60% in mineral oil; 0.0080× 1.06 mol) of NaH and then with 2.85 g (0.0080 mol) of 4-{methyl(phenylmethyl)amino}-2,6-dibromo pyridine. After treating the solution under reflux for about 6 hours, the obtained reaction solution was allowed to stand for cooling to room temperature. After the reaction solution was distributed in hexane-saturated sodium bicarbonate water, the organic phase of the obtained solution was washed with saturated brine and dried with anhydrous sodium sulfate. The resultant solution was concentrated and then purified by silica gel column chromatography (eluting solution: ethyl acetate/hexane), and the obtained eluate was subjected to recrystallization using hexane, thereby obtaining an aimed product.

Yield by weight: 2.15 g; yield by percentage: 61%; solid; melting point: 84 to 87° C.; $^1$H-NMR (60 MHz, CDCl$_3$, δ): 2.92 (3H, s), 4.38 (2H, s), 5.95 (1H, d, J=2 Hz), 6.48 (1H, d, J=2 Hz), 6.7–7.6 (9H, complex).

(4) <Production of N-phenyl-4-{methyl(phenylmethyl) amino}-6-{3-(trifluoromethyl)phenoxy}-2-pyridine carboxamide (compound No. I-29)>

1.00 g (0.0023 mol) of 2-bromo-4-{methyl (phenylmethyl) amino}-6-{3-(trifluoromethyl)phenoxy} pyridine was dissolved in about 20 ml of diethyl ether. While cooling the solution in a dry ice-acetone bath in an argon atmosphere, 2.2 ml of a 1.6M-hexane solution of BuLi (0.0023×1.5 mol) was added to the solution, followed by stirring the obtained mixture for about 10 minutes. After 0.62 g (0.0023×2.3 mol) of phenyl isocyanate dissolved in about 5 ml of diethyl ether was added to the reaction solution, the obtained solution was removed from the bath and stirred at room temperature for about one hour. The reaction solution was mixed with about 5 ml of a 1.2N-aqueous hydrochloric acid solution, and then distributed in ethyl acetate-water, followed by washing with saturated sodium bicarbonate water and saturated brine. The organic phase of the obtained solution was dried with anhydrous sodium sulfate, concentrated and subjected to silica gel column chromatography (eluting solution: ethyl acetate/ hexane) to separate a main fraction therefrom. The fraction was concentrated and then subjected to precipitation using hexane, thereby obtaining an aimed product.

Yield by weight: 0.50 g; yield by percentage: 47%; solid; melting point: 111 to 114° C.; $^1$H-NMR (60 MHz, CDCl$_3$, δ): 3.03 (3H, s), 4.32 (2H, s), 6.09 (1H, d, J=2 Hz), 6.7–7.6 (15H, complex), 9.28 (1H, s).

PRODUCTION EXAMPLE 5

Production of N-phenyl-4-methylamino-6-{3-(trifluoromethyl)phenoxy}- 2-pyridine carboxamide (compound No. I-23)

0.57 g (0.0012 mol) of N-phenyl-4-{methyl(phenyl methyl)amino-6-{3-(trifluoromethyl)phenoxy}-2-pyridine carboxamide and a small amount of 10% palladium/carbon were added to about 50 ml of methanol. The obtained mixture was stirred at room temperature for about 6 hours in a hydrogen atmosphere. The obtained reaction solution was filtered using Hyflo Super Cell, and then concentrated. The obtained residue was reprecipitated using diethyl ether and hexane, thereby obtaining an aimed product.

Yield by weight: 0.37 g; yield by percentage: 80%; solid; melting point: 158 to 160° C.; $^1$H-NMR (60 MHz, CDCl$_3$, δ): 2.78 (3H, d, J=5 Hz), 5.0–5.6 (1H, mult.), 6.01 (1H, d, J=2 Hz), 6.7–7.6 (10H, complex), 9.38 (1H, s).

PRODUCTION EXAMPLE 6

Production of N-phenyl-4-dimethylamino-6-{3-(trifluoromethyl)phenoxy}-2-pyridine carboxamide (compound No. I-24)

(1) <Production of 2,6-dibromo-4-dimethylamino pyridine as an intermediate product>

2.4 g (0.0090 mol) of 2,6-dibromo-4-methylamino pyridine was added to a mixed solvent containing about 30 ml of DMF and about 40 ml of diethyl ether. Further, 0.38 g (ca. 60% in mineral oil; 0.090×1.06 mol) of NaH was added to the solution. The obtained solution was mixed with 1.54 g (0.0090×1.2 mol) of methyl iodide, and stirred at room temperature for about one hour, followed by treating the solution under reflux for about one hour. After the reaction solution was distributed in hexane-sodium bicarbonate water, the organic phase of the solution was washed with saturated brine, dried with anhydrous sodium sulfate, and concentrated. The obtained solid was washed out with hexane, thereby obtaining an aimed product.

Yield by weight: 2.39 g; yield by percentage: 95%; solid; melting point: 141 to 144° C.; $^1$H-NMR (60 MHz, CDCl$_3$, δ): 2.91 (6H, s), 6.43 (2H, s).

(2) <Production of 2-bromo-4-dimethylamino-6-{3-(trifluoromethyl)phenoxy} pyridine as an intermediate product>

1.4 g (0.0071×1.2 mol) of 3-(trifluoromethyl) phenol was dissolved in about 20 ml of DMF. The solution was further mixed with 0.30 g (ca. 60% in mineral oil; 0.0071–1.06 mol) of NaH and then with 2.00 g (0.0071 mol) of 2,6-dibromo-4-dimethylamino pyridine. After treating the solution under reflux for about 6 hours, the resultant solution was allowed to stand for cooling to room temperature. After the reaction solution was distributed in hexane-saturated sodium bicarbonate water, the organic phase of the obtained solution was washed with saturated brine and dried with anhydrous sodium sulfate, followed by concentration thereof. Thereafter, the concentrated solution was purified by silica gel column chromatography (eluting solution: ethyl acetate/ hexane) and the obtained eluate was subjected to recrystallization using hexane, thereby obtaining an aimed product.

Yield by weight: 1.67 g; yield by percentage: 65%; solid; melting point: 61 to 66° C.; $^1$H-NMR (60 MHz, CDCl$_3$, δ): 2.86 (6H, s), 6.88 (1H, d, J=2 Hz), 6.38 (1H, d, J=2 Hz), 6.9–7.5 (4H, complex).

(3) <Production of N-phenyl-4-dimethylamino-6-{3-(trifluoromethyl)phenoxy}-2-pyridine carboxamide (compound No. I-24)>

0.8 g (0.0022 mol) of 2-bromo-4-dimethylamino-6-{3-(trifluoromethyl)phenoxy} pyridine was dissolved in about 15 ml of diethyl ether. While cooling the solution in a dry ice-acetone bath in an argon atmosphere, 1.5 ml of a 1.6M-hexane solution of BuLi (0.0022×1.1 mol) was added to the solution, followed by stirring the solution for about 10 minutes. After 0.60 g (0.0022×2.3 mol) of phenyl isocyanate dissolved in about 5 ml of diethyl ether was added to the reaction solution, the solution was removed from the bath and stirred at room temperature for about 30 minutes. The reaction solution was mixed with about 5 ml of a 1.2N-aqueous hydrochloric acid solution, and then distributed in ethyl acetate-water, followed by washing with saturated sodium bicarbonate water and saturated brine. The organic phase of the obtained solution was dried with anhydrous sodium sulfate, concentrated and subjected to silica gel column chromatography (eluting solution: ethyl acetate/ hexane) to separate a main fraction therefrom. The fraction was concentrated and then precipitated with hexane, thereby obtaining an aimed product.

Yield by weight: 0.55 g; yield by percentage: 62%; solid; melting point: 135 to 138° C.; $^1$H-NMR (60 MHz, CDCl$_3$, δ): 2.96 (6H, s), 6.05 (1H, d, J=2 Hz), 6.7–7.6 (10H, complex), 9.33 (1H, s).

PRODUCTION EXAMPLE 7

Production of N-phenyl-4-methoxy-6-{3-(trifluoromethyl)phenoxy}-2-pyridine thiocarboxamide (compound No. I-26)

0.8 g (0.0023 mol) of 2-bromo-4-methoxy-6-{3-(trifluoromethyl)phenoxy} pyridine was dissolved in about 15 ml of diethyl ether. While cooling the obtained solution in a dry ice-acetone bath in an argon atmosphere, 1.5 ml of a 1.69M-hexane solution of BuLi (0.0023×1.1 mol) was added thereto, followed by stirring the solution for about 10 minutes. After 0.62 g (0.0023×2.0 mol) of phenyl isothiocyanate dissolved in about 5 ml of diethyl ether was added to the reaction solution, the solution was removed from the bath and stirred at room temperature for about 30 minutes. The reaction solution was mixed with about 5 ml of a 1.2N-aqueous hydrochloric acid solution, and then distributed in ethyl acetate-water, followed by washing with saturated brine. The organic phase of the obtained solution was dried with anhydrous sodium sulfate, concentrated and subjected to silica gel column chromatography (eluting solution: ethyl acetate/hexane) to separate a main fraction therefrom. The fraction was concentrated and then precipitated with hexane, thereby obtaining an aimed product.

Yield by weight: 0.53 g; yield by percentage: 57%; solid; melting point: 126 to 128° C.; $^1$H-NMR (60 MHz, CDCl$_3$, δ): 3.79 (3H, s), 6.43 (1H, J=2 Hz), 6.8–7.7 (9H, complex), 7.92 (1H, d, J=2 Hz), 11.32 (1H, s).

PRODUCTION EXAMPLE 8

Production of N-(4-methylphenyl)-4-methoxy-6-(3-methylphenoxy)-2-pyridine carboxamide
(compound No. I-28)

(1) <Production of N-(4-methylphenyl)-6-bromo-4-methoxy-2-pyridine carboxamide as an intermediate product>

2.0 g (0.0075 mol) of 2,6-dibromo-4-methoxy pyridine was dissolved in about 30 ml of diethyl ether. While cooling the solution in a dry ice-acetone bath in an argon atmosphere, 6.0 ml of a 1.6M-hexane solution of BuLi (0.0075×1.3 mol) was added thereto, followed by stirring the solution for about 10 minutes. After 2.0 g (0.0075×2.0 mol) of 4-methyl phenyl isocyanate dissolved in about 5 ml of diethyl ether was added to the reaction solution, the solution was removed from the bath and stirred at room temperature for about 40 minutes. The reaction solution was mixed with about 10 ml of a 1.2N-aqueous hydrochloric acid solution, and then distributed in ethyl acetate-saturated sodium bicarbonate water, followed by washing with saturated brine. The organic phase of the obtained solution was dried with anhydrous sodium sulfate, concentrated and subjected to silica gel column chromatography (eluting solution: ethyl acetate/hexane) to separate a main fraction therefrom. The fraction was concentrated and then precipitated with hexane, thereby obtaining an aimed product.

Yield by weight: 1.38 g; yield by percentage: 57%; solid; melting point: 153 to 157° C.; $^1$H-NMR (60 MHz, CDCl$_3$, δ): 2.28 (3H, s), 3.82 (3H, s), 7.02 (1H, d, J=2 Hz), 7.09 (2H, d, J=8 Hz), 7.56 (2H, d, J=8 Hz), 7.68 (1H, d, J=2 Hz), 9.53 (1H, s).

(2) <Production of N-(4-methylphenyl)-4-methoxy-6-(3-methylphenoxy)-2-pyridine carboxamide (compound No. I-28)>

0.45 g (0.0019×2.2 mol) of 3-methyl phenol was dissolved in about 10 ml of DMF. The obtained solution was further mixed with 0.15 g (ca. 60% in mineral oil; 0.0019×2.0 mol) of NaH and then with 0.60 g (0.0019 mol) of N-(4-methylphenyl)-6-bromo-4-methoxy-2-pyridine carboxamide. After adding 0.19 g (0.0019×1.0 mol) of copper chloride (I), the solution was stirred at about 100° C. for about 4 hours, and then allowed to stand for cooling to room temperature. After the reaction solution was distributed in hexane-saturated sodium bicarbonate water, the organic phase of the solution was washed with saturated brine and dried with anhydrous sodium sulfate, followed by concentration thereof. Thereafter, the concentrated solution was purified by silica gel column chromatography (eluting solution: ethyl acetate/hexane), thereby obtaining an aimed product.

Yield by weight: 0.50 g; yield by percentage: 77%; solid; melting point: 110 to 114° C.; $^1$H-NMR (60 MHz, CDCl$_3$, δ): 2.25 (3H, s), 2.33 (3H, s), 3.78 (3H, s), 6.37 (1H, d, J=2 Hz), 6.4–7.6 (8H, complex), 7.47 (1H, d, J=2 Hz), 9.42 (1H, s).

PRODUCTION EXAMPLE 9

Production of N-(n-propyl)-4-methoxy-6-{3-(trifluoromethyl)phenoxyl-2-pyridine carboxamide
(compound No. I-33)

0.8 g (0.0023 mol) of 2-bromo-4-methoxy-6-{3-(trifluoromethyl)phenoxy} pyridine was dissolved in about 15 ml of diethyl ether. While cooling the obtained solution in a dry ice-acetone bath in an argon atmosphere, 1.6 ml of a 1.6M-hexane solution of BuLi (0.0023×1.1 mol) was added thereto, followed by stirring the mixed solution for about 10 minutes. After 0.39 g (0.0023×2.0 mol) of n-propyl isocyanate dissolved in about 5 ml of diethyl ether was added to the reaction solution, the solution was removed from the bath and stirred at room temperature for about one hour. The reaction solution was mixed with about 5 ml of 1.0N aqueous hydrochloric acid solution, and then distributed in ethyl acetate-saturated sodium bicarbonate water, followed by washing with saturated brine. The organic phase of the obtained solution was dried with anhydrous sodium sulfate, concentrated and purified by silica gel column chromatography (eluting solution: ethyl acetate/hexane), thereby obtaining an aimed product.

Yield by weight: 0.65 g; yield by percentage: 80%; solid; melting point: 60 to 64° C.; $^1$H-NMR (60 MHz, CDCl$_3$, δ): 0.81 (3H, t, J=7 Hz), 1.46 (2H, sext, J=7 Hz), 3.38 (2H, q, J=6.4 Hz), 3.81 (3H, s), 6.41 (1H, d, J=2 Hz), 7.0–7.8 (6H, complex).

PRODUCTION EXAMPLE 10

Production of N-(i-propyl)-4-methoxy-6-{3-(trifluoromethylmercapto)phenoxy}-2-pyridine carboxamide (compound No. I-40)

(1) <Production of N-(i-propyl)-6-bromo-4-methoxy-2-pyridine carboxamide as an intermediate product>

1.0 g (0.0037 mol) of 2,6-dibromo-4-methoxy pyridine was suspended in about 15 ml of diethyl ether. While cooling the obtained suspension in a dry ice-acetone bath in an argon atmosphere, 2.6 ml of a 1.6M-hexane solution of BuLi (0.0037×1.1 mol) was added thereto, followed by stirring the suspension for about 10 minutes. After 0.64 g (0.0037×2.0 mol) of i-propyl isocyanate dissolved in about 5 ml of diethyl ether was added to the reaction solution, the solution was removed from the bath and stirred at room temperature for about 40 minutes. The reaction solution was mixed with about 5 ml of a 1.0N-aqueous hydrochloric acid solution, and then distributed in ethyl acetate-saturated sodium bicarbonate water, followed by washing with saturated brine. The organic phase of the obtained solution was dried with anhydrous sodium sulfate, concentrated and purified by silica gel column chromatography (eluting solution: ethyl acetate/hexane), thereby obtaining an aimed product.

Yield by weight: 0.76 g; yield by percentage: 74%; solid; melting point: 70 to 76° C.; $^1$H-NMR (60 MHz, CDCl$_3$, δ): 1.25 (6H, d, J=6.4 Hz), 3.82 (3H, s), 3.8–4.6 (1H, mult.), 6.98 (1H, d, J=2 Hz), 7.0–7.9 (1H, br), 7.61 (1H, d, J=2 Hz).

(2) <Production of N-(i-propyl)-4-methoxy-6-{3-(trifluoromethylmercapto)phenoxy}-2-pyridine carboxamide (compound No. I-40)>

1.25 g (0.0029×2.2 mol) of 3-(trifluoromethylthio) phenol was dissolved in about 10 ml of DMF. The obtained solution was further mixed with 0.23 g (ca. 60% in mineral oil; 0.0029×2.0 mol) of NaH and then with 0.80 g (0.0029 mol) of N-(i-propyl)-6-bromo-4-methoxy-2-pyridine carboxamide. After adding 0.15 g (0.0029×0.5 mol) of copper chloride (I), the obtained solution was stirred at about 110° C. for about 6 hours, and then allowed to stand for cooling to room temperature. After the reaction solution was distributed in ethyl acetate-saturated sodium bicarbonate water, the organic phase of the solution was washed with saturated brine and dried with anhydrous sodium sulfate, followed by concentration thereof. Thereafter, the concentrated solution was purified by silica gel column chromatography (eluting solution: ethyl acetate/hexane), thereby obtaining an aimed product.

Yield by weight: 0.92 g; yield by percentage: 81%; oily substance; $^1$H-NMR (60 MHz, CDCl$_3$, δ): 1.10 (6H, d, J=6.4 Hz), 3.7–4.5 (1H, mult.), 3.79 (3H, s), 6.38 (1H, d, J=2 Hz), 6.4–7.6 (6H, complex).

PRODUCTION EXAMPLE 11

Production of N-benzyl-4-methoxy-6-{3-(trifluoromethyl)phenoxy}-2-pyridine carboxamide (compound No. I-45)

(1) <Production of N-benzyl-6-bromo-4-methoxy-2-pyridine carboxamide as an intermediate product>

1.0 g (0.0037 mol) of 2,6-dibromo-4-methoxy pyridine was suspended in about 15 ml of diethyl ether. While cooling the obtained suspension in a dry ice-acetone bath in an argon atmosphere, 2.6 ml of a 1.6M-hexane solution of BuLi (0.0037×1.1 mol) was added thereto, followed by stirring the suspension for about 10 minutes. After 0.75 g (0.0037×1.5 mol) of benzyl isocyanate dissolved in about 5 ml of diethyl ether was added to the reaction solution, the obtained solution was removed from the bath and stirred at room temperature for about 40 minutes. The reaction solution was mixed with about 5 ml of a 1.0N-aqueous hydrochloric acid solution, and then distributed in ethyl acetate-saturated sodium bicarbonate water, followed by washing with saturated brine. The organic phase of the obtained solution was dried with anhydrous sodium sulfate, concentrated and purified by silica gel column chromatography (eluting solution: ethyl acetate/hexane), thereby obtaining an aimed product.

Yield by weight: 1.04 g; yield by percentage: 86%; solid; melting point: 107 to 111° C.; $^1$H-NMR (60 MHz, CDCl$_3$, δ): 3.75 (3H, s), 4.52 (2H, d, J=6 Hz), 6.94 (1H, d, J=2 Hz), 7.20 (5H, s), 7.59 (1H, d, J=2 Hz), 7.8–8.4 (1H, br).

(2) <Production of N-benzyl-4-methoxy-6-{3-(trifluoromethyl)phenoxy}-2-pyridine carboxamide (compound No. I-45)>

1.04 g (0.0029×2.2 mol) of 3-(trifluoromethyl) phenol was dissolved in about 10 ml of DMF. The obtained solution was further mixed with 0.24 g (ca. 60% in mineral oil; 0.0029×2.0 mol) of NaH and then with 0.94 g (0.0029 mol) of N-benzyl-6-bromo-4-methoxy-2-pyridine carboxamide. After adding 0.15 g (0.0029×0.5 mol) of copper chloride (I), the solution was stirred at about 120° C. for about 5 hours, and then allowed to stand for cooling to room temperature. After the reaction solution was distributed in ethyl acetate-saturated sodium bicarbonate water, the organic phase of the solution was washed with saturated brine and dried with anhydrous sodium sulfate, followed by concentration thereof. Thereafter, the concentrated solution was purified by silica gel column chromatography (eluting solution: ethyl acetate/hexane), thereby obtaining an aimed product.

Yield by weight: 0.72 g; yield by percentage: 63%; solid; melting point: 87 to 92° C.; $^1$H-NMR (60 MHz, CDCl$_3$, δ): 3.83 (3H, s), 4.45 (2H, d, J=6 Hz), 6.45 (1H, d, J=2 Hz), 6.9–7.9 (10H, complex), 7.51 (1H, d, J=2 Hz).

PRODUCTION EXAMPLE 12

Production of N-cyclopropyl-4-methoxy-6-{3-(trifluoromethyl)phenoxy}-2-pyridine carboxamide (compound No. I-48)

0.40 g (0.00128 mol) of 4-methoxy-6-{3-(trifluoromethyl)phenoxy}-2-picolinic acid was mixed with 0.3 g (0.00128×2.0 mol) thionyl chloride and then with about 10 ml of benzene and a small amount of DMF, followed by treating the obtained mixture under reflux for about 30 minutes. The reaction solution was concentrated and, thereafter, mixed with methylene chloride and then with 0.18 g (0.00128×2.5 mol) of cyclopropyl amine, followed by stirring at room temperature for about 30 minutes. The reaction solution was distributed in ethyl acetate-saturated sodium bicarbonate water, and washed with saturated brine. The organic phase of the solution was dried with anhydrous sodium sulfate, and concentrated. Thereafter, the concentrated solution was purified by silica gel column chromatography (eluting solution: ethyl acetate/hexane), thereby obtaining an aimed product.

Yield by weight: 0.37 g; yield by percentage: 82%; solid; melting point: 106 to 109° C.; $^1$H-NMR (60 MHz, CDCl$_3$, δ): 0.1–1.1 (4H, complex), 2.4–3.1 (1H, mult.), 3.83 (3H, s), 6.43 (1H, d, J=2 Hz), 7.0–7.8 (6H, complex).

PRODUCTION EXAMPLE 13

Production of N-(i-propyl)-4-methylmercapto-6-{3-(trifluoromethyl)phenoxy}-2-pyridine carboxamide (compound No. I-55)

0.75 g (0.0021 mol) of 2-bromo-4-methylmercapto-6-{3-(trifluoromethyl)phenoxy}-2-pyridine was suspended in about 15 ml of diethyl ether. While cooling the obtained suspension in a dry ice-acetone bath in an argon atmosphere, 1.4 ml of a 1.65M-hexane solution of BuLi (0.00206×1.1 mol) was added thereto, followed by stirring the suspension for about 10 minutes. After 0.35 g (0.00206×2.0 mol) of isopropyl isocyanate dissolved in about 10 ml of diethyl ether was added to the reaction solution, the solution was removed from the bath and stirred at room temperature for about one hour. The reaction solution was mixed with about 5 ml of a 1N-aqueous hydrochloric acid solution, and then distributed in ethyl acetate-saturated sodium bicarbonate water, followed by washing with saturated brine. The organic phase of the obtained solution was dried with anhydrous sodium sulfate, concentrated and purified by silica gel column chromatography (eluting solution: ethyl acetate/hexane) and reversed phase column (Lobor LiCHroprep RP-10; eluting solution: acetonitrile/water), thereby obtaining an aimed product.

Yield by weight: 0.36 g; yield by percentage: 47%; solid; melting point: 66 to 69° C.; $^1$H-NMR (60 MHz, CDCl$_3$, δ): 1.09 (6H, d, J=6.4 Hz), 2.50 (3H, s), 3.6–4.4 (1H, mult.), 6.78 (1H, d, J=2 Hz), 6.8–7.7 (5H, complex), 7.72 (1H, d, J=2 Hz).

PRODUCTION EXAMPLE 14

Production of N-(i-propyl)-4-dimethylamino-6-{3-(trifluoromethyl)phenoxy}-2-pyridine carboxamide (compound No. I-57)

0.75 g (0.0021 mol) of 2-bromo-4-dimethylamino-6-{3-(trifluoromethyl)phenoxy} pyridine was suspended in about 15 ml of diethyl ether. While cooling the obtained suspension in a dry ice-acetone bath in an argon atmosphere, 1.4 ml of a 1.65M-hexane solution of BuLi (0.0021×1.1 mol) was added thereto, followed by stirring the suspension for about 10 minutes. After 0.35 g (0.0021×2.0 mol) of isopropyl isocyanate dissolved in about 10 ml of diethyl ether was added to the reaction solution, the obtained solution was removed from the bath and stirred at room temperature for about one hour. The reaction solution was mixed with about 5 ml of a 1N-hydrochloric acid aqueous solution, and then distributed in ethyl acetate-saturated sodium bicarbonate water, followed by washing with saturated brine. The organic phase of the obtained solution was dried with anhydrous sodium sulfate, concentrated and purified by silica gel column chromatography (eluting solution: ethyl acetate/hexane) and reversed phase column (Lobor LiCHroprep RP-10; eluting solution: acetonitrile/water), thereby obtaining an aimed product.

Yield by weight: 0.22 g; yield by percentage: 29%; solid; melting point: 108 to 110° C.; $^1$H-NMR (60 MHz, CDCl$_3$, δ): 1.10 (6H, d, J=6.4 Hz), 3.00 (6H, s), 3.6–4.4 (1H, mult.), 6.06 (1H, d, J=2 Hz), 6.9–7.7 (6H, complex).

PRODUCTION EXAMPLE 15

Production of N-(i-propyl)-4-{methyl(phenylmethyl)amino}-6-{3-(trifluoromethyl)phenoxy}-2-pyridine carboxamide (compound No. I-58)

2.22 g (0.0051 mol) of 2-bromo-4-{methyl(phenylmethyl)amino}-6-{3-(trifluoromethyl)phenoxy}pyridine was suspended in about 30 ml of diethyl ether. While cooling the obtained suspension in a dry ice-acetone bath in an argon atmosphere, 3.4 ml of a 1.65M-hexane solution of BuLi (0.0051×1.1 mol) was added thereto, followed by stirring the suspension for about 10 minutes. After 0.86 g (0.0051×2.0 mol) of isopropyl isocyanate dissolved in about 10 ml of diethyl ether was added to the reaction solution, the obtained solution was removed from the bath and stirred at room temperature for about one hour. The reaction solution was mixed with about 10 ml of a 1N-hydrochloric acid aqueous solution, and then distributed in ethyl acetate-saturated sodium bicarbonate water, followed by washing with saturated brine. The organic phase of the obtained solution was dried with anhydrous sodium sulfate, concentrated and purified by silica gel column chromatography (eluting solution: ethyl acetate/hexane), thereby obtaining an aimed product.

Yield by weight: 1.24 g; yield by percentage: 55%; oily substance; $^1$H-NMR (60 MHz, CDCl$_3$, δ): 1.09 (6H, d, J=6.4 Hz), 3.06 (6H, s), 3.6–4.4 (1H, mult.), 4.52 (2H, s), 6.09 (1H, d, J=2 Hz), 6.8–7.6 (11H, complex).

PRODUCTION EXAMPLE 16

Production of N-(i-propyl)-4-methylamino-6-{3-(trifluoromethyl)phenoxy}-2-pyridine carboxamide (compound No. I-56)

1.12 g (0.0012 mol) of N-(i-propyl)-4-(methyl(phenylmethyl)amino}-6-{3-(trifluoromethyl)phenoxy}-2-pyridine carboxamide were mixed with methanol and then with a small amount of 10% palladium/carbon and acetic acid. The obtained mixture was stirred at room temperature for about 16 hours in a hydrogen atmosphere. The obtained reaction solution was filtered using Hyflo Super Cell and then concentrated. The concentrate was purified by silica gel column chromatography (eluting solution: ethyl acetate/hexane), thereby obtaining an aimed product.

Yield by weight: 0.81 g; yield by percentage: 91%; solid; melting point: 89 to 90° C.; $^1$H-NMR (60 MHz, CDCl$_3$, δ): 1.09 (6H, d, J=6.4 Hz), 2.79 (3H, d, J=5.6 Hz), 3.5–4.4 (1H, mult.), 4.7–5.4 (1H, br), 5.93 (1H, d, J=2 Hz), 6.8–7.7 (6H, complex).

PRODUCTION EXAMPLE 17

Production of N-{2-(ethylsulfonyl)ethyl}-4-methoxy-6-{3-(trifluoromethyl)phenoxy}-2-pyridine carboxamide (compound No. I-68) and N-{2-(ethylsulfinyl)ethyl}-4-methoxy-6-{3-(trifluoromethyl)phenoxy}-2-pyridine carboxamide (compound No. I-69)

0.6 g (0.0015 mol) of N-{2-(ethylmercapto)ethyl}-4-methoxy-6-{3-(trifluoromethyl)phenoxy}-2-pyridine carboxamide (I-67) was dissolved in chloroform and mixed with 0.57 g (not less than 70%; 0.0015×1.5 mol) of m-chloro-perbenzoic acid, followed by stirring at room temperature for about 4 hours. The reaction solution was distributed in ethyl acetate-saturated sodium bicarbonate water and then washed with saturated brine. The organic phase of the obtained solution was dried with anhydrous sodium sulfate, concentrated and purified by silica gel column chromatography (eluting solution: ethyl acetate/hexane), thereby obtaining an aimed product.

(Compound No. I-68)

Yield by weight: 0.46 g; yield by percentage: 71%; solid; melting point: 92 to 94° C.; $^1$H-NMR (60 MHz, CDCl$_3$, δ): 1.31 (3H, t, J=7 Hz), 2.95 (2H, q, J=7 Hz), 3.16 (2H, t, J=6.4 Hz), 3.78 (2H, q, J=6.4 Hz), 3.85 (3H, s), 6.49 (1H, d, J=2 Hz), 7.1–7.7 (5H, complex), 7.92 (1H, t, J=6.4 Hz).

(Compound No. I-69)

Yield by weight: 0.12 g; yield by percentage: 19%; solid; melting point: 77 to 79° C.;

$^1$H-NMR (60 MHz, CDCl$_3$, δ): 1.27 (3H, t, J=7 Hz), 2.69 (2H, q, J=7 Hz), 2.6–3.1 (2H, complex), 3.75 (2H, q, J=6.4 Hz), 3.86 (3H, s), 6.46 (1H, d, J=2 Hz), 7.0–7.6 (5H, complex), 7.92 (1H, br).

PRODUCTION EXAMPLE 18

Production of 4-methoxy-6-{3-(trifluoromethyl)phenoxy}-2-pyridine carboxamide (compound No. I-123)

1.0 g (0.0032 mol) of 4-methoxy-6-(3-(trifluoromethyl)phenoxy}-2-pyridine carboxylic acid was mixed with 0.75 g (0.0032×2.0 mol) of thionyl chloride and then with about 10 ml of benzene and a small amount of DMF, followed by treating the obtained mixture under reflux for about 30 minutes. The reaction solution was concentrated and, thereafter, mixed with methylene chloride and then with 0.56 g (29% aqueous solution; 0.0032×3.0 mol) of ammonia water, followed by stirring at room temperature for about 30 minutes. The reaction solution was distributed in ethyl acetate-1N hydrochloric acid aqueous solution, and washed with saturated sodium bicarbonate water and saturated brine. The organic phase of the solution was dried with anhydrous sodium sulfate and then concentrated. Thereafter, the concentrated solution was purified by silica gel column chromatography (eluting solution: ethyl acetate/hexane), thereby obtaining an aimed product.

Yield by weight: 0.88 g; yield by percentage: 84%; solid; melting point: 150 to 151° C.; $^1$H-NMR (60 MHz, CDCl$_3$, δ): 3.85 (3H, s), 6.21 (1H, br), 6.50 (1H, d, J=2 Hz), 6.9–7.8 (6H, complex).

PRODUCTION EXAMPLE 19

Production of N-(2,2-dichlorovinyl)-4-methoxy-6-{3-(trifluoromethyl)phenoxy}-2-pyridine carboxamide (compound No. I-83)

(1) <Production of N-(1-hydroxy-2,2,2-trichloroethyl)-4-methoxy-6-{3-(trifluoromethyl)phenoxy}-2-pyridine carboxamide as an intermediate product>

1.0 g (0.0032 mol) of 4-methoxy-6-{3-(trifluoromethyl)phenoxy}-2-pyridine carboxamide was dissolved in benzene and mixed with 0.93 g (0.0032×2.0 mol) of chloral, followed by treating the obtained solution under reflux for about 5 hours. The reaction solution was concentrated and then distributed in ethyl acetate-saturated sodium bicarbonate water, followed by washing with saturated brine. The organic phase of the obtained solution was dried with anhydrous sodium sulfate, concentrated and purified by silica gel column chromatography (eluting solution: ethyl acetate/hexane), thereby obtaining an aimed product.

Yield by weight: 1.42 g; yield by percentage: 96%; solid; melting point: 123 to 125° C.; $^1$H-NMR (60 MHz, CDCl$_3$, δ): 3.84 (3H, s), 5.36 (1H, s), 5.81 (1H, d, J=9.5 Hz), 6.54 (1H, d, J=2 Hz), 7.0–7.7 (5H, complex), 8.27 (1H, d, J=9.5 Hz).

(2) <Production of N-(2,2-dichlorovinyl)-4-methoxy-6-{3-(trifluoromethyl)phenoxy}-2-pyridine carboxamide (compound No. I-83)>

1.0 g (0.0022 mol) of N-(1-hydroxy- 2,2,2-trichloroethyl)-4-methoxy-6-{3-(trifluoromethyl)phenoxy}-2-pyridine carboxamide was dissolved in about 10 ml of acetic acid. The obtained solution was mixed with 0.29 g (0.0022×2.0 mol) of zinc dust and stirred at about 50° C. for about 5 hours. The reaction solution was distributed in ethyl acetate-water and washed with saturated sodium bicarbonate water and saturated brine. The organic phase of the solution was dried with anhydrous sodium sulfate, concentrated and purified by silica gel column chromatography (eluting solution: ethyl acetate/hexane), thereby obtaining an aimed product.

Yield by weight: 0.41 g; yield by percentage: 46%; solid; melting point: 124 to 126° C.; $^1$H-NMR (60 MHz, CDCl$_3$, δ): 3.87 (3H, s), 6.56 (1H, d, J=2 Hz), 7.18 (1H, d, J=11 Hz), 7.1–7.8 (5H, complex), 9.05 (1H, d, J=11 Hz).

PRODUCTION EXAMPLE 20

Production of N-(2-oxobutyl)-4-methoxy-6-{3-(trifluoromethyl)phenoxy}-2-pyridine carboxamide (compound No. I-86)

0.79 g (0.00225 mol) of N-{(2-cyano)methyl}-4-methoxy-6-{3-(trifluoromethyl)phenoxy}-2-pyridine carboxamide (I-84) was dissolved in about 15 ml of THF. While cooling the obtained solution in a dry ice-acetone bath in an argon atmosphere, 5.0 ml of a 1.0M-THF solution containing ethyl magnesium bromide (0.0022×2.3 mol) was added thereto. The reaction solution was removed from the bath and stirred at room temperature for about one hour. The reaction solution was mixed with about 10 ml of a 4N-hydrochloric acid aqueous solution, and then distributed in ethyl acetate-water, followed by washing with saturated sodium bicarbonate water and saturated brine. Further, the reaction solution was dried with anhydrous sodium sulfate, concentrated and then mixed with about 10 ml of THF and about 10 ml of 4N hydrochloric acid aqueous solution, followed by treating the obtained solution under reflux for about 30 minutes. The obtained reaction solution was also distributed in ethyl acetate-water and washed with saturated sodium bicarbonate water and saturated brine. The organic phase of the obtained solution was dried with anhydrous sodium sulfate, concentrated and purified by silica gel column chromatography (eluting solution: ethyl acetate/hexane). The hexane eluate was further subjected to recrystallization, thereby obtaining an aimed product.

Yield by weight: 0.11 g; yield by percentage: 13%; solid; melting point: 100 to 103° C.; $^1$H-NMR (60 MHz, CDCl$_3$, δ): 1.06 (3H, t, J=7 Hz), 2.42 (2H, q, J=7 Hz), 3.85 (3H, s), 4.13 (2H, d, J=5 Hz), 6.48 (1H, d, J=2 Hz), 7.1–7.7 (5H, complex), 7.7–8.2 (1H, br).

PRODUCTION EXAMPLE 21

Production of N-(ethoxymethyl)-4-methoxy-6-{3-(trifluoromethyl)phenoxy}-2-pyridine carboxamide (compound No. I-87)

1.0 g (0.0032 mol) of 4-methoxy-6-{3-(trifluoromethyl)phenoxy}-2-pyridine carboxamide was dissolved in a mixed solvent containing about 20 ml of benzene and about 10 ml of DMF, and the obtained solution was mixed with 0.14 g (ca. 60% in mineral oil; 0.0032×1.1 mol) of NaH, followed by treating the solution under reflux for several minutes. Thereafter, the resultant reaction solution was mixed with 0.61 g (0.0032×2.0 mol) of chloromethyl ethyl ether, followed by treating the solution under reflux for about 3 hours. The reaction solution was distributed in ethyl acetate-saturated sodium bicarbonate water and then washed with saturated brine. The organic phase of the solution was dried with anhydrous sodium sulfate, concentrated and purified by silica gel column chromatography (eluting solution: ethyl acetate/hexane), thereby obtaining an aimed product.

Yield by weight: 0.58 g; yield by percentage: 49%; solid; melting point: 44 to 47° C.; $^1$H-NMR (60 MHz, CDCl$_3$, δ): 1.14 (3H, t, J=7 Hz), 3.49 (2H, q, J=7 Hz), 3.88 (3H, s), 4.77 (2H, d, J=7 Hz), 6.52 (1H, d, J=2 Hz), 7.0–7.7 (5H, complex), 7.7–8.4 (1H, br).

PRODUCTION EXAMPLE 22

Production of N-(1-methoxy-2,2,2-trifluoroethyl)-4-methoxy-6-{3-(trifluoromethyl)phenoxy}-2-pyridine carboxamide (compound No. I-88)

(1) <Production of N-{(1-hydroxy-2,2,2-trifluoro)ethyl}-4-methoxy-6-{3-(trifluoromethyl)phenoxy}-2-pyridine carboxamide as an intermediate product>

4-methoxy-6-{3-(trifluoromethyl)phenoxy}-2-pyridine carboxamide was dissolved in benzene and mixed with 0.36 g (0.0026×1.2 mol) of trifluoroacetaldehyde hydrate, followed by treating the obtained solution under reflux for about 5 hours. The reaction solution was concentrated and then distributed in ethyl acetate-saturated sodium bicarbonate water, followed by washing with saturated brine. The organic phase of the obtained solution was dried with anhydrous sodium sulfate, concentrated and purified by silica gel column chromatography (eluting solution: ethyl acetate/hexane), thereby obtaining an aimed product.

Yield by weight: 0.70 g; yield by percentage: 67%; solid; melting point: 102 to 104° C.; $^1$H-NMR (60 MHz, CDCl$_3$, δ): 3.82 (3H, s), 5.3–6.2 (1H, mult.), 6.52 (1H, d, J=2 Hz), 6.9–7.7 (5H, complex), 8.17 (1H, d, J=10 Hz).

(2) <Production of N-{(1-methoxy-2,2,2-trifluoro)ethyl}-4-methoxy-6-{3-(trifluoromethyl)phenoxy}-2-pyridine carboxamide (compound No. I-88)>

0.6 g (0.0015 mol) of N-(1-hydroxy-2,2,2-trifluoroethyl)-4-methoxy-6-{3-(trifluoromethyl)phenoxy}-2-pyridine carboxamide was dissolved in a mixed solvent of dichloromethane and DMF. The obtained solution was mixed with 0.064 g (ca. 60% in mineral oil; 0.0015×1.1 mol) of NaH and then with 0.42 g (0.0015×2.0 mol) of methyl iodide, followed by treating the solution under reflux for about 8 hours. The reaction solution was distributed in hexane-saturated sodium bicarbonate water and washed with saturated brine. The organic phase of the solution was dried with anhydrous sodium sulfate, concentrated and purified by silica gel column chromatography (eluting solution: ethyl acetate/hexane), thereby obtaining an aimed product.

Yield by weight: 0.35 g; yield by percentage: 56%; oily substance; $^1$H-NMR (60 MHz, CDCl$_3$, δ): 3.39 (3H, s), 3.88 (3H, s), 5.1–5.8 (2H, complex), 6.55 (1H, d, J=2 Hz), 7.1–7.6 (5H, complex), 7.84 (1H, d, J=10 Hz).

PRODUCTION EXAMPLE 23

Production of N-(2-mercaptoethyl)-4-methoxy-6-{3-(trifluoromethyl)phenoxy-2-pyridine carboxamide (compound No. I-91)

3.0 g (0.0096 mol) of 4-methoxy-6-{3-(trifluoromethyl) phenoxy}-2-pyridine carboxylic acid was mixed with 2.25 g (0.0096×2.0 mol) of thionyl chloride and then with about 50 ml of benzene and a small amount of DMF, followed by treating the obtained mixture under reflux for about 30 minutes. The reaction solution was concentrated and mixed with methylene chloride and then with 1.63 g (0.0096×1.5 mol) of cysteamine hydrochloride and 2.42 g (0.0096×2.5 mol) of triethyl amine, followed by stirring at room temperature for about one hour. The reaction solution was distributed in ethyl acetate-saturated sodium bicarbonate water, and washed with saturated brine. The organic phase of the solution was dried with anhydrous sodium sulfate, concentrated and purified by silica gel column chromatography (eluting solution: ethyl acetate/hexane), thereby obtaining an aimed product.

Yield by weight: 2.84 g; yield by percentage: 80%; solid; melting point: 75 to 76° C.; $^1$H-NMR (60 MHz, CDCl$_3$, δ): 1.20 (1H, t, J=8 Hz), 2.2–2.9 (2H, complex), 3.45 (2H, q, J=6 Hz), 3.84 (3H, s), 6.47 (1H, d, J=2 Hz), 7.0–8.0 (6H, complex).

PRODUCTION EXAMPLE 24

Production of N-{2-(2-fluoroethylmercapto)ethyl}-4-methoxy-6-{3-(trifluoromethyl)phenoxy}-2-pyridine carboxamide (compound No. I-92)

1.0 g (0.0027 mol) of N-(2-mercaptoethyl)-4-methoxy-6-{3-(trifluoromethyl)phenoxy}-2-pyridine carboxamide (compound No. I-91) was dissolved in DMF, and the obtained solution was mixed with 0.12 g (ca. 60% in mineral oil; 0.0027×1.1 mol) of NaH and then with 0.68 g (0.0027×2.0 mol) of 1-bromo-2-fluoroethane, followed by stirring the solution for about one hour. The reaction solution was distributed in ethyl acetate-saturated sodium bicarbonate water and then washed with saturated brine. The organic phase of the solution was dried with anhydrous sodium sulfate, concentrated and purified by silica gel column chromatography (eluting solution: ethyl acetate/hexane), thereby obtaining an aimed product.

Yield by weight: 0.86 g; yield by percentage: 77%; solid; melting point: 82 to 84° C.; $^1$H-NMR (60 MHz, CDCl$_3$, δ): 2.2–3.1 (4H, complex), 3.51 (2H, q, J=6 Hz), 3.81 (3H, s), 4.41 (2H, dt, J=47 Hz, 6 Hz), 6.45 (1H, d, J=2 Hz), 6.7–8.0 (6H, complex).

PRODUCTION EXAMPLE 25

Production of N-hydroxy-4-methoxy-6-{3-(trifluoromethyl)phenoxy}-2-pyridine carboxamide (compound No. I-96)

3.0 g (0.0096 mol) of 4-methoxy-6-(3-(trifluoromethyl)phenoxy}-2-pyridine carboxylic acid was mixed with 2.25 g (0.0096×2.0 mol) of thionyl chloride and then with about 50 ml of benzene and a small amount of DMF, followed by treating the obtained mixture under reflux for about 30 minutes. The reaction solution was concentrated and mixed with methylene chloride and then with 1.32 g (0.0096×2.0 mol) of hydroxyl amine hydrochloride and 2.42 g (0.0096× 2.5 mol) of triethyl amine, followed by stirring at room temperature for about one hour. The reaction solution was distributed in ethyl acetate-saturated sodium bicarbonate water, and washed with saturated brine. The organic phase of the solution was dried with anhydrous sodium sulfate, concentrated and purified by silica gel column chromatography (eluting solution: ethyl acetate/hexane), thereby obtaining an aimed product.

Yield by weight: 2.51 g; yield by percentage: 80%; solid; melting point: 120 to 122° C.; $^1$H-NMR (60 MHz, CDCl$_3$, δ): 3.76 (3H, s), 6.36 (1H, d, J=2 Hz), 6.9–7.7 (5H, complex), 9.29 (2H, brs).

PRODUCTION EXAMPLE 26

Production of N-methoxy-4-methoxy-6-{3-(trifluoromethyl)phenoxy}-2-pyridine carboxamide (compound No. I-97)

0.4 g (0.00128 mol) of 4-methoxy-6-{3-(trifluoromethyl)phenoxy)-2-pyridine carboxylic acid was mixed with 0.3 g (0.00128×2.0 mol) of thionyl chloride and then with about 10 ml of benzene and a small amount of DMF, followed by treating the obtained mixture under reflux for about 30 minutes. The reaction solution was concentrated and mixed with 0.21 g (0.00128×2.0 mol) of methoxylamine hydrochloride and 0.33 g (0.00128× 2.5 mol) of triethyl amine, followed by stirring at room temperature for about one hour. The reaction solution was distributed in ethyl acetate-saturated sodium bicarbonate water, and washed with saturated brine. The organic phase of the solution was dried with anhydrous sodium sulfate, concentrated and purified by silica gel column chromatography (eluting solution: ethyl acetate/hexane), thereby obtaining an aimed product.

Yield by weight: 0.36 g; yield by percentage: 82%; solid; melting point: 91 to 92° C.; $^1$H-NMR (60 MHz, CDCl$_3$, δ): 3.71 (3H, s), 3.83 (3H, s), 6.44 (1H, d, J=2 Hz), 7.0–7.7 (5H, complex), 9.55 (1H, S).

PRODUCTION EXAMPLE 27

Production of N-(n-propoxy)-4-methoxy-6-{3-(trifluoromethyl) phenoxy}-2-pyridine carboxamide (compound No. I-99)

0.6 g (0.0018 mol) of N-hydroxy-4-methoxy-6-{3-(trifluoromethyl)phenoxy)-2-pyridine carboxamide was dissolved in THF, and the obtained solution was mixed with 0.08 g (ca. 60% in mineral oil; 0.0018×1.1 mol) of NaH and then with 0.62 g (0.0018×2.0 mol) of n-propyl iodide, followed by treating the solution under reflux for about 2 hours. The reaction solution was distributed in ethyl acetate-saturated sodium bicarbonate water and then washed with saturated brine. The organic phase of the solution was dried with anhydrous sodium sulfate, concentrated and purified by silica gel column chromatography (eluting solution: ethyl acetate/hexane), thereby obtaining an aimed product.

Yield by weight: 0.40 g; yield by percentage: 59%; solid; melting point: 75 to 77° C.; $^1$H-NMR (60 MHz, CDCl$_3$, δ): 0.89 (3H, t, J=7 Hz), 1.62 (2H, sext., J=7 Hz), 3.82 (2H, t, J=7 Hz), 3.83 (3H, s), 6.46 (1H, d, J=2 Hz), 7.0–7.6 (5H, complex), 9.47 (1H, s).

PRODUCTION EXAMPLE 28

Production of N-(phenylamino)-4-methoxy-6-{3-(trifluoromethyl)phenoxy}-2-pyridine carboxamide (compound No. I-111)

0.4 g (0.00128 mol) of 4-methoxy-6-{3-(trifluoromethyl) phenoxy}-2-pyridine carboxylic acid was mixed with 0.3 g (0.00128×2.0 mol) of thionyl chloride and then with about 10 ml of benzene and a small amount of DMF, followed by treating the obtained mixture under reflux for about 30 minutes. The reaction solution was concentrated and mixed with methylene chloride and then with 0.34 g (0.00128×2.5 mol) of phenyl hydrazine, followed by stirring at room temperature for about one hour. The reaction solution was distributed in ethyl acetate-saturated sodium bicarbonate water, and washed with saturated brine. The organic phase of the solution was dried with anhydrous sodium sulfate, concentrated and purified by silica gel column chromatography (eluting solution: ethyl acetate/hexane), thereby obtaining an aimed product.

Yield by weight: 0.35 g; yield by percentage: 68%; oily substance; $^1$H-NMR (60 MHz, CDCl$_3$, $\delta$): 3.80 (3H, s), 6.12 (1H, brs), 6.3–7.6 (10H, complex), 6.48 (1H, d, J=2 Hz), 8.81 (1H, s).

PRODUCTION EXAMPLE 29

Production of N,N-diethyl-4-methoxy-6-{3-(trifluoromethyl)phenoxy}-2-pyridine carboxamide (compound No. I-200)

0.40 g (0.00128 mol) of 4-methoxy-6-{3-(trifluoromethyl)phenoxy}-2-pyridine carboxylic acid was mixed with 0.3 g (0.00128×2.0 mol) of thionyl chloride and then with about 10 ml of benzene and a small amount of DMF, followed by treating the obtained mixture under reflux for about 30 minutes. The reaction solution was concentrated and mixed with methylene chloride and then with 0.23 g (0.00128×2.5 mol) of diethyl amine, followed by stirring at room temperature for about one hour. The reaction solution was distributed in ethyl acetate-saturated sodium bicarbonate water, and washed with saturated brine. The organic phase of the solution was dried with anhydrous sodium sulfate, concentrated and purified by silica gel column chromatography (eluting solution: ethyl acetate/hexane), thereby obtaining an aimed product.

Yield by weight: 0.44 g; yield by percentage: 91%; solid; melting point: 78 to 89° C.; $^1$H-NMR (60 MHz, CDCl$_3$, $\delta$): 0.81 (3H, t, J=7 Hz), 1.17 (3H, t, J=7 Hz), 3.23 (2H, q, J=7 Hz), 3.47 (2H, q, J=7 Hz), 3.88 (3H, s), 6.47 (1H, d, J=2 Hz), 7.03 (1H, d, J=2 Hz), 7.1–7.6 (4H, complex).

PRODUCTION EXAMPLE 30

Production of N-methyl-N-methylamino-4-methoxy-6-{3-(trifluoromethyl)phenoxy}-2-pyridine carboxamide (compound No. I-202)

0.30 g (0.00096 mol) of 4-methoxy-6-{3-(trifluoromethyl)phenoxy}-2-pyridine carboxylic acid was mixed with 0.23 g (0.00096×2.0 mol) of thionyl chloride and then with about 10 ml of benzene and a small amount of DMF, followed by treating the obtained mixture under reflux for about 30 minutes. The reaction solution was concentrated and mixed with methylene chloride. The resultant solution was dropped into a methylene chloride suspension containing 1.27 g (0.00096×10 mol) of 1,2-dimethyl hydrazine dihydrochloride and 2.03 g (0.0096×21 mol) of triethyl amine, followed by stirring the obtained solution at room temperature for about one hour. The reaction solution was distributed in ethyl acetate-saturated sodium bicarbonate water, and washed with saturated brine. The organic phase of the solution was dried with anhydrous sodium sulfate, concentrated and purified by silica gel column chromatography (eluting solution: ethyl acetate/hexane), thereby obtaining an aimed product.

Yield by weight: 0.18 g; yield by percentage: 53%; oily substance; $^1$H-NMR (60 MHz, CDCl$_3$, $\delta$): 2.15 (1.5H, s), 2.52 (1.5H, s), 3.02 (1.5H, s), 3.05 (1.5H, s), 3.78 (3H, s), 5.4 (1H, brs.), 6.2–6.6 (1H, mult.), 6.8–7.6 (4H, complex).

PRODUCTION EXAMPLE 31

Production of 4-methoxy-2-{N-(2-methylaziridinyl) carbonyl}- 6-{3-(trifluoromethyl)phenoxy}-2-pyridine (compound No. I-300)

0.40 g (0.00128 mol) of 4-methoxy-6-{3-(trifluoromethyl)phenoxy}-2-pyridine carboxylic acid was mixed with 0.3 g (0.00128×2.0 mol) of thionyl chloride and then with about 10 ml of benzene and a small amount of DMF, followed by treating the obtained mixture under reflux for about 30 minutes. The reaction solution was concentrated and mixed with methylene chloride. The obtained solution was dropped into a methylene chloride solution in which 0.73 g (0.00128×10 mol) of propylene imine, followed by stirring the obtained solution at room temperature for about one hour. The reaction solution was distributed in ethyl acetate-saturated sodium bicarbonate water, and washed with saturated brine. The organic phase of the solution was dried with anhydrous sodium sulfate, concentrated and purified by silica gel column chromatography (eluting solution: ethyl acetate/hexane), thereby obtaining an aimed product.

Yield by weight: 0.22 g; yield by percentage: 49%; solid; melting point: 64 to 66° C.; $^1$H-NMR (60 MHz, CDCl$_3$, $\delta$): 0.86 (3H, d, J=5 Hz), 1.85 (1H, d, J=3 Hz), 2.1–2.8 (2H, complex), 3.82 (3H, s), 6.52 (1H, d, J=2 Hz), 7.0–7.7 (5H, complex).

PRODUCTION EXAMPLE 32

Production of 4-methoxy-2-{N-(pyrrolidinyl) carbonyl}-6-{3-(trifluoromethyl)phenoxy}pyridine (compound No. I-302)

0.40 g (0.00128 mol) of 4-methoxy-6-{3-(trifluoromethyl)phenoxy}-2-pyridine carboxylic acid was mixed with 0.3 g (0.00128×2.0 mol) of thionyl chloride and then with about 10 ml of benzene and a small amount of DMF, followed by treating the obtained mixture under reflux for about 30 minutes. The reaction solution was concentrated and mixed with methylene chloride and then with 0.23 g (0.00128×2.5 mol) of pyrrolidine, followed by stirring the obtained solution at room temperature for about one hour. The reaction solution was distributed in ethyl acetate-saturated sodium bicarbonate water, and washed with saturated brine. The organic phase of the solution was dried with anhydrous sodium sulfate, concentrated and purified by silica gel column chromatography (eluting solution: ethyl acetate/hexane), thereby obtaining an aimed product.

Yield by weight: 0.40 g; yield by percentage: 83%; solid; melting point: 102 to 103° C.; $^1$H-NMR (60 MHz, CDCl$_3$, $\delta$): 1.3–2.0 (4H, complex), 3.0–3.8 (4H, complex), 3.84 (3H, s), 6.47 (1H, d, J=2 Hz), 6.9–7.7 (5H, complex).

REFERENCE PRODUCTION EXAMPLE 1

Production of 4-methoxy-6-{3-(trifluoromethyl) phenoxy}-2-pyridine carboxylic acid 3.00 g (0.0086 mol) of 2-bromo-4-methoxy-6-{3-(trifluoromethyl)phenoxy} pyridine was suspended in about 30 ml of diethyl ether. While cooling the obtained suspension in a dry ice-acetone bath in an argon atmosphere, 5.9 ml of a 1.6M-hexane solution of BuLi (0.0086×1.1 mol) was added thereto, followed by stirring the obtained solution for about 10 minutes. After an interior of reactor was replaced with carbon dioxide gas, the reaction solution was removed from the bath and stirred at room temperature for about one hour. The reaction solution was mixed with about 10 ml of a 1N-hydrochloric acid aqueous solution, and then distributed in ethyl acetate-water, followed by washing with saturated sodium bicarbonate water and saturated brine. The organic phase of the obtained solution was dried with anhydrous sodium sulfate, concentrated and purified by silica gel column chromatography (eluting solution: ethyl acetate/hexane), thereby obtaining an aimed product.

Yield by weight: 0.82 g; yield by percentage: 30%; solid; melting point: 85 to 88° C.; $^1$H-NMR (60 MHz, CDCl$_3$, δ): 3.84 (3H, s), 6.55 (1H, d, J=2 Hz), 7.0–7.6 (5H, complex), 9.61 (1H, s).

REFERENCE PRODUCTION EXAMPLE 2

Production of 4-methoxy-6-{3-(trifluoromethyl) phenoxy}-2-pyridine carboxylic acid (1) <Production of 2-chloro-4-nitropyridine N-oxide as an intermediate product>

17.0 g (0.102 mol) of 2-chloropyridine N-oxide hydrochloride was mixed with 64.0 g (0.103×6.4 mol) of sulfuric acid and 36.0 g (0.102 mol) of fuming nitric acid, followed by stirring at 90 to 100° C. for 2.5 hours. The reaction mixture was added to 800 ml of ice water to form a precipitate. The obtained precipitate was filtered out, washed with water and dried. The water phase was extracted with ethyl acetate. The obtained extract was recrystallized with ethyl acetate and hexane.

Yield by weight: 14.4 g; yield by percentage: 82.5%; solid; melting point: 151 to 153° C.; $^1$H-NMR (60 MHz, CDCl$_3$, δ): 7.7–8.2 (1H, mult.), 8.2–8.6 (2H, complex).

(2) <Production of 2-chloro-4-methoxypyridine N-oxide as an intermediate product>

13.4 g (0.077 mol) of 2-chloro-4-nitropyridine N-oxide was suspended in 100 ml of methanol. 14.8 g (ca. 28% methanol solution; 0.077×1.0 mol) of sodium methoxide was dropped into the obtained suspension and dissolved therein by stirring at room temperature, and the solution was further stirred for 2 days. The obtained solution was subjected to distillation under reduced pressure to remove methanol therefrom. The distillation residue was further dissolved in ethyl acetate. The obtained solution was filtered to remove sodium nitrite therefrom, and then ethyl acetate was distilled off, thereby obtaining an aimed product.

Yield by weight: 12.1 g; yield by percentage: 94%; solid; decomposition point: about 90° C.; $^1$H-NMR (60 MHz, CDCl$_3$, δ): 3.80 (3H, s), 6.75 (1H, dd, J=3.5 Hz, 7.5 Hz), 6.99 (1H, d, J=3.5 Hz), 8.21 (1H, d, J=7.5 Hz).

(3) <Production of 2-chloro-6-cyano-4-methoxypyridine as an intermediate product>

8.3 g (0.072×1 mol) of dimethyl sulfate was dropped into 11.1 g (0.070 mol) of 2-chloro-6-cyano-4-methoxypyridine N-oxide. The solution was stirred at room temperature to obtain a homogeneous solution. Thereafter, the obtained homogeneous solution was further stirred overnight. The obtained solution was washed with diethyl ether by decantation, and then dissolved in 70 ml of water. Into the obtained solution was dropped 8.3 g (0.072 mol×4 mol) of sodium cyanide at −10° C. for about one hour. After stirring the reaction solution for 2 hours, the deposited product was filtered out and washed with water. Thus water-washed deposited product was dissolved in ethyl acetate, added with hexane, treated with silica gel and subjected to distillation to remove the solvent therefrom.

Yield by weight: 6.6 g; yield by percentage: 52%; solid; melting point: 94 to 96° C.; $^1$H-NMR (60 MHz, CDCl$_3$, δ): 3.86 (3H, s), 6.94 (1H, d, J=2 Hz), 7.2 (1H, d, J=2 Hz).

(4) <Production of 2-cyano-4-methoxy-6-{3-(trifluoromethyl)phenoxy} pyridine as an intermediate product>

3.74 g (0.0178×1.2 mol) of 3-(trifluoromethyl) phenol was dissolved in about 20 ml of DMF. The obtained solution was further mixed with 0.81 g (ca. 60% in mineral oil; 0.0178×1.1 mol) of NaH and then with 3.0 g (0.0178 mol) of 2-chloro-6-cyano-4-methoxy pyridine, followed by stirring the resultant solution at about 110° C. for about 5 hours. The reaction solution was distributed in hexane-saturated sodium bicarbonate water and then washed with saturated brine. The organic phase of the solution was dried with anhydrous sodium sulfate, concentrated and purified by silica gel column chromatography (eluting solution: ethyl acetate/hexane), thereby obtaining an aimed product.

Yield by weight: 3.74 g; yield by percentage: 71%; solid; melting point: 88 to 90° C.; $^1$H-NMR (60 MHz, CDCl$_3$, δ): 3.85 (3H, s), 6.54 (1H, d, J=2 Hz), 6.94 (1H, d, J=2 Hz), 6.9–7.6 (4H, complex).

(5) <Production of 4-methoxy-6-{3-(trifluoromethyl) phenoxy}picolinic acid>

1.0 g (0.0032 mol) of 2-cyano-4-methoxy-6-(3-(trifluoromethyl)phenoxy} pyridine was suspended in about 10 ml of concentrated hydrochloric acid, followed by stirring the obtained suspension at about 100° C. for about 2 hours. After being allowed to stand for cooling, the reaction solution was mixed with water. The reaction solution was distributed in ethyl acetate-water, followed by washing with saturated brine. Further, the product was dried with anhydrous sodium sulfate, concentrated and purified by silica gel column chromatography, thereby obtaining an aimed product.

Yield by weight: 0.92 g; yield by percentage: 86%.

REFERENCE PRODUCTION EXAMPLE 3

Production of 4-{methyl(phenylmethyl)amino}-6-{3-(trifluoromethyl)phenoxy}-2-pyridine carboxylic acid 2.00 g (0.0046 mol) of 2-bromo-4-{methyl (phenylmethyl)amino}-6-{3-(trifluoromethyl)phenoxy} pyridine was dissolved in about 100 ml of diethyl ether. While cooling the obtained suspension in a dry ice-acetone bath in an argon atmosphere, 2.2 ml of a 1.6M-hexane solution of BuLi (0.0023×1.5 mol) was added thereto, followed by stirring the suspension for about 10 minutes. After an interior of reactor was replaced with carbon dioxide gas, the reaction solution was removed from the bath and stirred at room temperature for about one hour. The reaction solution was mixed with about 10 ml of a 1N-HCl aqueous solution, and then distributed in ethyl acetate-water, followed by washing with saturated brine. The organic phase of the obtained solution was dried with anhydrous sodium sulfate, concentrated and subjected to silica gel column chromatography (eluting solution: ethyl acetate/hexane) to remove a main fraction therefrom. The fraction was concentrated, thereby obtaining an aimed product.

Yield by weight: 0.52 g; yield by percentage: 28%; solid; melting point: 80 to 82° C.; $^1$H-NMR (60 MHz, CDCl$_3$, δ): 3.05 (3H, s), 4.52 (2H, s), 6.18 (1H, d, J=2 Hz), 6.7–7.6 (10H, complex), 9.83 (1H, s).

The compounds shown in the above Tables 1 to 10 were produced according to such methods as described in the above Production Examples 1 to 32. The properties and NMR data of these compounds are shown in Tables 14 to 31 below.

TABLE 14

| Comp. No. | Property | NMR 60 MHz, CDCl$_3$, δ |
|---|---|---|
| I-2 | Solid mp 120–122° C. | 3.77(3H, s), 6.40(1H, d, J = 2 Hz), 6.8–7.6(9H, complex), 9.12(1H, s). |

TABLE 14-continued

| Comp. No. | Property | NMR 60 MHz, CDCl$_3$, δ |
|---|---|---|
| I-5 | Solid mp 110–114° C. | 2.24(3H, s), 3.82(3H, s), 6.45(1H, d, J = 2 Hz), 6.8–7.7(9H, complex), 9.16(1H, s) |
| I-6 | Solid mp 145–146° C. | 2.26(3H, s), 3.82(3H, s), 6.44(1H, d, J = 2 Hz), 6.6–7.6(8H, complex), 7.48(1H, d, J = 2 Hz), 9.13(1H, s). |
| I-8 | Solid mp 148–149° C. | 3.68(3H, s), 3.82(3H, s), 6.45(1H, d, J = 2 Hz), 6.5–7.0(2H, complex), 7.0–7.6(7H, complex), 9.11(1H, s). |
| I-9 | Solid mp 115–116° C. | 2.36(3H, s), 3.77(3H, s), 6.42(1H, d, J = 2 Hz), 7.09(2H, d, J = 8.6 Hz), 7.37(2H, d, J = 8.6 Hz), 7.0–7.6(5H, complex), 9.17(1H, s). |
| I-10 | Solid mp 135–137° C. | 3.85(3H, s), 6.49(1H, d, J = 2 Hz), 7.0–7.9(9H, complex), 9.34(1H, complex). |

TABLE 15

| Comp. No. | Property | NMR 60 MHz, CDCl$_3$, δ |
|---|---|---|
| I-11 | Solid mp 133–135° C. | 3.82(3H, s), 6.44(1H, d, J = 2 Hz), 6.6–7.6 (8H, complex), 7.45(1H, d, J = 2 Hz), 9.14(1H, s). |
| I-14 | Solid mp 135–137° C. | 3.84(3H, s), 6.51(1H, d, J = 2 Hz), 6.5–7.1 (2H, complex), 7.1–7.7(5H, complex), 8.0–8.7(1H, mult.), 9.09(1H, s). |
| I-19 | Solid mp 101–104° C. | 3.72(3H, s), 6.36(1H, d, J = 2 Hz), 6.42(1H, t, J = 73 Hz), 6.6–7.6(10H, complex), 9.22(1H, s). |
| I-21 | Solid mp 81–85° C. | 3.84(3H, s), 6.47(1H, d, J = 2 Hz), 6.8–7.7(10H, complex), 9.22(1H, s). |
| I-25 | Solid mp 160–165° C. | 1.42(3H, t, J = 7 Hz), 4.11(2H, q, J = 7 Hz), 6.46(1H, d, J = 2 Hz), 6.7–7.7(10H, complex), 9.26(1H, s). |

TABLE 16

| Comp. No. | Property | NMR 60 MHz, CDCl$_3$, δ |
|---|---|---|
| I-30 | Solid mp 106–111° C. | 224(3H, s), 3.77(3H, s), 6.40(1H, d, J = 2 Hz), 6.7–7.6(8H, complex), 7.46(1H, d, J = 2 Hz), 9.17(1H, s). |
| I-31 | Solid mp 130–132° C. | 3.87(3H, s), 6.50(1H, d, J = 2 Hz), 7.0–7.9(8H, complex), 7.95(1H, d, J = 2 Hz), 11.3(1H, s). |
| I-32 | Solid mp 103–108° C. | 3.81(3H, s), 6.48(1H, d, J = 2 Hz), 6.8–7.8(9H, complex), 9.23(1H, s). |
| I-34 | Solid mp 91–93° C. | 0.78(3H, t, J = 7 Hz), 1.54(2H, sext, J = 7 Hz), 3.3–4.0(2H, complex), 3.84(3H, s), 6.47(1H, d, J = 2 Hz), 7.0–7.9(4H, complex), 7.92(1H, d, J = 2 Hz), 9.0–9.6(1H, br). |
| I-35 | Solid mp 64–68° C. | 3.2–4.2(4H, complex), 3.83(3H, s), 6.45(1H, d, J = 2 Hz), 7.0–8.0(6H, complex). |
| I-36 | Solid mp 69–72° C. | 0.5–1.8(7H, complex), 2.9–3.6(2H, complex), 3.82(3H, s), 6.41(1H, d, J = 2 Hz), 6.7–7.7(6H. complex). |

TABLE 17

| Comp. No. | Property | NMR 60 MHz, CDCl$_3$, δ |
|---|---|---|
| I-37 | Solid mp 84–88° C. | 1.11(6H, d, J = 6.4 Hz), 3.8–4.5(1H, mult.), 3.84(3H, s), 6.44(1H, d, J = 2 Hz), 6.9–7.7(6H, complex). |
| I-38 | Oily product | 1.12(6H, d, J = 6.4 Hz), 3.7–4.5(1H, mult.), 3.79(3H, s), 6.36(1H, d, J = 2 Hz), 6.43(1H, t, J = 73 Hz), 6.6–7.6(5H, complex), 7.40(1H, d, J = 2 Hz). |
| I-39 | Solid mp 50–54° C. | 1.12(6H, d, J = 6.4 Hz), 3.8–4.5(1H, mult.), 3.83(3H, s), 6.45(1H, d, J = 2 Hz), 6.8–7.7(5H, complex), 7.49(1H, d, J = 2 Hz). |
| I-41 | Solid mp 110–115° C. | 1.29(9H, s), 3.81(3H, s), 6.41(1H, d, J = 2 Hz), 7.0–7.7(6H, complex). |
| I-42 | Oily product | 3.6–4.5(2H, complex), 3.81(3H, s), 4.5–5.4(2H, complex), 5.4–6.2(1H, mult.), 6.46(1H, d, J = 2 Hz), 7.0–7.7(6H, complex). |

TABLE 18

| Comp. No. | Property | NMR 60 MHz, CDCl$_3$, δ |
|---|---|---|
| I-43 | Solid mp 111–115° C. | 0.7–2.3(10H, complex), 3.4–4.3(1H, mult.), 3.82(3H, s), 6.42(1H, d, J = 2 Hz), 7.0–7.8(6H, complex). |
| I-44 | Solid mp 112–116° C. | 1.14(3H, t, J = 7 Hz), 3.3–3.9(2H, complex), 3.85(3H, s), 6.44(1H, d, J = 2 Hz), 6.9–7.8(4H, complex), 7.94(1H, d, J = 2 Hz). 8.9–9.6(1H, br). |
| I-46 | Solid mp 123–125° C. | 2.81(3H, d, J = 5.4 Hz), 3.79(3H, s), 6.38(1H, d, J = 2 Hz), 6.8–7.6(6H, complex). |
| I-47 | Solid mp 124–127° C. | 3.20(3H, d, J = 5 Hz), 3.84(3H, s), 6.42(1H, d, J = 2H 6.8–7.6(4H, complex), 7.94(1H, d, J = 2 Hz), 9.0–9.7(1H, br). |
| I-48 | Solid mp 106–109° C. | 0.1–1.1(4H, complex), 2.4–3.1(1H, mult.), 3.83(3H, s), 6.43(1H, d, J = 2 Hz), 7.0–7.8(6H, complex). |

TABLE 19

| Comp. No. | Property | NMR 60 MHz, CDCl$_3$, δ |
|---|---|---|
| I-49 | Solid mp 102–103° C. | 1.2–2.8(6H, complex), 3.84(3H, s), 3.9–4.8(1H, m), 6.43(1H, d, J = 2 Hz), 6.9–7.8(6H, complex). |
| I-50 | Solid mp 97–99° C. | 0.9–2.3(8H, complex), 3.84(3H, s), 3.9–4.6(1H, m), 6.45(1H, d, J = 2 Hz), 6.9–7.6(6H, complex). |
| I-51 | Solid mp 81–82° C. | 1.10(3H, t, J = 7 Hz), 3.33(2H, quint., J = 7 Hz), 3.86(3H, s), 6.48(1H, d, J = 2 Hz), 7.1–7.8(6H, complex). |
| I-52 | Solid mp 55–56° C. | 0.6–1.8(9H, complex), 3.0–3.5(2H, complex), 3.83(3H, s), 6.46(1H, d, J = 2 Hz), 7.0–7.7(5H, complex), 7.47(1H, d, J = 2 Hz). |
| I-53 | Oily product | 0.5–1.8(11H, complex), 2.9–3.5(2H, complex), 3.85(3H, s), 6.46(1H, d, J = 2 Hz), 6.9–7.7(5H, complex), 7.49(1H, d, J = 2 Hz). |

TABLE 20

| Comp. No. | Property | NMR 60 MHz, CDCl$_3$, δ |
|---|---|---|
| I-54 | Oily product | 0.5–1.9(13H, complex), 3.0–3.5(2H, complex), 3.83(3H, s), 6.44(1H, d, J = 2 Hz), 7.0–7.7(5H, complex), 7.47(1H, d, J = 2 Hz). |
| I-55 | Solid mp | 1.09(6H, d, J = 6.4 Hz), 2.50(3H, s), 3.6–4.4(1H, mult.), 6.78(1H, d, J = 2 Hz), |

TABLE 20-continued

| Comp. No. | Property | NMR 60 MHz, CDCl$_3$, δ |
|---|---|---|
| I-56 | Solid mp 66–69° C. | 6.8–7.7(5H, complex), 7.72(1H, d, J = 2 Hz). 1.09(6H, d, J = 6.4 Hz), 2.79(3H, d, J = 5.6 Hz), 3.5–4.4(1H, mult.), 4.7–5.4(1H, mult.), 5.93(1H, d, J = 2 Hz), 6.8–7.7(6H, complex). |
| I-57 | Solid mp 89–90° C. 108–110° C. | 1.10(6H, d, J = 6.4 Hz), 3.00(6H, s), 3.6–4.4(1H, mult.), 6.06(1H, d, J = 2 Hz), 6.9–7.7(6H, complex). |
| I-58 | Oily product | 1.09(6H, d, J = 6.4 Hz), 3.06(6H, s), 3.6–4.4(1H, mult.), 4.52(2H, s), 6.09(1H, d, J = 2 Hz), 6.8–7.6(11H, complex). |

TABLE 21

| Comp. No | Property | NMR 60 MHz, CDCl$_3$, δ |
|---|---|---|
| I-59 | Solid mp 66–68° C. | 1.11(6H, d, J = 6 Hz), 1.41(3H, t, J = 7 Hz), complex). 3.6–4.5(3H, complex), 6.39(1H, d, J = 2 Hz), 6.7–7.8(6H, complex). |
| I-60 | Solid mp 65–67° C. | 1.42(3H, t, J = 7 Hz), 2.80(2H, d, J = 5 Hz), 4.11(2H, q, J = 7 Hz), 6.45(1H, d, J = 2 Hz), 6.9–7.8(6H complex). |
| I-61 | Solid mp 71–72° C. | 3.22(3H, s), 3.2–3.7(4H, complex), 3.84(3H, s), 6.47(1H, d, J = 2 Hz), 7.0–7.9(6H, complex). |
| I-62 | Solid mp 74–75° C. | 2.0(3H, s), 2.5(2H, t, J = 6.4 Hz), 3.48(2H, q, J = 6.7 Hz), 3.83(3H, s), 6.47(1H, d, J = 2 Hz), 7.0–8.0(6H, complex). |
| I-63 | Solid mp 92–93° C. | 2.81(3H, s), 3.14(2H, t, J = 6.4 Hz), 3.4–4.2(2H, complex), 3.84(3H, s), 6.47(1H, d, J = 2 Hz), 7.0–8.1(6H, complex). |
| I-64 | Solid mp 101–103° C. | 2.09(3H, s), 2.31(2H, t, J = 6 Hz), 3.48(2H, q, J = 6 Hz), 3.84(3H, s), 6.47(1H, d, J = 2 Hz), 7.0–8.0(6H, complex). |

TABLE 22

| Comp. No. | Property | NMR 60 MHz, CDCl$_3$, δ |
|---|---|---|
| I-65 | Solid mp 86–87° C. | 3.1–3.9(4H, complex), 3.85(3H, s), 6.50(1H, d, J = 2 Hz), 7.0–8.0(6H, complex). |
| I-66 | Oily product | 1.05(3H, t, J = 7 Hz), 3.1–3.8(6H, complex), 3.86(3H, s), 6.48(1H, d, J = 2 Hz), 7.0–8.0(5H, complex), 7.49(1H, d, J = 2 Hz). |
| I-67 | Solid mp 77–79° C. | 1.17(3H, t, J = 7 Hz), 2.2–2.8(4H, complex), 3.48(2H, q, J = 6.4 Hz), 3.84(3H, s), 6.49(1H, d, J = 2 Hz), 7.1–8.0(6H, complex). |

TABLE 23

| Comp. No. | Property | NMR 60 MHz, CDCl$_3$, δ |
|---|---|---|
| I-70 | Solid mp 67–69° C. | 2.12(3H, s), 2.58(2H, t, J = 6 Hz), 3.46(2H, q, J = 6 Hz), 3.89(3H, s), 6.42(1H, d, J = 2 Hz), 7.0–8.0(6H, complex). |
| I-71 | Solid mp 75–77° C. | 2.58(2H, t, J = 6.4 Hz), 3.56(2H, q, J = 6.4 Hz), 3.85(3H, s), 6.49(1H, d, J = 2 Hz), 7.1–8.9(6H, complex). |
| I-72 | Solid mp 100–102° C. | 0.81(6H, d, J = 6.4 Hz), 1.3–2.1(1H, mult.), 3.10(2H, t, J =6.4 Hz), 3.86(3H, s), 6.47(1H, d, J = 2 Hz), 6.9–7.7(6H, complex). |
| I-73 | Solid mp 71–73° C. | 0.79(3H, t, J = 6.4 Hz), 1.06(3H, d, J = 6.4 Hz), 1.34(3H, q, J = 6.4 Hz), 3.4–4.2(1H, mult.), 3.83(3H, s), 6.42(1H, d, J = 2 Hz), 6.8–7.6(6H, complex) |

TABLE 23-continued

| Comp. No. | Property | NMR 60 MHz, CDCl$_3$, δ |
|---|---|---|
| I-75 | Oily product | 1.72(2H, quint, J = 7 Hz), 3.1(3H, s), 3.1–3.7(4H, complex), 3.86(3H, s), 6.48(1H, d, J = 2 Hz), 7.0–8.0(5H, complex), 7.51(1H, d, J = 2 Hz). |

TABLE 24

| Comp. No. | Property | NMR 60 MHz, CDCl$_3$, δ |
|---|---|---|
| I-76 | Solid mp 51–53° C. | 1.74(2H, quint, J = 7 Hz), 1.99(3H, s), 2.42(2H, t, J = 7 Hz), 3.40(2H, q, J = 6.4 Hz), 3.84(3H, s), 6.47(1H, d, J = 2 Hz), 7.1–7.7(5H, complex), 7.47(1H, d, J = 2 Hz). |
| I-77 | Solid mp 75–77° C. | 1.6–2.4(2H, complex), 2.85(3H, s), 2.6–3.2(2H, complex), 3.51(2H, q, J = 6.4 Hz), 3.86(3H, s), 6.50(1H, d, J = 2 Hz), 7.0–8.0(6H, complex). |
| I-78 | Solid mp 99–101° C. | 1.6–2.3(2H, complex), 2.50(3H, s), 2.4–2.9(2H, complex), 3.47(2H, q, J = 6.4 Hz), 3.85(3H, s), 6.50(1H, d, J = 2 Hz), 7.0–7.8(6H, complex). |
| I-79 | Solid mp 79–81° C. | 1.6–2.3(2H, complex), 3.1–3.7(4H, complex), 3.87(3H, s), 6.51(1H, d, J = 2 Hz), 7.1–7.8(6H, complex). |
| I-80 | Solid mp 112–113° C. | 3.6–4.5(2H, complex), 3.86(3H, s), 6.54(1H, d, J = 2 Hz), 7.0–8.0(6H, complex). |

TABLE 25

| Comp. No. | Property | NMR 60 MHz, CDCl$_3$, δ |
|---|---|---|
| I-81 | Solid mp 119–121° C. | 3.83(3H, s), 3.5–4.4(2H, complex), 6.49(1H, d, J = 2 Hz), 7.0–7.8(6H, complex). |
| I-82 | Solid mp 83–85° C. | 3.83(3H, s), 3.89(2H, dq, J = 9 Hz, J = 6.4 Hz), 6.47(1H, d, J = 2 Hz), 7.0–7.9(6H, complex). |
| I-84 | Solid mp 115–116° C. | 3.86(3H, s), 4.19(2H, d, J = 6 Hz), 6.52(1H, d, J = 2 Hz), 7.1–8.0(6H, complex). |
| I-85 | Solid mp 80–81° C. | 0.0–1.3(5H, complex), 3.16(2H, t, J = 6 Hz), 3.85(3H, s), 6.48(1H, d, J = 2 Hz), 6.9–7.8(6H, complex). |
| I-89 | Oily product | 2.85(1H, mult.), 3.2–3.9(4H, complex), 3.83(3H, s), 6.43(1H, d, J = 2 Hz), 7.0–8.0(6H, complex). |
| I-90 | Solid mp 82–84° C. | 3.3–4.2(6H, complex), 3.82(3H, s), 4.03(2H, dt, J = 88 Hz, 4 Hz), 6.45(1H, d, J = 2 Hz), 7.0–7.9(6H, complex). |

TABLE 26

| Comp. No. | Property | NMR 60 MHz, CDCl$_3$, δ |
|---|---|---|
| I-93 | Solid mp 83–85° C. | 2.8–4.1(6H, complex), 3.81(3H, s) 4.73(2H, dt, J = 47 Hz, 5 Hz), 6.42(1H, d, J = 2 Hz), 6.8–7.6(5H, complex), 7.84(1H, t, J = 6 Hz). |
| I-94 | Solid mp 76–78° C. | 2.72(2H, t, J = 6 Hz), 3.01(2H, q, J = 9 Hz), 3.48(2H, q, J = 6 Hz), 3.84(3H, s), 6.47(1H, d, J = 2 Hz), 7.0–8.0(6H, complex). |

TABLE 26-continued

| Comp. No. | Property | NMR 60 MHz, CDCl$_3$, δ |
|---|---|---|
| I-95 | Solid mp 112–114° C. | 3.35(2H, t, J = 6 Hz), 3.5–4.2(4H, complex). 3.82(3H, s), 6.45(1H, d, J = 2 Hz), 7.0–7.6(5H, complex), 7.84(1H, t, J = 6 Hz). |

TABLE 27

| Comp. No. | Property | NMR 60 MHz, CDCl$_3$, δ |
|---|---|---|
| I-100 | Solid mp 81–82° C. | 3.85(3H, s), 4.33(2H, d, J = 5 Hz), 4.8–5.4(2H, complex), 5.4–6.4(1H, mult.), 6.47(1H, d, J = 2 Hz), 7.0–7.7(5H, complex), 9.46(1H, s). |
| I-101 | Solid mp 77–79° C. | 2.40(1H, t, J = 2 Hz), 3.84(3H, s), 4.50(2H, d, J = 2 Hz), 6.52(1H, d, J = 2 Hz), 6.9–7.7(5H, complex), 9.72(1H, s). |
| I-102 | Solid mp 64–66° C. | 3.7–4.0(1H, multi.), 3.82(3H, s), 4.0–4.3(1H, multi.), 4.62(2H, dt, J = 36 Hz, 4Hz), 6.43(1H, d, J = 2 Hz), 7.0–7.7(5H, complex), 9.68(1H, s). |
| I-103 | Solid mp 78–81° C. | 2.13(3H, s), 3.82(3H, s), 4.88(2H, s), 6.45(1H, d, J = 2 Hz), 7.0–7.7(5H, complex), 9.72(1H, s). |

TABLE 28

| Comp. No. | Property | NMR 60 MHz, CDCl$_3$, δ |
|---|---|---|
| I-105 | Solid mp 73–75° C. | 1.12(3H, t, J = 7 Hz), 3.62(2H, q, J = 7 Hz), 3.84(3H, s), 4.84(2H, s), 6.48(1H, d, J = 2 Hz), 7.0–7.7(5H, complex), 9.59(1H, s). |
| I-106 | Oily product | 3.76(3H, s), 4.83(2H, s), 6.41(1H, d, J = 2 Hz), 6.8–7.6(10H, complex), 9.44(1H, s). |
| I-107 | Solid mp 80–82° C. | 0.0–1.5(5H, complex), 3.69(2H, d, J = 7 Hz), 3.85(3H, s), 6.47(1H, d, J = 2 Hz), 6.9–7.6(5H, complex), 9.58(1H, s). |
| I-109 | Solid mp 98–99° C. | 2.51(6H, s), 3.85(3H, s), 6.45(1H, d, J = 2 Hz), 6.9–7.6(5H, complex), 7.94(1H, s). |

TABLE 29

| Comp. No. | Property | NMR 60 MHz, CDCl$_3$, δ |
|---|---|---|
| I-113 | Solid mp 62–64° C. | 1.15(6H, d, J = 6.4 Hz), 3.8–4.5(1H, mult.), 3.82(3H, s), 6.34(1H, d, J = 2 Hz), 6.7–7.6(5H, complex), 7.43(1H, d, J = 2 Hz). |
| I-114 | Solid mp 105–106° C. | 0.86(3H, t, J = 7 Hz), 1.68(2H, sext., J = 7 Hz), 3.28(2H, q, J = 6.4 Hz), 3.85(3H, s), 6.42(1H, d, J = 2 Hz), 6.7–7.8(5H, complex), 7.48(1H, d, J = 2 Hz). |
| I-115 | Solid mp 64–65° C. | 1.19(6H, d, J = 6.4 Hz), 2.32(3H, s), 3.7–4.5(1H, mult.), 3.77(3H, s), 6.26(1H, d, J = 2 Hz), 6.7–7.7(5H, complex), 7.39(1H, d, J = 2 Hz). |
| I-116 | Solid mp 81–83° C. | 0.86(3H, t, J = 7 Hz), 1.50(2H, sext., J = 7 Hz), 3.25(2H, q, J = 6.4 Hz), 3.83(3H, s), 6.30(1H, d, J = 2 Hz), 6.6–8.0(5H, complex), 7.40(1H, d, J = 2 Hz). |
| I-117 | Oily product | 1.19(6H, d, J = 6.4 Hz), 3.68(3H, s), 3.75(3H, s), 3.7–4.4(1H, mult.), 6.29(1H, d, J = 2 Hz), 6.4–6.8(3H, complex), 7.0–7.7(2H, complex), 7.37(1H, d, J = 2 Hz). |

TABLE 30

| Comp. No. | Property | NMR 60 MHz, CDCl$_3$, δ |
|---|---|---|
| I-118 | Oily product | 0.86(3H, t, J = 7 Hz), 1.50(2H, sext., J = 7 Hz), 3.25(2H, q, J = 6.4 Hz), 3.69(3H, s), 3.78(3H, s), 6.32(1H, d, J = 2 Hz), 6.4–6.9(3H, complex), 6.9–7.9(2H, complex), 7.41(1H, d, J = 2 Hz). |
| I-126 | Solid mp 98–99° C. | 1.01(9H, s), 3.83(3H, s), 4.5(1H, brs), 6.48(1H, d, J = 2 Hz), 7.0–7.6(5H, complex), 8.40(1H, s). |
| I-127 | Solid mp 92–93° C. | 2.82(3H, s), 3.85(3H, s), 4.58(2H, d, J = 7 Hz), 6.50(1H, d, J = 2 Hz), 6.7–7.7(5H, complex), 8.28(1H, t, J = 7 Hz). |
| I-201 | Solid mp 57–61° C. | 0.77(2H, t, J = 7 Hz), 1.10(1H, t, J = 7 Hz), 2.81(1H, s), 2.89(2H, s), 2.9–3.7(2H, complex), 3.82(3H, s), 6.3–6.7(1H, multi.), |
| I-203 | Oily product | 3.17(3H, s), 3.40(3H, s), 3.81(3H, s), 6.46(1H, d, J = 2 Hz), 6.99(1H, d, J = 2 Hz), 7.0–7.6(5H, complex). |

TABLE 31

| Comp. No. | Property | NMR 60 MHz, CDCl$_3$, δ |
|---|---|---|
| I-303 | Solid mp 112–113° C. | 2.9–3.8(8H, complex), 3.80(3H, s), 6.41(1H, d, J = 2 Hz), 6.99(1H, d, J = 2 Hz), 6.9–7.6(5H, complex). |
| I-304 | Oily product | 1.7–2.6(4H, complex), 2.16(3H, s), 3.1–3.9(4H, complex), 3.83(3H, s), 6.42(1H, d, J = 2 Hz), 6.96(1H, d, J = 2 Hz), 6.9–7.6(5H, complex). |

Next, Formulation Examples and Experimental Examples are shown below. However, as readily understood by those skilled in the art, carriers (diluents), auxiliaries or adjuvants, effective ingredients and mixing ratios therebetween shown in these Examples can be varied over a wide range without departing from the sprits of the present invention.

"Part" in respective Formulation Examples represents "part by weight".

| Formulation Example 1: (water-dispersible powder) | |
|---|---|
| Compound No. (I-33) | 50 parts |
| Sodium lignosulfonate | 5 parts |
| Sodium alkyl-sulfonate | 3 parts |
| Diatomaceous earth | 42 parts |

The above-mentioned components were mixed and pulverized together to prepare a water-dispersible powder. The thus prepared powder was diluted with water upon use.

| Formulation Example 2: (emulsion) | |
|---|---|
| Compound No. (I-37) | 25 parts |
| Xylene | 65 parts |
| Polyoxyethylene alkylaryl ether | 10 parts |

The above-mentioned components were homogeneously mixed together to prepare an emulsion. The thus prepared emulsion was diluted with water upon use.

| Formulation Example 3: (granules) | |
| --- | --- |
| Compound No. (I-48) | 8 parts |
| Bentonite | 40 parts |
| Clay | 45 parts |
| Calcium lignosulfonate | 7 parts |

The above-mentioned components were homogeneously mixed together. The obtained mixture was further kneaded while adding water thereto, and then extruded into granules by using an extrusion-type granulator.

EXPERIMENTAL EXAMPLE 1

Experiment for Determination of Herbicidal Effect by Foliate and Soil Treatment (1) <Preparation for plants to be tested>

Seeds of redroot pigweed (*Amaranthus retroflexus*), common blackjack (*Bidens pilosa*), kediock (*Sinapis arvensis*), common chickweed (*Stellaria media*), sicklepod (*Cassia obtusifolia*), black nightshade (*Solanum nigrum*), velvetleaf (*Abutilon theophrasti*), field bindweed (*Convolvulus arvensis*), wild chamomile (*Matricaria chamomilla*), cleavers (*Galium aparine*) and ivyleafspeedwell (*Veronica hederaefolia*), were uniformly sowed over a horticultural granular soil (produced by KUREHA CHEMICAL INDUSTRY, CO., LTD.; the same soil was used hereinafter) filled in a planter. The planter was placed in a greenhouse (maintained at 19 to 25° C.) to sprout these plants. Two seedlings of each sprouted plant were transplanted to a 10 cm-diameter pot filled with the horticultural granular soil and cultivated in the greenhouse (maintained at 19 to 25° C.) until reaching a cotyledonal to bifoliate period suited to the foliage and soil treatment.

(2) <Preparation and spray of a solution to be tested>

Each compound to be tested was dissolved or suspended in an aqueous solution containing 10% (v/v) of acetone and 0.5% (v/v) of Tween 20 such that the concentration of the compound was 1 mg/ml. Next, additional amounts of Tween 20 and water were added to the obtained solution or suspension to produce a test solution. The plants prepared in the above (1) were placed within a frame having a predetermined inside area, and uniformly sprayed with the test solution using a sprayer such that the amount of each compound applied was controlled to a predetermined level.

(3) <Evaluation for herbicidal effect of test compound>

The plants sprayed with the test solution were placed again in the greenhouse (maintained at 19 to 25° C.) and cultivated therein. After 14 days, the degree of growth of each plant cultivated in the treated region was compared with that of plant cultivated in non-treated region, and evaluated according to the following ratings. The herbicidal activity of each test compound was represented by these ratings Examination Ratings:

1: percentage of weeds killed was less than 20%;

2: percentage of weeds killed was not less than 20% and less than 40%;

3: percentage of weeds killed was not less than 40% and less than 60%;

4: percentage of weeds killed was not less than 60% and less than 80%;

5: percentage of weeds killed was not less than 80%;

The evaluation results are shown in Tables 32 to 37.

TABLE 32

| Compound | | Weed a) | | | | | | | | | |
| --- | --- | --- | --- | --- | --- | --- | --- | --- | --- | --- | --- |
| No. | g ai/10a | AR | BP | SA | SM | CO | SN | AT | CA | MC | GA | VH |
| control (a) | 10 | 3 | 1 | 3 | 1 | 1 | 4 | 2 | 2 | 1 | 2 | 3 |
|  | 25 | 3 | 1 | 4 | 1 | 2 | 4 | 3 | 3 | 1 | 3 | 4 |
|  | 62.5 | 4 | 1 | 5 | 1 | 3 | 5 | 3 | 3 | 1 | 4 | 5 |
| I-37 | 10 | 5 | 5 | 5 | 5 | 5 | 5 | 4 | 5 | 5 | 5 | 5 |
| I-55 | 10 | 5 | 4 | 4 | 4 | 5 | 5 | 4 | 4 | 3 | 5 | 5 |
| I-56 | 10 | 5 | 4 | 5 | 4 | 4 | 5 | 5 | 5 | 4 | 5 | 5 |
| I-57 | 10 | 5 | 5 | 5 | 4 | 5 | 5 | 4 | 4 | 3 | 5 | 5 |

Test compound (a): N-(i-propyl)-6-{3-(trifluoromethyl)phenoxy}-2-pyridine carboxamide;

Compound (I-37): N-(i-propyl)-4-methoxy-6-{3-(trifluoromethyl)phenoxy}-2-pyridine carboxamide;

Compound (I-55): N-(i-propyl)-4-methylmercapto-6-{3-(trifluoromethyl)phenoxy}-2-pyridine carboxamide;

Compound (I-56): N-(i-propyl)-4-methylamino-6-{3-(trifluoromethyl)phenoxy}-2-pyridine carboxamide;

Compound (I-57): N-(i-propyl)-4-dimethylamino-6-{3-(trifluoromethyl)phenoxy}-2-pyridine carboxamide;

TABLE 33

| Compound | | Weed a) | | | | | | | | | |
| --- | --- | --- | --- | --- | --- | --- | --- | --- | --- | --- | --- |
| No. | g ai/10a | AR | BP | SA | SM | CO | SN | AT | CA | MC | GA | VH |
| control (b) | 10 | 5 | 1 | 5 | 4 | 3 | 5 | 3 | 2 | 1 | 5 | 5 |
| control (c) | 10 | 5 | 1 | 5 | 3 | 2 | 4 | 3 | 2 | 1 | 4 | 5 |
| I-33 | 10 | 5 | 5 | 5 | 5 | 5 | 5 | 5 | 4 | 5 | 5 | 5 |
| I-34 | 10 | 5 | 5 | 5 | 5 | 5 | 5 | 5 | 4 | 5 | 5 | 5 |

Test compound (b): N-(n-propyl)-6-{3-(trifluoromethyl)phenoxy}-2-pyridine carboxamide;

Test compound (c): N-(n-propyl)-6-{3-(trifluoromethyl)phenoxy}-2-pyridine thiocarboxamide;

Compound (I-33): N-(n-propyl)-4-methoxy-6-{3-(trifluoromethyl)phenoxy}-2-pyridine carboxamide;

Compound (I-34): N-(n-propyl)-4-methoxy-6-{3-(trifluoromethyl)phenoxy}-2-pyridine thiocarboxamide;

TABLE 34

| Comp. No. | g ai/10a | Weed a) | | | | | | | | | | |
|---|---|---|---|---|---|---|---|---|---|---|---|---|
| | | AR | BP | SA | SM | CO | SN | AT | CA | MC | GA | VH |
| I-1 | 10 | 5 | 5 | 5 | 4 | 5 | 5 | 4 | 4 | 4 | 5 | 5 |
| I-2 | 10 | 5 | 5 | 5 | 4 | 5 | 5 | 4 | 5 | 3 | 5 | 5 |
| I-11 | 10 | 5 | 5 | 5 | 4 | 5 | 5 | 3 | 4 | 4 | 5 | 5 |
| I-20 | 10 | 5 | 5 | 5 | 5 | 5 | 5 | 4 | 4 | 4 | 5 | 5 |
| I-35 | 10 | 5 | 5 | 5 | 5 | 5 | 5 | 5 | 5 | 5 | 5 | 5 |
| I-36 | 10 | 5 | 5 | 5 | 5 | 5 | 5 | 4 | 5 | 5 | 5 | 5 |
| I-38 | 10 | 5 | 2 | 5 | 4 | 4 | 5 | 4 | 4 | 4 | 5 | 5 |
| I-39 | 10 | 5 | 3 | 5 | 5 | 5 | 5 | 5 | 5 | 4 | 5 | 5 |
| I-40 | 10 | 5 | 4 | 5 | 5 | 5 | 5 | 5 | 5 | 4 | 5 | 5 |
| I-42 | 10 | 5 | 3 | 5 | 5 | 5 | 5 | 4 | 4 | 4 | 5 | 5 |
| I-43 | 10 | 5 | 4 | 5 | 5 | 5 | 5 | 4 | 5 | 4 | 5 | 5 |
| I-44 | 10 | 5 | 4 | 5 | 5 | 5 | 5 | 4 | 4 | 3 | 5 | 5 |
| I-45 | 10 | 5 | 5 | 5 | 5 | 5 | 5 | 4 | 5 | 2 | 5 | 5 |
| I-46 | 10 | 5 | 3 | 5 | 5 | 5 | 5 | 4 | 5 | 3 | 5 | 5 |
| I-47 | 10 | 5 | 3 | 5 | 4 | 5 | 5 | 5 | 5 | 3 | 5 | 5 |
| I-48 | 10 | 5 | 4 | 5 | 5 | 5 | 5 | 5 | 5 | 5 | 5 | 5 |
| I-49 | 10 | 5 | 5 | 5 | 5 | 5 | 5 | 5 | 5 | 5 | 5 | 5 |

TABLE 35

| Comp. No. | g ai/10a | Weed a) | | | | | | | | | | |
|---|---|---|---|---|---|---|---|---|---|---|---|---|
| | | AR | BP | SA | SM | CO | SN | AT | CA | MC | GA | VH |
| I-50 | 10 | 5 | 5 | 5 | 5 | 4 | 5 | 4 | 5 | 5 | 5 | 5 |
| I-51 | 10 | 5 | 3 | 5 | 5 | 5 | 5 | 5 | 4 | 4 | 5 | 5 |
| I-52 | 10 | 5 | 3 | 5 | 5 | 4 | 5 | 4 | 5 | 3 | 5 | 5 |
| I-58 | 10 | 5 | 2 | 5 | 4 | 5 | 5 | 4 | 5 | 3 | 5 | 5 |
| I-59 | 10 | 5 | 3 | 5 | 5 | 5 | 5 | 4 | 4 | 4 | 5 | 5 |
| I-61 | 10 | 5 | 2 | 5 | 5 | 5 | 5 | 4 | 3 | 5 | 5 | 5 |
| I-62 | 10 | 5 | 4 | 5 | 5 | 5 | 5 | 3 | 4 | 4 | 5 | 5 |
| I-63 | 10 | 5 | 4 | 5 | 5 | 5 | 5 | 4 | 5 | 4 | 5 | 5 |
| I-67 | 10 | 5 | 3 | 5 | 4 | 5 | 5 | 4 | 5 | 3 | 5 | 5 |
| I-68 | 10 | 5 | 4 | 5 | 4 | 5 | 5 | 5 | 4 | 2 | 5 | 5 |
| I-69 | 10 | 5 | 3 | 5 | 4 | 5 | 5 | 5 | 4 | 3 | 5 | 5 |
| I-71 | 10 | 5 | 5 | 5 | 5 | 5 | 5 | 4 | 5 | 4 | 5 | 5 |
| I-72 | 10 | 5 | 5 | 5 | 5 | 5 | 5 | 4 | 5 | 5 | 5 | 5 |
| I-73 | 10 | 5 | 4 | 5 | 5 | 5 | 5 | 5 | 5 | 4 | 5 | 5 |
| I-74 | 10 | 5 | 5 | 5 | 5 | 5 | 5 | 5 | 5 | 5 | 5 | 5 |
| I-75 | 10 | 5 | 3 | 5 | 5 | 5 | 5 | 3 | 4 | 4 | 5 | 5 |
| I-76 | 10 | 5 | 4 | 5 | 4 | 5 | 5 | 3 | 3 | 5 | 5 | 5 |
| I-77 | 10 | 5 | 4 | 5 | 4 | 5 | 5 | 5 | 4 | 3 | 5 | 5 |
| I-79 | 10 | 5 | 5 | 5 | 5 | 5 | 5 | 5 | 4 | 5 | 5 | 5 |
| I-80 | 10 | 5 | 5 | 5 | 5 | 5 | 5 | 5 | 5 | 5 | 5 | 5 |

TABLE 36

| Comp. No. | g ai/10a | Weed a) | | | | | | | | | | |
|---|---|---|---|---|---|---|---|---|---|---|---|---|
| | | AR | BP | SA | SM | CO | SN | AT | CA | MC | GA | VH |
| I-81 | 10 | 5 | 5 | 5 | 5 | 5 | 5 | 5 | 5 | 5 | 5 | 5 |
| I-82 | 10 | 5 | 4 | 5 | 5 | 5 | 5 | 5 | 5 | 5 | 5 | 5 |
| I-83 | 10 | 5 | 5 | 5 | 5 | 5 | 5 | 5 | 5 | 5 | 5 | 5 |

TABLE 36-continued

| Comp. No. | g ai/10a | AR | BP | SA | SM | CO | SN | AT | CA | MC | GA | VH |
|---|---|---|---|---|---|---|---|---|---|---|---|---|
| I-84 | 10 | 5 | 5 | 5 | 4 | 5 | 5 | 5 | 4 | 2 | 5 | 5 |
| I-85 | 10 | 5 | 4 | 5 | 5 | 5 | 5 | 5 | 4 | 5 | 5 | 5 |
| I-86 | 10 | 5 | 4 | 5 | 5 | 4 | 5 | 5 | 3 | 4 | 5 | 5 |
| I-87 | 10 | 5 | 5 | 5 | 5 | 5 | 5 | 5 | 5 | 5 | 5 | 5 |
| I-88 | 10 | 5 | 3 | 5 | 5 | 5 | 5 | 5 | 5 | 2 | 5 | 5 |
| I-89 | 10 | 5 | 5 | 5 | 5 | 5 | 5 | 4 | 4 | 3 | 5 | 5 |
| I-90 | 10 | 5 | 5 | 5 | 5 | 5 | 5 | 3 | 4 | 2 | 5 | 5 |
| I-92 | 10 | 5 | 4 | 5 | 4 | 5 | 5 | 3 | 4 | 3 | 5 | 5 |
| I-94 | 10 | 5 | 4 | 5 | 4 | 5 | 5 | 5 | 5 | 4 | 5 | 5 |

TABLE 37

| Comp. No. | g ai/10a | AR | BP | SA | SM | CO | SN | AT | CA | MC | GA | VH |
|---|---|---|---|---|---|---|---|---|---|---|---|---|
| I-96 | 10 | 5 | 4 | 5 | 5 | 5 | 5 | 3 | 3 | 1 | 5 | 5 |
| I-97 | 10 | 5 | 5 | 5 | 5 | 5 | 5 | 5 | 4 | 5 | 5 | 5 |
| I-99 | 10 | 5 | 5 | 5 | 5 | 5 | 5 | 5 | 5 | 4 | 5 | 5 |
| I-100 | 10 | 5 | 4 | 5 | 4 | 5 | 5 | 5 | 4 | 4 | 5 | 5 |
| I-102 | 10 | 5 | 5 | 5 | 4 | 5 | 5 | 4 | 4 | 3 | 5 | 5 |
| I-105 | 10 | 5 | 4 | 5 | 4 | 5 | 5 | 4 | 4 | 3 | 5 | 5 |
| I-107 | 10 | 5 | 3 | 5 | 5 | 5 | 5 | 4 | 4 | 3 | 5 | 5 |
| I-109 | 10 | 5 | 5 | 5 | 4 | 5 | 5 | 5 | 4 | 4 | 5 | 5 |
| I-123 | 10 | 5 | 2 | 5 | 5 | 2 | 5 | 3 | 4 | 1 | 5 | 5 |
| I-126 | 10 | 5 | 5 | 5 | 5 | 5 | 5 | 5 | 4 | 4 | 5 | 5 |
| I-127 | 10 | 5 | 5 | 5 | 5 | 5 | 5 | 5 | 5 | 4 | 5 | 5 |
| I-200 | 10 | 5 | 2 | 5 | 5 | 5 | 5 | 5 | 5 | 4 | 5 | 5 |
| I-201 | 10 | 5 | 2 | 5 | 5 | 5 | 5 | 4 | 5 | 2 | 5 | 5 |
| I-202 | 10 | 5 | 4 | 5 | 5 | 5 | 5 | 4 | 4 | 3 | 5 | 5 |
| I-203 | 10 | 5 | 3 | 5 | 4 | 5 | 5 | 4 | 4 | 2 | 5 | 5 |
| I-300 | 10 | 5 | 5 | 5 | 5 | 5 | 5 | 4 | 4 | 2 | 5 | 5 |
| I-302 | 10 | 5 | 2 | 5 | 5 | 5 | 5 | 4 | 4 | 4 | 5 | 5 |

Kinds of weeds a)

AR: *Amaranthus retroflexus*, BP: *Bidens pilosa*, SA: *Sinapis arvensis*, SM: *Stellaria media*, CO: *Cassia obtusifolia*, SN: *Solanum nigrum*, AT: *Abutilon theophrasti*, CA: *Convolvulus arvensis*, MC: *Matricaria chamomilla*, GA: *Galium aparine* and VH: *Veronica hederaefolia*

INDUSTRIAL APPLICABILITY

As described above, the above-mentioned N-(substituted or unsubstituted)-4-substituted-6-(substituted or unsubstituted) phenoxy-2-pyridine carboxamide or thiocarboxamide represented by the general formula (I) according to the present invention, is a novel compound and can be used as an effective ingredient of a herbicide.

What is claimed is:

1. N-(substituted or unsubstituted)-4-substituted-6-(substituted or unsubstituted) phenoxy-2-pyridine carboxamide or thiocarboxamide represented by the formula (I):

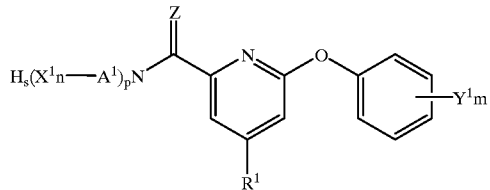

(I)

wherein $R^1$ is a $C_1$ to $C_4$ alkoxy group or a $C_1$ to $C_4$ alkylthio group;

$A^1$ is optionally substituted with $X^1$, and is a $C_1$ to $C_{10}$ alkyl group, a $C_2$ to $C_6$ alkenyl group, a $C_3$ to $C_6$ alkynyl group, a $C_3$ to $C_6$ cycloalkyl group, a $C_1$ to $C_{10}$ alkoxy group, a $C_3$ to $C_6$ alkenyloxy group, a $C_3$ to $C_6$ alkynyloxy group, a $C_1$ to $C_{10}$ alkylamino group, a di($C_1$ to $C_6$ alkyl)amino group, a phenyl group, a phenylamino group, an arylalkyl group whose alkyl moiety has 1 to 3 carbon atoms, an arylalkyloxy group whose alkyl moiety has 1 to 3 carbon atoms, an arylalkylamino group whose alkyl moiety has 1 to 3 carbon atoms, an amino group or a hydroxyl group wherein the chain-like hydrocarbon moiety of $A^1$ is constituted by a longest carbon chain as a main chain exclusive of a $C_1$ to $C_4$ alkyl group bonded as side chain to said main chain, and said $C_1$ to $C_4$ alkyl group as side chain is regarded as $X^1$;

$X^1$ is a halogen atom, a $C_1$ to $C_4$ alkoxy group, a $C_1$ to $C_4$ alkylthio group, a $C_1$ to $C_4$ alkyl group which is not bonded to a terminal position of $A^1$ when $A^1$ is a $C_1$ to $C_{10}$ alkyl group, a $C_1$ to $C_{10}$ alkoxy group, a $C_1$ to $C_{10}$ alkylamino group or a di($C_1$ to $C_6$ alkyl)amino group, a $C_3$ to $C_6$ cycloalkyl group, a $C_1$ to $C_4$ alkylcarbonyl group, a $C_1$ to $C_4$ alkylamino group, a di($C_1$ to $C_4$ alkyl)amino group, a $C_1$ to $C_4$ alkylsulfonyl group, a $C_1$ to $C_4$ alkylsulfinyl group, a hydroxyl group, an amino group, a cyano group or a thiol group, wherein the alkyl moiety of $X^1$ is optionally substituted with halogen atom(s);

n is 0 or an integer selected from numbers of hydrogen atoms of $A^1$ which can be substituted with $X^1$, and when n is an integer of not less than 2, $X^1$s may be the same or different;

p and s are an integer of 0 to 2 with the proviso that the sum of p and s is 2;

when p is 2, $A^1$ may be the same or different;

when p is 2 and two $A^1$s are alkyl chains, the $A^1$s may be directly bonded together to form a ring, or the $A^1$s may be bonded to each other through an oxygen atom of the hydroxyl group, or a nitrogen atom of the amino group or the $C_1$ to $C_4$ alkylamino group which groups are bonded to one of the $A^1$s, to form a ring;

$Y^1$ is a $C_1$ to $C_4$ haloalkyl group, a $C_1$ to $C_4$ alkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom;

m is a n integer of 0 to 5, and when m is not less than 2, $Y^1$s may be the same or different; and Z is an oxygen atom or a sulfur atom.

2. A compound according to claim 1, wherein $R^1$ is a methoxy group, a methylthio group, a dimethylamino group or a methylamino group.

3. A compound according to claim 1 or claim 2, wherein $Y^1$ is bonded to the 3-position of the benzene ring, and is a trifluoromethyl group, a difluoromethoxy group, a trifluoromethoxy group or a trifluoromethylthio group.

4. A process for producing N-(substituted or unsubstituted)-4-substituted-6-(substituted or unsubstituted) phenoxy-2-pyridine carboxamide or thiocarboxamide as defined in claim 1, comprising:

reacting a compound represented by the formula (IV) with (substituted or unsubstituted) amine, (substituted or unsubstituted) hydroxyl amine or (substituted or unsubstituted) hydrazine represented by the formula (V) to produce N-(substituted or unsubstituted)-4-substituted-6-(substituted or unsubstituted) phenoxy-2-pyridine carboxamide or thiocarboxamide represented by the formula (I-b),

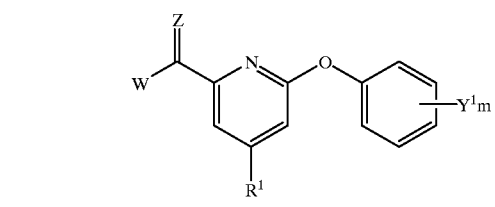

(IV)

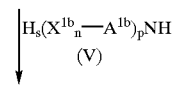

(V)

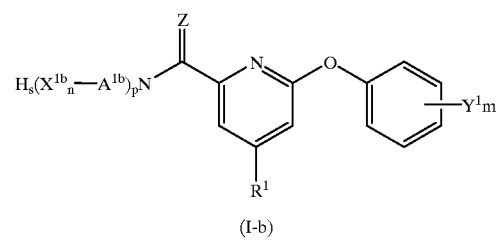

(I-b)

wherein $R^1$ is a $C_1$ to $C_4$ alkoxy group, a $C_1$ to $C_4$ alkylthio group, a $C_1$ to $C_4$ alkylamino group, a di($C_1$ to $C_4$ alkyl)amino group or a ($C_1$ to $C_4$ alkyl)($C_7$ to $C_8$ aralkyl)amino group;

$A^{1b}$ may be substituted with $X^{1b}$, and is a $C_1$ to $C_{10}$ alkyl group, a $C_2$ to $C_6$ alkenyl group, a $C_3$ to $C_6$ alkynyl group, a $C_3$ to $C_6$ cycloalkyl group, a $C_1$ to $C_{10}$ alkoxy group, a $C_3$ to $C_6$ alkenyloxy group, a $C_3$ to $C_6$ alkynyloxy group, a $C_1$ to $C_{10}$ alkylamino group, a di($C_1$ to $C_6$ alkyl)amino group, a phenyl group, a phenylamino group, an arylalkyl group whose alkyl moiety has 1 to 3 carbon atoms, an arylalkyloxy group whose alkyl moiety has 1 to 3 carbon atom, an arylalkylamino group whose alkyl moiety has 1 to 3 carbon atoms, an amino group or a hydroxyl group wherein the chain-like hydrocarbon moiety of $A^{1b}$ is constituted by a longest carbon chain as a main chain exclusive of a $C_1$ to $C_4$ alkyl group bonded as side chain to said main chain, and said $C_1$ to $C_4$ alkyl group as side chain is regarded as $X^{1b}$;

$X^{1b}$ is a halogen atom, a $C_1$ to $C_4$ alkoxy group, a $C_1$ to $C_4$ alkylthio group, a $C_1$ to $C_4$ alkyl group which is not bonded to a terminal position of $A^{1b}$ when $A^{1b}$ is a $C_1$ to $C_{10}$ alkyl group, a $C_1$ to $C_{10}$ alkoxy group, a $C_1$ to $C_{10}$ alkylamino group or a di($C_1$ to $C_6$ alkyl)amino group, a $C_3$ to $C_6$ cycloalkyl group, a $C_1$ to $C_4$ alkylcarbonyl group, a $C_1$ to $C_4$ alkylamino group, a di($C_1$ to $C_4$ alkyl)amino group, a $C_1$ to $C_4$ alkylsulfonyl group, a $C_1$ to $C_4$ alkylsulfinyl group, a hydroxyl group, an amino group, a cyano group or a thiol group, wherein the alkyl moiety of $X^{1b}$ may be substituted with halogen atom(s);

n is 0 or an integer selected from numbers of hydrogen atoms of $A^{1b}$ which can be substituted with $X^{1b}$, and when n is an integer of not less than 2, $X^{1b}$s may be the same or different;

p and s are an integer of 0 to 2 with the proviso that the sum of p and s is 2;

when p is 2, $A^{1b}$ may be the same or different;

when p is 2 and the $A^{1b}$s are alkyl chains, the $A^{1b}$s may be directly bonded together to from a ring, or the $A^{1b}$s may be bonded to each other through an oxygen atom of the hydroxyl group or a nitrogen atom of the amino group or the $C_1$ to $C_4$ alkylamino group which groups are bonded to one of the $A^{1b}$s, to form a ring;

$Y^1$ is a $C_1$ to $C_4$ haloalkyl group, a $C_1$ to $C_4$ alkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom;

m is an integer of 0 to 5, and when m is not less than 2, $Y^1$s may be the same or different;

Z is an oxygen atom or a sulfur atom; and

W is a leaving group.

5. A process for producing N-substituted-4-substituted-6-(substituted or unsubstituted) phenoxy-2-pyridine carboxamide or thiocarboxamide as defined in claim 1 comprising:

reacting N-(substituted or unsubstituted)-4-substituted-6-(substituted or unsubstituted) phenoxy-2-pyridine carboxamide represented by the formula (VI) with a compound represented by the formula (VII-a) to produce N-substituted-4-substituted-6-(substituted or unsubstituted) phenoxy-2-pyridine carboxamide or thiocarboxamide represented by the formula (I-c),

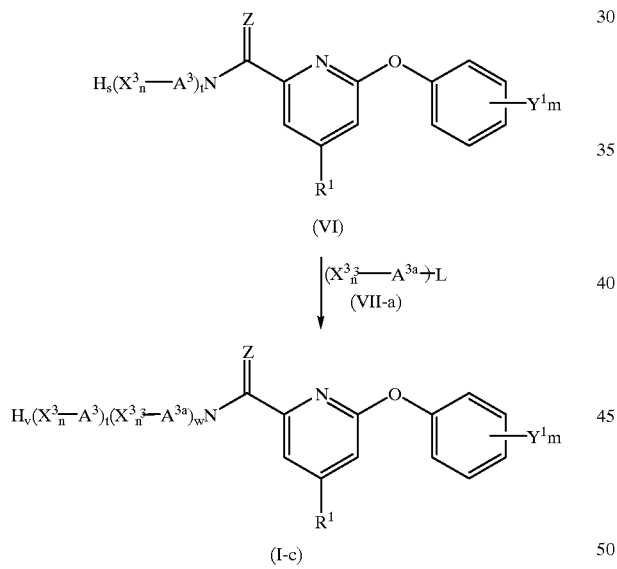

wherein $R^1$ is a $C_1$ to $C_4$ alkoxy group, a $C_1$ to $C_4$ alkylthio group, a $C_1$ to $C_4$ alkylamino group, a di($C_1$ to $C_4$ alkyl)amino group or a ($C_1$ to $C_4$ alkyl)($C_7$ to $C_8$ aralkyl)amino group;

$A^3$ may be substituted with $X^3$, and is a $C_1$ to $C_{10}$ alkyl group, a $C_3$ to $C_6$ alkenyl group, a $C_3$ to $C_6$ alkynyl group, a $C_3$ to $C_6$ cycloalkyl group, a $C_1$ to $C_{10}$ alkoxy group, a $C_3$ to $C_6$ alkenyloxy group, a $C_3$ to $C_6$ alkynyloxy group, a di($C_1$ to $C_6$ alkyl)amino group, a phenyl group, an aralkyl group whose alkyl moiety has 1 to 3 carbon atoms or an arylalkyloxy group whose alkyl moiety has 1 to 3 carbon atoms wherein the chain-like hydrocarbon moiety of $A^3$ is constituted by a longest carbon chain as a main chain exclusive of a $C_1$ to $C_4$ alkyl group bonded as side chain to said main chain, and said $C_1$ to $C_4$ alkyl group as side chain is regarded as $X^3$;

$A^{3a}$ may be substituted with $X^3$, and is a $C_1$ to $C_{10}$ alkyl group, a $C_3$ to $C_6$ alkenyl group, a $C_3$ to $C_6$ alkynyl group, a $C_3$ to $C_6$ cycloalkyl group or an arylalkyl group whose alkyl moiety has 1 to 3 carbon atoms, wherein the chain-like hydrocarbon moiety of $A^{3a}$ is constituted by a longest carbon chain as a main chain exclusive of side chains bonded to the main chain, and the side chains are regarded as $X^3$;

$X^3$ is a halogen atom, a $C_1$ to $C_4$ alkoxy group, a $C_1$ to $C_4$ alkylthio group, a $C_1$ to $C_4$ alkyl group which is not bonded to terminal positions of $A^3$ and $A^{3a}$ when $A^3$ and $A^{3a}$ are a $C_1$ to $C_{10}$ alkyl group, a $C_1$ to $C_{10}$ alkoxy group or a di($C_1$ to $C_6$ alkyl)amino group, a $C_3$ to $C_6$ cycloalkyl group, a $C_1$ to $C_4$ alkylamino group, a di($C_1$ to $C_4$ alkyl)amino group, a $C_1$ to $C_4$ alkylsulfonyl group, a $C_1$ to $C_4$ alkylsulfinyl group or a cyano group, wherein the alkyl moiety of $X^3$ may be substituted with halogen atom(s);

n and $n^3$ are 0 or an integer selected from numbers of hydrogen atoms of $A^3$ and $A^{3a}$, respectively, which can be substituted with $X^3$, and when n and $n^3$ are an integer of not less than 2, $X^3$s may be the same or different;

v is 0 or 1, t is 0 or 1, and w is 1 or 2 with the proviso that the sum of t and v, is 0 or 1 and the sum of t, v, and w is 2;

when w is 2, $A^{3a}$s may be the same or different;

$Y^1$ is a $C_1$ to $C_4$ haloalkyl group, a $C_1$ to $C_4$ alkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom;

m is an integer of 0 to 5, and when m is not less than 2, $Y^1$s may be the same or different;

Z is an oxygen atom or a sulfur atom; and

L is a leaving group.

6. A process for producing N-(substituted-4-substituted)-6-(substituted or unsubstituted) phenoxy-2-pyridine carboxamide or thiocarboxamide as defined in claim 1 comprising:

reacting N-substituted-4-substituted-6-(substituted or unsubstituted) phenoxy-2-pyridine carboxamide represented by the formula (VIII) having a hydroxyl group, an amino group, a (substituted or unsubstituted) alkylamino group or the like bonded to the N atom, with a compound represented by the formula (VII-b) to produce N-(substituted-4-substituted)-6-(substituted or unsubstituted) phenoxy-2-pyridine carboxamide or thiocarboxamide represented by the formula (I-d),

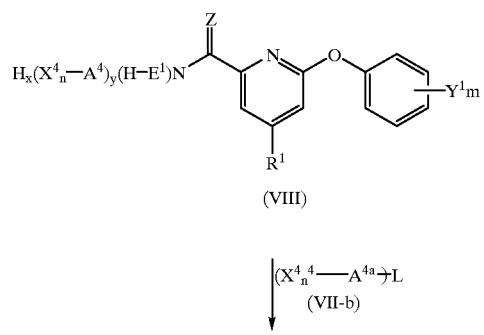

-continued

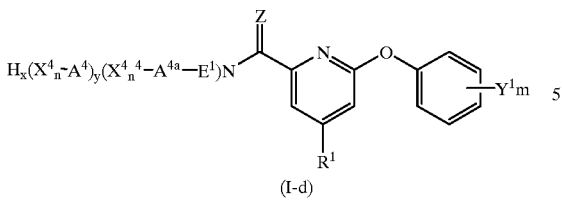

(I-d)

wherein $R^1$ is a $C_1$ to $C_4$ alkoxy group, a $C_1$ to $C_4$ alkylthio group, a $C_1$ to $C_4$ alkylamino group, a di($C_1$ to $C_4$ alkyl)amino group or a ($C_1$ to $C_4$ alkyl)($C_7$ to $C_8$ aralkyl)amino group;

$A^4$ may be substituted with $X^4$, and is a $C_1$ to $C_{10}$ alkyl group, a $C_3$ to $C_6$ alkenyl group, a $C_3$ to $C_6$ alkynyl group, a $C_3$ to $C_6$ cycloalkyl group, a phenyl group or an arylalkyl group whose alkyl moiety has 1 to 3 carbon atoms wherein the chain-like hydrocarbon moiety of $A^4$ is constituted by a longest carbon chain as a main chain exclusive of a $C_1$ to $C_4$ alkyl group bonded as side chain to said main chain, and said $C_1$ to $C_4$ alkyl group as side chain is regarded as $X^4$;

$A^{4a}$ may be substituted with $X^4$, and is a $C_1$ to $C_{10}$ alkyl group, a $C_3$ to $C_6$ alkenyl group, a $C_3$ to $C_6$ alkynyl group, a $C_3$ to $C_6$ cycloalkyl group or an arylalkyl group whose alkyl moiety has 1 to 3 carbon atoms wherein the chain-like hydrocarbon moiety of $A^{4a}$ is constituted by a longest carbon chain as a main chain exclusive of side chains bonded to said main chain, and said side chains are regarded as $X^4$;

$E^1H$ is a hydroxyl group, an amino group or a $C_1$ to $C_{10}$ alkylamino group which may be substituted with $X^4$ wherein the chain-like hydrocarbon moiety of $E^1$ is constituted by a longest carbon chain as a main chain exclusive of a $C_1$ to $C_4$ alkyl group bonded as side chain to said main chain, and said $C_1$ to $C_4$ alkyl group as side chain is regarded as $X^4$;

$X^4$ is a halogen atom, a $C_1$ to $C_4$ alkoxy group, a $C_1$ to $C_4$ alkylthio group, a $C_1$ to $C_4$ alkyl group which is not bonded to terminal positions of $A^4$ and $A^{4a}$ when $A^4$ and $A^{4a}$ are a $C_1$ to $C_{10}$ alkyl group, a $C_3$ to $C_6$ cycloalkyl group, a $C_1$ to $C_4$ alkylamino group, a di($C_1$ to $C_4$ alkyl)amino group, a $C_1$ to $C_4$ alkylsulfonyl group, a $C_1$ to $C_4$ alkylsulfinyl group, a hydroxyl group, an amino group, a cyano group or a thiol group, wherein the alkyl moiety of $X^4$ may be substituted with halogen atom(s);

n and $n^4$ are 0 or an integer selected from numbers of hydrogen atoms of $A^4$ and $A^{4a}$, respectively, which can be substituted with $X^4$, and when n and $n^4$ are an integer of not less than 2, $X^4$s may be the same or different;

x is 0 or 1 and y is 0 or 1 with the proviso that the sum of x and y is 1;

$Y^1$ is a $C_1$ to $C_4$ haloalkyl group, a $C_1$ to $C_4$ alkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom;

m is an integer of 0 to 5, and when m is not less than 2, $Y^1$s may be the same or different;

Z is an oxygen atom or a sulfur atom; and

L is a leaving group.

7. A process for producing N-substituted-4-substituted-6-(substituted or unsubstituted) phenoxy-2-pyridine carboxamide or thiocarboxamide as defined in claim 1 comprising:

reacting N-substituted-4-substituted-6-(substituted or unsubstituted) phenoxy-2-pyridine carboxamide represented by the formula (IX), having a hydroxyl group, an amino group, an alkylamino group which may be substituted with halogen atom or a thiol group in substituents bonded to the N atom, with a compound represented by the formula (VII-c) to produce N-substituted-4-substituted-6-(substituted or unsubstituted) phenoxy-2-pyridine carboxamide or thiocarboxamide represented by the formula (I-e),

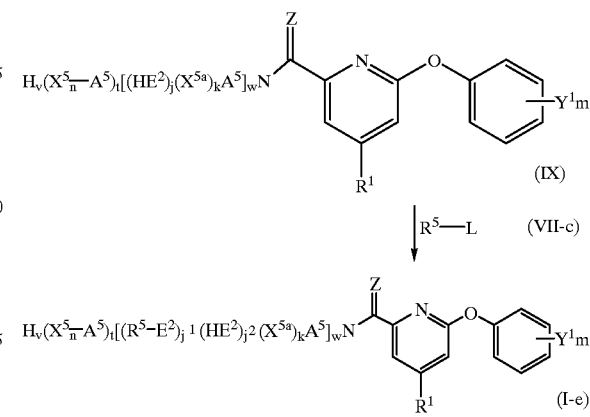

wherein $R^1$ is a $C_1$ to $C_4$ alkoxy group, a $C_1$ to $C_4$ alkylthio group, a $C_1$ to $C_4$ alkylamino group, a di($C_1$ to $C_4$ alkyl)amino group or a ($C_1$ to $C_4$ alkyl)($C_7$ to $C_8$ aralkyl)amino group;

$A^5$ may be substituted with $X^5$, and is a $C_1$ to $C_{10}$ alkyl group, a $C_2$ to $C_6$ alkenyl group, a $C_3$ to $C_6$ alkynyl group, a $C_3$ to $C_6$ cycloalkyl group, a $C_1$ to $C_{10}$ alkoxy group, a $C_3$ to $C_6$ alkenyloxy group, a $C_3$ to $C_6$ alkynyloxy group, a $C_1$ to $C_{10}$ alkylamino group, a di($C_1$ to $C_6$ alkyl)amino group, a phenyl group, a phenylamino group, an arylalkyl group whose alkyl moiety has 1 to 3 carbon atoms, an arylalkyloxy group whose alkyl moiety has 1 to 3 carbon atoms or an arylalkylamino group whose alkyl moiety has 1 to 3 carbon atoms, wherein the chain-like hydrocarbon moiety of $A^5$ is constituted by a longest carbon chain as a main chain exclusive of a $C_1$ to $C_4$ alkyl group bonded as side chain to said main chain, and said $C_1$ to $C_4$ alkyl group as side chain is regarded as $X^5$;

$X^5$ is a halogen atom, a $C_1$ to $C_4$ alkoxy group, a $C_1$ to $C_4$ alkylthio group, a $C_1$ to $C_4$ alkyl group which is not bonded to a terminal position of $A^5$ when $A^5$ is a $C_1$ to $C_{10}$ alkyl group, a $C_1$ to $C_{10}$ alkoxy group, a $C_1$ to $C_{10}$ alkylamino group or a di($C_1$ to $C_6$ alkyl)amino group, a $C_3$ to $C_6$ cycloalkyl group, a $C_1$ to $C_4$ alkylamino group, a di($C_1$ to $C_4$ alkyl)amino group, a $C_1$ to $C_4$ alkylsulfonyl group, a $C_1$ to $C_4$ alkylsulfinyl group, a hydroxyl group, an amino group, a cyano group or a thiol group, wherein the alkyl moiety of $X^5$ may be further substituted with halogen atom(s);

$X^{5a}$ is a halogen atom, a $C_1$ to $C_4$ alkoxy group, a $C_1$ to $C_4$ alkylthio group, a $C_1$ to $C_4$ alkyl group which is not bonded to a terminal position of $A^5$ when $A^5$ is a $C_1$ to $C_{10}$ alkyl group, a $C_1$ to $C_{10}$ alkoxy group, a $C_1$ to $C_{10}$ alkylamino group or a di($C_1$ to $C_6$ alkyl)amino group, a $C_3$ to $C_6$ cycloalkyl group, a di($C_1$ to $C_4$ alkyl)amino group, a $C_1$ to $C_4$ alkylsulfonyl group, a $C_1$ to $C_4$ alkylsulfinyl group or a cyano group, wherein the alkyl moiety of $X^{5a}$ may be further substituted with halogen atom(s);

n is 0 or an integer selected from numbers of hydrogen atoms of $A^5$ which can be substituted with $X^5$;

when n is an integer of not less than 2, $X^5$s may be the same or different;

t is 0 or 1, v, is 0 or 1 and w is 1 or 2 with the proviso that the sum of t and v, is 0 or 1 and the sum of t, v, and w is 2;

when w is 2 and t and w are 1, $A^5$s may be the same or different;

when w is 2 and $A^5$s are alkyl chains, the $A^5$s may be directly bonded together to form a ring, or the $A^5$s may be bonded to each other through an oxygen atom of the hydroxyl group, or a nitrogen atom of the amino group or the $C_1$ to $C_4$ alkylamino group which groups are bonded to one of the $A^5$s, to form a ring;

$E^2H$ is a hydroxyl group, an amino group, a thiol group or a $C_1$ to $C_4$ alkylamino group which may be substituted with a halogen atom;

$R^5$ a $C_1$ to $C_4$ alkyl group which may be substituted with a halogen atom;

j is an integer of not less than 1 and k is an integer of not less than 0 with the proviso that the sum of j and k is 1 or an integer selected from numbers of hydrogen atoms of $A^5$ which can be substituted with $X^5$;

when j is not less than 2, $E^2$Hs may be the same or different;

when k is not less than 2, $X^{5a}$s may be the same or different;

$j^1$ is an integer of not less than 1 and $j^2$ is an integer of not less than 0 with the proviso that the sum of $j^1$ and $j^2$ is j;

$Y^1$ is a $C_1$ to $C_4$ haloalkyl group, a $C_1$ to $C_4$ alkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom;

m is an integer of 0 to 5, and when m is not less than 2, $Y^1$s may be the same or different;

Z is an oxygen atom or a sulfur atom; and

L is a leaving group.

8. A process for producing N-(substituted or unsubstituted)-4-substituted-6-(substituted or unsubstituted) phenoxy-2-pyridine carboxamide or thiocarboxamide as defined in claim 1, comprising:

reacting N-(substituted or unsubstituted)-4-substituted-6-halogeno-2-pyridine carboxamide or thiocarboxamide represented by the formula (X) with (substituted or unsubstituted) phenol represented by the formula (XI) under basic condition to produce N-(substituted or unsubstituted)-4-substituted-6-(substituted or unsubstituted) phenoxy-2-pyridine carboxamide or thiocarboxamide represented by the formula (I-f),

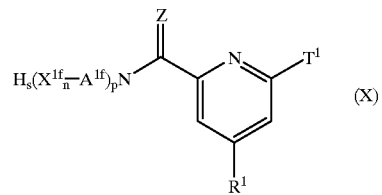

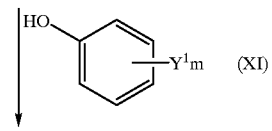

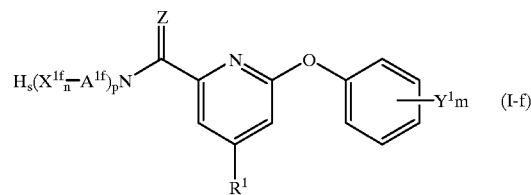

wherein $R^1$ is a $C_1$ to $C_4$ alkoxy group, a $C_1$ to $C_4$ alkylthio group, a $C_1$ to $C_4$ alkylamino group, a di($C_1$ to $C_4$ alkyl)amino group or a ($C_1$ to $C_4$ alkyl)($C_7$ to $C_8$ aralkyl)amino group;

$A^{1f}$ may be substituted with $X^{1f}$, and is a $C_1$ to $C_{10}$ alkyl group, a $C_2$ to $C_6$ alkenyl group, a $C_3$ to $C_6$ alkynyl group, a $C_3$ to $C_6$ cycloalkyl group, a $C_1$ to $C_{10}$ alkoxy group, a $C_3$ to $C_6$ alkenyloxy group, a $C_3$ to $C_6$ alkynyloxy group, a $C_1$ to $C_{10}$ alkylamino group, a di($C_1$ to $C_6$ alkyl)amino group, a phenyl group, a phenylamino group, an arylalkyl group whose alkyl moiety has 1 to 3 carbon atoms, an arylalkyloxy group whose alkyl moiety has 1 to 3 carbon atoms, an arylalkylamino group whose alkyl moiety has 1 to 3 carbon atoms or a hydroxyl group, wherein the chain-like hydrocarbon moiety of $A^{1f}$ is constituted by a longest carbon chain as a main chain exclusive of a $C_1$ to $C_4$ alkyl group bonded as side chain to said main chain, and said $C_1$ to $C_4$ alkyl group as side chain is regarded as $X^{1f}$;

$X^{1f}$ is a halogen atom, a $C_1$ to $C_4$ alkoxy group, a $C_1$ to $C_4$ alkylthio group, a $C_1$ to $C_4$ alkyl group, which is not bonded to a terminal position of $A^{1f}$ when $A^{1f}$ is a $C_1$ to $C_{10}$ alkyl group, a $C_1$ to $C_{10}$ alkoxy group, a $C_1$ to $C_{10}$ alkylamino group or a di($C_1$ to $C_6$ alkyl)amino group, a $C_3$ to $C_6$ cycloalkyl group, a $C_1$ to $C_4$ alkylcarbonyl group, a $C_1$ to $C_4$ alkylamino group, a di($C_1$ to $C_4$ alkyl)amino group, a $C_1$ to $C_4$ alkylsulfonyl group, a $C_1$ to $C_4$ alkylsulfinyl group, a hydroxyl group, an amino group, a cyano group or a thiol group, wherein the alkyl moiety of $X^{1f}$ may be further substituted with halogen atom(s);

n is 0 or an integer selected from numbers of hydrogen atoms of $A^{1f}$ which can be substituted with $X^{1f}$, and when n is an integer of not less than 2, $X^{1f}$s may be the same or different;

p and s are an integer of 0 to 2 with the proviso that the sum of p and s is 2;

when p is 2, $A^{1\prime}$s may be the same or different;

when p is 2 and $A^{1\prime}$s are alkyl chains, the $A^{1\prime}$s may be directly bonded together to form a ring, or the $A^{1\prime}$s may be bonded to each other through an oxygen atom of the hydroxyl group, or a nitrogen atom of the amino group or the $C_1$ to $C_4$ alkylamino group which groups are bonded to one of the $A^{1\prime}$s, to form a ring;

$Y^1$ is a $C_1$ to $C_4$ haloalkyl group, a $C_1$ to $C_4$ alkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom;

m is an integer of 0 to 5, and when m is not less than 2, $Y^1$s may be the same or different;

Z is an oxygen atom or a sulfur atom; and $T^1$ is a halogen atom.

9. A herbicide composition comprising as an effective ingredient N-(substituted or unsubstituted)-4-substituted-6-(substituted or unsubstituted) phenoxy-2-pyridine carboxamide or thiocarboxamide and preparation auxiliaries or adjuvants, said N-(substituted or unsubstituted)-4-substituted-6-(substituted or unsubstituted) phenoxy-2-pyridine carboxamide or thiocarboxamide being represented by the formula (I),

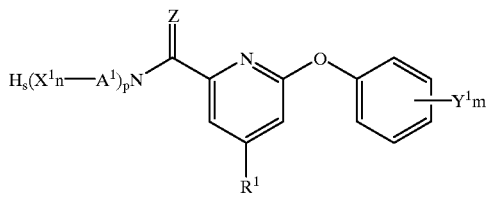

(I)

wherein $R^1$ is a $C_1$ to $C_4$ alkoxy group or a $C_1$ to $C_4$ alkylthio group;

$A^1$ is optionally substituted with $X^1$, and is a $C_1$ to $C_{10}$ alkyl group, a $C_2$ to $C_6$ alkenyl group, a $C_3$ to $C_6$ alkynyl group, a $C_3$ to $C_6$ cycloalkyl group, a $C_1$ to $C_{10}$ alkoxy group, a $C_3$ to $C_6$ alkenyloxy group, a $C_3$ to $C_6$ alkynyloxy group, a $C_1$ to $C_{10}$ alkylamino group, a di($C_1$ to $C_6$ alkyl)amino group, a phenyl group, a phenylamino group, an arylalkyl group whose alkyl moiety has 1 to 3 carbon atoms, an arylalkyloxy group whose alkyl moiety has 1 to 3 carbon atoms, an arylalkylamino group whose alkyl moiety has 1 to 3 carbon atoms, an amino group or a hydroxyl group wherein the chain-like hydrocarbon moiety of $A^1$ is constituted by a longest carbon chain as a main chain exclusive of a $C_1$ to $C_4$ alkyl group bonded as side chain to said main chain, and said $C_1$ to $C_4$ alkyl group as side chain is regarded as $X^1$;

$X^1$ is a halogen atom, a $C_1$ to $C_4$ alkoxy group, a $C_1$ to $C_4$ alkylthio group, a $C_1$ to $C_4$ alkyl group, which is not bonded to a terminal position of $A^1$ when $A^1$ is a $C_1$ to $C_{10}$ alkyl group, a $C_1$ to $C_{10}$ alkoxy group, a $C_1$ to $C_{10}$ alkylamino group or a di($C_1$ to $C_6$ alkyl)amino group, a $C_3$ to $C_6$ cycloalkyl group, a $C_1$ to $C_4$ alkylcarbonyl group, a $C_1$ to $C_4$ alkylamino group, a di($C_1$ to $C_4$ alkyl)amino group, a $C_1$ to $C_4$ alkylsulfonyl group, a $C_1$ to $C_4$ alkylsulfinyl group, a hydroxyl group, an amino group, a cyano group or a thiol group, wherein the alkyl moiety of $X^1$ is optionally substituted with halogen atom(s);

n is 0 or an integer selected from numbers of hydrogen atoms of $A^1$ which can be substituted with $X^1$, and when n is an integer of not less than 2, $X^1$s may be the same or different;

p and s are an integer of 0 to 2 with the proviso that the sum of p and s is 2;

when p is 2, $A^1$ may be the same or different;

when p is 2 and two $A^1$s are alkyl chains, the $A^1$s may be directly bonded together to form a ring, or the $A^1$s may be bonded to each other through an oxygen atom of the hydroxyl group, or a nitrogen atom of the amino group or the $C_1$ to $C_4$ alkylamino group which groups are bonded to one of the $A^1$s, to form a ring;

$Y^1$ is a $C_1$ to $C_4$ haloalkyl group, a $C_1$ to $C_4$ alkyl group, a $C_1$ to $C_4$ alkoxy group, a $C_1$ to $C_4$ haloalkoxy group, a $C_1$ to $C_4$ alkylthio group, a $C_1$ to $C_4$ haloalkylthio group or a halogen atom;

m is an integer of 0 to 5, and when m is not less than 2, $Y^1$s may be the same or different; and Z is an oxygen atom or a sulfur atom.

* * * * *